(12) United States Patent
Joshi et al.

(10) Patent No.: US 10,995,114 B2
(45) Date of Patent: May 4, 2021

(54) SCALABLE PRODUCTION OF GENETICALLY ENGINEERED NANOFIBROUS MACROSCOPIC MATERIALS VIA FILTRATION

(71) Applicant: President and Fellows of Harvard College, Cambridge, MA (US)

(72) Inventors: Neel Satish Joshi, Somerville, MA (US); Noémie-Manuelle Dorval Courchesne, Montréal (CA); Anna M. Duraj-Thatte, Boston, MA (US); Peter Q. Nguyen, Malden, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 12 days.

(21) Appl. No.: 16/302,315

(22) PCT Filed: May 16, 2017

(86) PCT No.: PCT/US2017/032923
§ 371 (c)(1),
(2) Date: Nov. 16, 2018

(87) PCT Pub. No.: WO2017/201061
PCT Pub. Date: Nov. 23, 2017

(65) Prior Publication Data
US 2019/0315799 A1    Oct. 17, 2019

Related U.S. Application Data

(60) Provisional application No. 62/401,389, filed on Sep. 29, 2016, provisional application No. 62/336,937, filed on May 16, 2016.

(51) Int. Cl.
*C07K 1/34* (2006.01)
*B01D 61/14* (2006.01)
(Continued)

(52) U.S. Cl.
CPC .............. *C07K 1/34* (2013.01); *B01D 61/147* (2013.01); *C07K 14/47* (2013.01); *C08J 5/18* (2013.01); *D01F 4/06* (2013.01); *C08J 2389/00* (2013.01)

(58) Field of Classification Search
None
See application file for complete search history.

(56) References Cited

U.S. PATENT DOCUMENTS 6,455,256 B1   9/2002   Engel
7,476,370 B2   1/2009   Mitsugashira et al.

FOREIGN PATENT DOCUMENTS

WO         2014/176311 A1   10/2014
WO    WO 2014/176311      * 10/2014

OTHER PUBLICATIONS

Barnhart et al., Annu. Rev. Microbiol. 60: 131-47 (2006).*
(Continued)

*Primary Examiner* — Erin M. Bowers
(74) *Attorney, Agent, or Firm* — Foley Hoag LLP

(57) ABSTRACT

Provided herein are filtration-based purification methods for amyloid fibers, such as curli fibers, directly from microbial culture, and their fabrication into free-standing thin films. Additionally, methods for recycling amyloid fibers thing films by, for example, disassembly and re-assembly, are disclosed herein.

11 Claims, 28 Drawing Sheets
Specification includes a Sequence Listing.

With CsgB
(cell surface anchoring)

Without CsgB
(no cell surface anchoring)

(51) Int. Cl.
*C07K 14/47* (2006.01)
*C08J 5/18* (2006.01)
*D01F 4/06* (2006.01)

(56) References Cited

OTHER PUBLICATIONS

Cologgi et al., Extracellular reduction of uranium via Geobacter conductive pili as a protective cellular mechanism. Proc Natl Acad Sci U S A. Sep. 13, 2011;108(37)15248-52.
Hamano et al., High expression of Lin28 is associated with tumour aggressiveness and poor prognosis of patients in pesophagus cancer. Br J Cancer. Apr. 10, 2012;106(8)1415-23.
Kalab, Microstructure of Bacterial Filters Used as Support in Scanning Electron Microscopy. SCIMAT. Retrieved online at: http://www.magma.ca/~pavel/science/BactFilters.htm. 2 pages, Apr. 18, 2006.
Levine, Soluble multimeric Alzheimer beta(1-40) pre-amyloid complexes in dilute solution. Neurobiol Aging. Sep.-Oct. 1995;16(5):755-64.
Wang et al., In vitro polymerization of a functional *Escherichia coli* amyloid protein. J Biol Chem. Feb. 9, 2007;282(6):3713-9.
Yu et al., Conductive artificial biofilm dramatically enhances bioelectricity production in Shewanella-inoculated microbial fuel cells. Chem Commun (Camb). Dec. 28, 2011;47(48):12825-7.
International Search Report and Written Opinion for Application No. PCT/US2017/032923, dated Sep. 28, 2017, 14 pages.
International Preliminary Report on Patentability for Application No. PCT/US2017/032923, dated Nov. 29, 2018, 11 pages.

* cited by examiner

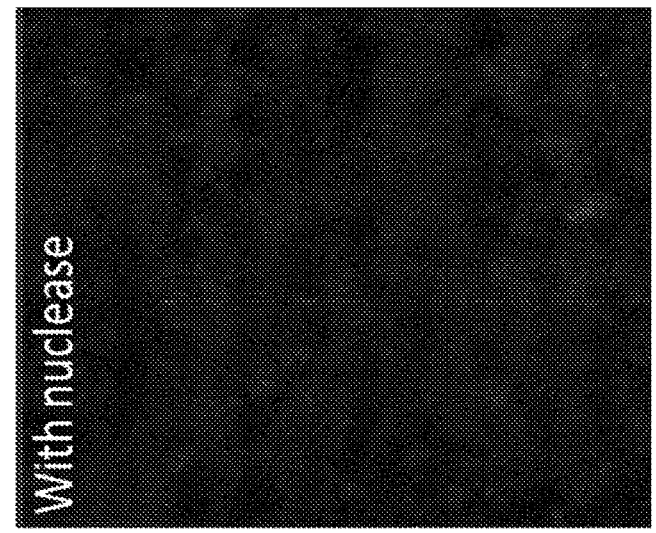
FIG. 9B
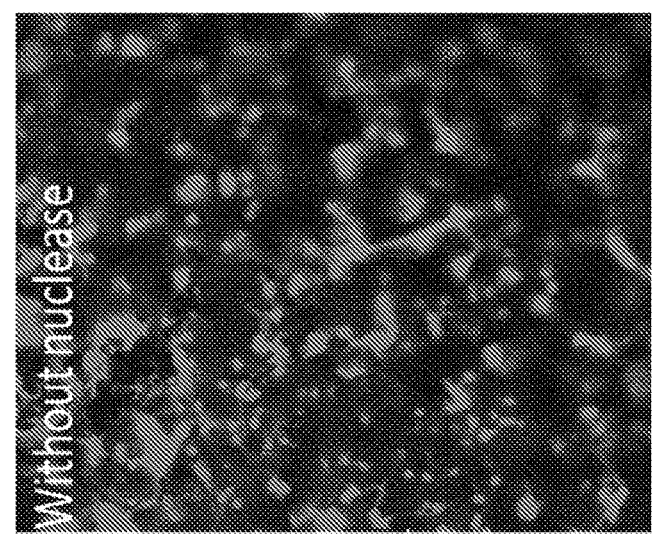
FIG. 9A
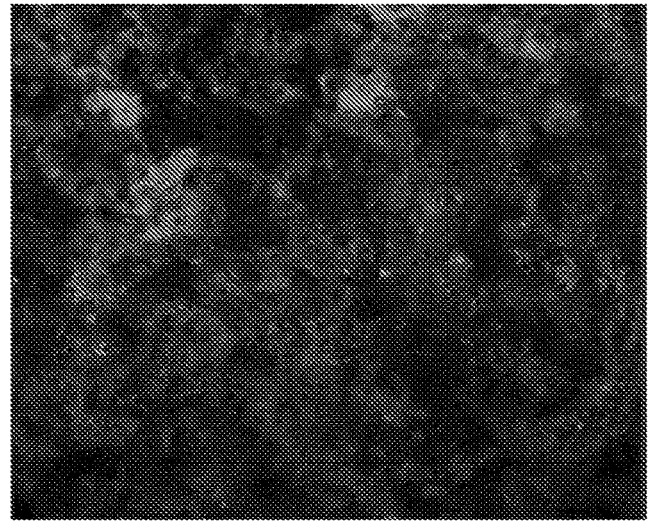

100 mL, wild-type curli 40 mL, wild-type curli

Smooth film of purified curli fibers covering the fabric mesh

Purified curli fibers bridging two textile fibers

SEQUENCE LISTING

```
<160> NUMBER OF SEQ ID NOS: 5

<210> SEQ ID NO 1
<211> LENGTH: 151
<212> TYPE: PRT
<213> ORGANISM: Escherichia coli

<400> SEQUENCE: 1

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
            115                 120                 125

Thr Ala Ser Asn Ser Ser Val Asn Val Thr Gln Val Gly Phe Gly Asn
            130                 135                 140

Asn Ala Thr Ala His Gln Tyr
145                 150
```

```
<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala His Ile Val Met Val Asp Ala Tyr Lys Pro Thr Lys
1               5                   10

<210> SEQ ID NO 4
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile
        115

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Ser Gly Gly Ser Gly Gly Ser Gly Gly Ser Gly Gly Ser Gly Gly
1               5                   10                  15
```

```
Ser Gly Gly Ser Gly Gly Ser Gly Gly Ser Gly Gly Ser Gly Gly Ser
                20                  25                  30
Gly Gly Ser Gly
        35
```

SCALABLE PRODUCTION OF GENETICALLY ENGINEERED NANOFIBROUS MACROSCOPIC MATERIALS VIA FILTRATION

RELATED APPLICATIONS

This application is a 35 U.S.C. § 371 national stage filing of International Application No. PCT/US2017/032923, filed on May 16, 2017, which in turn claims priority to U.S. Provisional Patent Application No. 62/336,937, filed on May 16, 2016 and U.S. Provisional Patent Application No. 62/401,389, filed on Sep. 29, 2016. The entire contents of each of the foregoing applications is expressly incorporated herein by reference.

SEQUENCE LISTING

The instant application contains a Sequence Listing which has been submitted electronically in ASCII format and is hereby incorporated by reference in its entirety. Said ASCII copy, created on Jul. 13, 2017, is named 117823-13520 SL.txt and is 3,820 bytes in size.

STATEMENT OF GOVERNMENT SUPPORT

This invention was made with government support under Grant 1410751 awarded by the National Science Foundation. The government has certain rights in the invention.

BACKGROUND

The unique self-assembling properties of amyloid proteins make them attractive nanofibrous materials for a variety of applications. They readily form high surface area networks with nanoscale pore sizes, are highly resistant to harsh environments, and can be used under various stages of assembly (monomeric proteins, oligomers, fiber or large aggregates). Furthermore, their proteinaceous structure lends itself to structural customization, whereby the amyloid fibers serve as a scaffold for the display of protein and peptide domains with various functions. Mankar et al., Nanomaterials: amyloids reflect their brighter side, *Nano Reviews* 2, 10 (2011); Chen et al., Synthesis and patterning of tunable multiscale materials with engineered cells. *Nat Mater* 13(5):515-523 (2014); Rudra et al., Self-assembled peptide nanofibers raising durable antibody responses against a malaria epitope. *Biomaterials* 33(27):6476-6484 (2012).

Recently, attempts at controlling the morphology, size and shape of amyloid proteins has been achieved by varying assembly conditions, and they are beginning to be used for various applications including, water purification, vaccine scaffolds, tissue engineering scaffolds, drug delivery, templates for polymerization, environmental carbon capture, self-assembling catalysts for nanomaterial assembly or components of composite films, among others. Andersson et al., Modulation of Curli Assembly and Pellicle Biofilm Formation by Chemical and Protein Chaperones. *Chemistry & biology* 20(10):1245-1254 (2013); Schreck & Yuan, A Kinetic Study of Amyloid Formation: Fibril Growth and Length Distributions. *The Journal of Physical Chemistry B* 117(21):6574-6583 (2013); Knowles et al, Nanostructured films from hierarchical self-assembly of amyloidogenic proteins. *Nat Nano* 5(3):204-207 (2010); Bolisetty & Mezzenga, Amyloid-carbon hybrid membranes for universal water purification. *Nat Nano* 11(4): 365-371 (2016); Knowles & Mezzenga, Amyloid Fibrils as Building Blocks for Natural and Artificial Functional Materials. *Advanced Materials* (2016); Meier et al., Conducting Core-Shell Nanowires by Amyloid Nanofiber Templated Polymerization. *Biomacromolecules* 16(2):558-563 (2015).

Most reports of amyloid-based materials use either short synthetic peptides or proteins isolated from natural sources as starting components. Naturally occurring proteins are attractive because they can be abundant and readily available. Indeed, many proteins that have no known amyloidogenicity in their natural environment can easily be induced to self-assemble into amyloids by various denaturing treatments. Meier & Welland, Wet-Spinning of Amyloid Protein Nanofibers into Multifunctional High-Performance Biofibers. *Biomacromolecules* 12(10):3453-3459 (2011); Jung et al., Structure of Heat-Induced β-Lactoglobulin Aggregates and their Complexes with Sodium-Dodecyl Sulfate. *Biomacromolecules* 9(9):2477-2486 (2008).

However, in addition to easily inducing amyloid formation, it would also be advantageous to control over the sequence of the self-assembling unit in order to tailor the material for specific applications. One approach to this is to use solid phase techniques to chemically synthesize the desired sequences. While this works for short (<40 amino acid) sequences, it comes at the expense of scalability and lacks the self-propagating ability of biological entities for the production of living materials. Alternatively, larger amyloidogenic proteins with customized sequences can be produced recombinantly. In fact, the ability to tune the sequences of amyloid proteins can lead to enhancements of their self-assembling properties, increased stability, better processability, and easily accessible modifications with functional pendant domains. Peralta et al., Engineering Amyloid Fibrils from β-Solenoid Proteins for Biomaterials Applications. *ACS Nano* 9(1):449-463 (2015); Woolfson & Mahmoud, More than just bare scaffolds: towards multicomponent and decorated fibrous biomaterials. *Chemical Society Reviews* 39(9):3464-3479 (2010).

Of particular interest are curli nanofibers, a class of functional amyloid that is naturally produced by *Escherichia coli* for the purposes of surface adhesion and biofilm formation. Chapman et al., Role of *Escherichia coli* Curli Operons in Directing Amyloid Fiber Formation. *Science* 295(5556):851-855 (2002); Evans & Chapman, Curli Biogenesis: Order out of Disorder. *Biochimica et biophysica acta* 1843(8):1551-1558 (2014). Given the ease with which *E. coli* can be engineered to produce recombinant proteins, these curli nanofibers are of great interest for producing genetically engineered materials. Indeed, engineered curli fibers displaying fused protein and peptide domains have been used to imbue bacterial biofilms with a variety of functions, including specific binding to metallic surfaces, antibody and enzyme display, and the ability to template inorganic nanoparticle growth. This makes curli-based materials potentially useful for applications in custom fabricated surface coatings, biocatalysts, and electronically conductive materials. Chen et al., Synthesis and patterning of tunable multiscale materials with engineered cells. *Nat Mater* 13(5):515-523 (2014); Van Gerven et al., Secretion and functional display of fusion proteins through the curli biogenesis pathway. *Molecular Microbiology* 91(5):1022-1035 (2014); Chen et al., Engineering Living Functional Materials. *ACS Synthetic Biology* 4(1):8-11 (2015); Zhong et al., Strong underwater adhesives made by self-assembling multi-protein nanofibres. *Nat Nano* 9(10):858-866 (2014).

A significant hurdle to widespread implementation, however, is the large-scale production of genetically engineered amyloid materials. Most purification protocols for curli fibers were developed to study their biological and self-assembly properties, and consequently are not optimized to achieve high yields. They have generally employed one of three methods. First, poly-histidine-tagged curli nanofibers are often used as affinity tags and combined with centrifugation, lysis and column chromatography, but this process is time consuming. Second, pure curli fibers have also been obtained by performing SDS-PAGE on cell lysate for several hours, a tedious process which also requires several centrifugation, rinsing and boiling steps. Chapman et al., Role of *Escherichia coli* Curli Operons in Directing Amyloid Fiber Formation. *Science,* 295(5556):851-855 (2002); Zhou et al., Experimental Manipulation of the Microbial Functional Amyloid Called Curli. In *Bacterial Cell Surfaces: Methods and Protocols*, Delcour, H. A., Ed. Humana Press: Totowa, N.J., 2013; pp 53-75; Collinson et al., Purification and characterization of thin, aggregative fimbriae from *Salmonella enteritidis*. *Journal of Bacteriology* 173(15):4773-4781 (1991). Third, curli nanofibers can also be purified from cell lysate via salt precipitation and sequential differential centrifugation. Chapman et al., Role of *Escherichia coli* Curli Operons in Directing Amyloid Fiber Formation. *Science,* 295(5556):851-855 (2002). Yields of purified curli fibers for such techniques are likely in the low milligram or sub-milligram range. Additionally, the procedures require expensive reagents or instrumentation. Reports also include the sequential combination of these three methods, resulting in fibers with a higher purity but a lower yield. Apart from the small quantities of materials obtained from these labor-intensive processes, the requirement for an affinity tag can also interfere with some end-goal applications.

As interest in using proteins to assemble functional, biocompatible and environmentally-friendly materials increases, developing scalable protocols for producing recombinant proteins coupled to straightforward fabrication processes is becoming crucial. Accordingly, in order to produce enough curli nanofibers to construct films, gels or other functional materials, a tag-less, simpler, faster and higher yielding method is needed.

SUMMARY

The methods described herein provide a simple and versatile method for purifying amyloid fibers, such as curli nanofibers, at a scale large enough to facilitate their use in materials applications. Specifically, the methods presented herein reproducibly produce hundreds of milligrams of semi-pure protein per liter from standard shaker flasks, without any significant expression optimization. Moreover, functionalizing polypeptides displayed on amyloid fibers surprisingly retain their functionalizing activity following the purification methods of the present invention.

The methods are based on filtration purification to separate extracellular amyloid, e.g., curli fiber aggregates, from bacteria and other cellular debris, rather than the use of an affinity tag. The present disclosure provides several advantages over traditional protein purification methods. The methods provided herein are simple and fast; do not require protein tags and do not rely on any binding affinity; are easily scalable, allow for the purification of curli fibers from several liters of bacterial cultures; and are highly versatile and can be used to purify a wide range of genetically engineered amyloid fibers displaying diverse functional groups. The present disclosure provides the first demonstration wherein amyloid fibers are purified straight from a microbial culture, e.g., a culture of bacteria, without having to lyse the microbial cells. Moreover, and contrary to prior methods which require the use of filters with small pore sizes (~0.2 microns) to achieve high yields of purification, the use of a filter having a larger pore size (for example, 1 micron or larger) surprisingly allows the efficient purification of amyloid fibers directly from complex mixtures, such as a microbial culture. Filters having a pore size larger than the size of the microorganisms present in the microbial culture may be used in the methods described herein. Furthermore, the present disclosure provides the first example of filtration-based purification of genetically engineered amyloid fibers for materials purposes.

The methods of the present disclosure may be used to purify any type of amyloid fiber by filtration, including, but not limited to curli fibers, or fibers composed of CsgA, β-lactoglobulin, sup-35, Ure2p, α-synuclein, amyloid β-protein (Aβ), medin, prolactin, gelsolin, calcitonin, cystatin, transthyretin, Pmel17, and β2-microglobulin. With their high resistance to heat, detergents, solvents and denaturing agents, engineered curli nanofibers remain functional throughout the rigorous processing, and can be used to assemble macroscopic materials directly from broth culture.

In some embodiments, the methods described herein may be performed using vacuum filtration (e.g., using vacuum generated with a pump). In some embodiments, the methods described herein may be performed using gravity filtration. In some embodiments, the methods described herein may be performed using centrifugal filtration. In some embodiments, the methods described herein may be performed using filter plates for small scale purification. The filtration set-ups used in the methods described herein may include vacuum filtration holders, butchner funnels, tabletop filtration systems, and the like.

In some embodiments, the amyloid fibers can be genetically engineered or can be naturally-occurring (i.e., not genetically engineered). In some embodiments, genetically engineered amyloid fibers contain mutations (e.g., point mutations, random mutations, deletions, insertions, frame shifts). In some embodiments, genetically engineered amyloid fibers are fused or attached to a linker, tag (e.g., a polypeptide or nucleic acid tag), protein, enzyme, catalytic site, metal binding domain, conjugation domain, or other fusion. In exemplary embodiments, curli nanofibers, e.g., genetically engineered curli nanofibers, are purified using the methods of the disclosure.

The methods described herein can be used to scale up the production of amyloid, e.g., curli, nanofibers. For example, the methods can be used to purify non-naturally-occurring curli nanofibers engineered to have CsgA polypeptides fused to linker and an activity polypeptide, such as a conjugation domain, functionalizing protein or a metal-binding domain. The amyloid fibers purified using the methods described herein can comprise Biofilm-Integrated Nanofiber Display (BIND), which can be used to make curli-based materials useful for applications in surface coatings (e.g., custom fabricated surface coatings), biocatalysts, and electronically conductive materials. The amyloid fibers purified using the methods described herein may be used as precursor materials for a multitude of applications. In some embodiments, the amyloid fibers purified using the methods described herein are suitable for use in an application selected from the group consisting of: biocatalysis, chemical production, filtration, isolation of molecules from an aqueous solution, water filtration, bioremediation, nanoparticle synthesis, nanowire synthesis, display of optically active materials, surface coating, structural reinforcement of an object, and delivery of a therapeutic agent. In some embodiments, the amyloid fibers purified using the methods described herein may be used as biocatalysts, as filtration devices, as coatings, as therapeutic drug delivery agents, or as electroconductive materials. Recombinant CsgA polypeptides, curli fibers and biofilms, and methods of producing recombinant CsgA polypeptides, curli fibers and biofilms have been described previously in U.S. Patent Publication No. 2016/0185828 A1, and U.S. Provisional Patent Application Nos. 62/143,560, 62/257,441, 62/336,937, and 62/354,843, the contents of each which are expressly incorporated herein by reference in their entireties.

In some embodiments, bacteria (e.g., *E. coli*), yeast (e.g., *Saccharomyces cerevisiae* or *Schizosaccharomyces pombe*), or fungi, are used to produce amyloid protein nanofibers that are key constituents of the biofilm extracellular matrix, and the protein nanofiber aggregates are purified using a vacuum filtration procedure.

The methods described herein can isolate at least 100 milligrams per liter of semi-pure amyloid fibers. In some embodiments, the methods described herein can isolate at least 10 milligrams per liter of semi-pure amyloid fibers. In some embodiments, the semi-pure amyloid fibers are isolated in about 30 minutes from induced bacterial culture.

The filtration purification methods described herein are streamlined and scalable and can be used in the fabrication of various macroscopic protein-based materials. The methods described herein can be used to fabricate free-standing amyloid thin films composed exclusively of amyloid fibers, e.g., engineered curli fibers, directly from broth culture, all while maintaining the functionality of peptide and protein domains fused to the fibers that confer new specific binding activity to the material.

The methods described herein can be used to disassemble and reassemble purified amyloid fibers, e.g., engineered curli fibers, into thin films. Fibers purified by filtration can be disassembled, and then thin films can be reassembled on various substrates. Through disassembly and reassembly cycles, curli-based materials can be recycled for further materials processing.

In one aspect, the invention provides a method of purifying an amyloid fiber comprising contacting a composition comprising the amyloid fiber with a filter; and washing the filter; thereby purifying the amyloid fiber on the filter.

In one aspect, the invention provides a method of purifying an amyloid fiber from a microbial culture comprising contacting the microbial culture comprising the amyloid fiber with a filter, wherein the composition comprises a microbial culture which has not been lysed prior to the contacting step; and washing the filter; thereby purifying the amyloid fiber on the filter.

In some embodiments, the method further comprises contacting the filter with a solubilization agent. In some embodiments, the solubilization agent is selected from the group consisting of guanidine hydrochloride, urea, dimethyl sulfoxide (DMSO), sodium dodecyl sulfate (SDS), beta-mercaptoethanol, and n-propanol.

In some embodiments, the method further comprises contacting the filter with a DNAse. In some embodiments, the method further comprises contacting the filter with a RNAse.

In some embodiments, the method further comprises contacting the filter with a surfactant. In some embodiments, the surfactant is an ionic surfactant. In some embodiments, the surfactant is a non-ionic surfactant. In some embodiments, the surfactant is selected from the group consisting of SDS, 4-octylphenol polyethoxylate, polyethylene glycol sorbitan monolaurate, and polyethylene glycol sorbitan monooleate.

In some embodiments, the amyloid fiber is selected from the group consisting of a curli fiber, a fiber composed of CsgA, β-lactoglobulin, sup-35, Ure2p, α-synuclein, amyloid β-protein (Aβ), medin, prolactin, gelsolin, calcitonin, cystatin, transthyretin, Pmell 7, and β2-microglobulin.

In some embodiments, the curli fiber comprises a CsgA polypeptide.

In some embodiments, the CsgA polypeptide further comprises a linker and an activity polypeptide, wherein the activity polypeptide is a polypeptide selected from the group consisting of: a conjugation domain, a functionalizing polypeptide, a Histidine tag, a silk protein, a nanobody, a metal binding domain (MBD), a graphene binding (GBP) domain, a carbon nanotube binding (CBP) domain, a gold binding (A3) domain, CT43, FLAG, Z8, E14, QBP1, CLP12, and AFP8; and wherein the linker is attached at one end to the CsgA polypeptide and at the other end to the activity polypeptide.

In some embodiments, the linker is attached to the C-terminus of the CsgA polypeptide or the N-terminus of the CsgA polypeptide.

In some embodiments, the conjugation domain is selected from the group consisting of: SpyTag, EFCA, WRESAI, ARVCF, CaM, SZ21, VMAN11, and DnaEΔC35.

In some embodiments, the conjugation domain is selected from the group consisting of: SpyCatcher, a PDZ domain, Tip1, InaD, M13, SZ16, VMAΔN11, and DnaEC35.

In some embodiments, the CsgA polypeptide is contacted with a partner conjugation domain attached to a functionalizing polypeptide, wherein the partner conjugation domain is selected from the group consisting of SpyCatcher, a PDZ domain, Tip1, InaD, M13, SZ16, VMAΔN11, and DnaEC35.

In some embodiments, the CsgA polypeptide is contacted with a partner conjugation domain attached to a functionalizing polypeptide, wherein the partner conjugation domain is selected from the group consisting of SpyTag, EFCA, WRESAI, ARVCF, CaM, SZ21, VMAN11, and DnaEΔC35.

In some embodiments, the CsgA polypeptide and the partner conjugation domain are contacted on the filter before the washing or after the washing.

In some embodiments, the functionalizing protein is an enzyme or a metal binding domain.

In some embodiments, the method also purifies a component of the extracellular matrix of a bacteria or a filamentous protein structure; wherein the component of the extracellular matrix is cellulose, a flagella, a pili, or a bacterial nanowire; or wherein the filamentous protein structure is a filamentous bacteriophage, a M13 bacteriophage, a recombinant protein fiber, silk, collagen, or a fiber-like structure. In some embodiments, the pili is a *Geobacter* pili. In some embodiments, the bacterial nanowire is a *Shewanella* nanowire.

In some embodiments, the method comprises using an engineered microbial cell produces the amyloid fiber. In some embodiments, the engineered microbial cell is a bacterium or a fungus. In some embodiments, the bacterium or the fungus is selected from the group consisting of *Escherichia coli, Salmonella*, or a yeast.

In some embodiments, the bacterium is an *E. coli* comprising a csgBACEFG operon or a csgACEFG operon.

In some embodiments, the bacterium is an *E. coli* strain comprising a deletion in an endogenous csgB gene. In some embodiments, the bacterium is an *E. coli* strain comprising a deletion in an endogenous csgD gene.

In some embodiments, the filter is a filter membrane, a mesh, a cloth, or a textile.

In some embodiments, the filter is a filter membrane, and wherein the filter membrane comprises polycarbonate, nylon, cellulose, polytetrafluoroethylene, polyethersulfone, polyvinylidene fluoride, or polyvinyidene chloride. In some embodiments, the filter is a filter membrane, and wherein the filter membrane is a polycarbonate membrane.

In some embodiments, the filter is a mesh, and the mesh is a metal mesh, a glass mesh, a ceramic mesh, a plastic mesh, or a polymer mesh.

In some embodiments, the method comprises removing the amyloid fiber from the filter after washing.

In some embodiments, the amyloid fiber is removed from the filter after washing, and the CsgA polypeptide is contacted with the partner conjugation domain attached to the functionalizing polypeptide after the removal.

In some embodiments, the filter is a polycarbonate filter membrane, and the method further comprises dissolving the polycarbonate filter membrane using dichloromethane after the washing step. In some embodiments, the filter is a polycarbonate filter membrane, and the method further comprises dissolving the polycarbonate filter membrane using dimethylformamide after the washing step. Additional solvents that may be used to dissolve the filter membrane, depending on the material from which the membrane is made, are known in the art. For example, dimethylformamide or chloroform may be used to selectively dissolve the filter membrane and not the curli fibers.

In some embodiments, the filter comprises pores, and wherein the pores are 1 μm to 100 μm in size. In some embodiments, the pore is a circular pore or a mesh-like pore.

In some embodiments, the filter comprises one filter. In some embodiments, the filter comprises at least a first filter and a second filter, arranged in layers. In some embodiments, the first filter comprises a different pore size than the second filter. In some embodiments, the first filter traps a first amyloid fiber that is different than a second amyloid fiber that is trapped by the second filter.

In some embodiments, the microbial culture comprises a bacterial culture, a yeast culture, or a cell lysate.

In some embodiments, the method comprises contacting at least a first composition comprising a first amyloid fiber and a second composition comprising a second amyloid fiber with the filter; and washing the filter; thereby purifying the first amyloid fiber and the second amyloid fiber.

In some embodiments, the purified amyloid fiber is suitable for use in an application selected from the group consisting of: biocatalysis, chemical production, filtration, isolation of molecules from an aqueous solution, water filtration, bioremediation, nanoparticle synthesis, nanowire synthesis, display of optically active materials, surface coating, structural reinforcement of an object, and delivery of a therapeutic agent.

In some embodiments, the purified amyloid fiber is suitable for use as a therapeutic biomaterial, a biological scaffold, a delivery system for therapeutic agents, a biosensor, a biocatalyst, a coating, an electronically-conductive material.

In another aspect, provided herein is a method of producing an amyloid fiber thin film comprising contacting a composition comprising amyloid fibers with a filter membrane; washing the filter membrane; crosslinking the amyloid fibers on the filter membrane using a crosslinking agent, thereby producing crosslinked amyloid fibers; placing a second membrane on top of the crosslinked amyloid fibers, such that the crosslinked amyloid fibers are positioned between the filter membrane and the second membrane, wherein the second membrane is of a different material than the filter membrane; dissolving the filter membrane with a solvent; drying the crosslinked amyloid fibers on the second membrane; and removing the crosslinked amyloid fibers from the second membrane; thereby producing a amyloid fiber thin film.

In some embodiments, the amyloid fiber is selected from the group consisting of a curli fiber, a fiber comprising CsgA, a fiber comprising β-lactoglobulin, a fiber comprising sup-35, a fiber comprising Ure2p, a fiber comprising α-synuclein, a fiber comprising amyloid β-protein (Aβ), a fiber comprising medin, a fiber comprising prolactin, a fiber comprising gelsolin, a fiber comprising calcitonin, a fiber comprising cystatin, a fiber comprising transthyretin, a fiber comprising Pmell 7, and a fiber comprising β2-microglobulin.

In some embodiments, the amyloid fiber thin film comprises a CsgA polypeptide.

In some embodiments, the CsgA polypeptide further comprises a linker and an activity polypeptide, wherein the activity polypeptide is a polypeptide selected from the group consisting of: a conjugation domain, a functionalizing polypeptide, a Histidine tag, a silk protein, a nanobody, a metal binding domain (MBD), a graphene binding (GBP) domain, a carbon nanotube binding (CBP) domain, a gold binding (A3) domain, CT43, FLAG, Z8, E14, QBP1, CLP12, and AFP8; and wherein the linker is attached at one end to the CsgA polypeptide and at the other end to the activity polypeptide.

In some embodiments, the linker is attached to the C-terminus of the CsgA polypeptide or the N-terminus of the CsgA polypeptide.

In some embodiments, the conjugation domain is selected from the group consisting of: SpyTag, EFCA, WRESAI, ARVCF, CaM, SZ21, VMAN11, and DnaEΔC35.

In some embodiments, the conjugation domain is selected from the group consisting of: SpyCatcher, a PDZ domain, Tip1, InaD, M13, SZ16, VMAΔN11, and DnaEC35.

In some embodiments, the CsgA polypeptide is contacted with a partner conjugation domain attached to a functionalizing polypeptide, wherein the partner conjugation domain is selected from the group consisting of SpyCatcher, a PDZ domain, Tip1, InaD, M13, SZ16, VMAΔN11, and DnaEC35.

In some embodiments, the CsgA polypeptide is contacted with a partner conjugation domain attached to a functionalizing polypeptide, wherein the partner conjugation domain is selected from the group consisting of SpyTag, EFCA, WRESAI, ARVCF, CaM, SZ21, VMAN11, and DnaEΔC35.

In some embodiments, the functionalizing polypeptide is an enzyme.

In some embodiments, the activity of the enzyme is maintained after the dissolving step.

In another aspect, provided herein is an amyloid fiber produced using a method described herein.

In another aspect, provided herein is an amyloid fiber thin film produced using a method described herein.

In some embodiments, at least 30 mg of amyloid fiber is purified per liter of microbial culture contacted with the filter. In some embodiments, at least 50 mg of amyloid fiber is purified. In some embodiments, the amyloid fiber is a curli nanofiber.

In yet another aspect, provided herein is a method of purifying an amyloid fiber suitable for use in custom-based fabricated coatings, biocatalysts, and electronically-conductive materials, the method comprising contacting a composition comprising the amyloid fiber with a filter, wherein the composition comprising the amyloid fiber is a microbial culture which has not been lysed prior to the contacting step; and washing the filter; thereby purifying the amyloid fiber suitable for use in custom-based fabricated coatings, biocatalysts, and electronically-conductive materials on the filter.

In another aspect, the invention provides a method of purifying an amyloid fiber from a microbial culture (e.g., a bacterial culture) comprising contacting a composition comprising the amyloid fiber with a filter, wherein the composition comprises a microbial culture which has not been lysed prior to the contacting step; and washing the filter; thereby purifying the amyloid fiber on the filter. As used herein "a microbial culture which has not been lysed" refers to a microbial culture that has not been purposefully manipulated in vitro to lyse the cells in the culture, e.g., by using a lysing reagent (e.g., lysozyme) or by physical disruption of the bacterial cells (e.g., by sonication) prior to being contacted with the filter.

In some embodiments, the method further comprises contacting the filter with a solubilization agent. In some embodiments, the method further comprises contacting the filter with a DNAse. In some embodiments, the method further comprises contacting the filter with a RNAse. In some embodiments, the method further comprises contacting the filter with a surfactant. In some embodiments, the method further comprises contacting the filter with a soubilization agent and a DNAse. In some embodiments, the method further comprises contacting the filter with a solubilization agent and an RNAse. In some embodiments, the method further comprises contacting the filter with a solubilization agent and a surfactant. In some embodiments, the method further comprises contacting the filter with a DNAse and an RNAse. In some embodiments, the method further comprises contacting the filter with a DNAse and a surfactant. In some embodiments, the method further comprises contacting the filter with an RNAse and a surfactant. In one embodiment, the method further comprises removing the amyloid fiber from the filter, thereby creating a free-standing amyloid fiber. In one embodiment, the method further comprises removing the amyloid fiber from the filter, thereby creating a free-standing thin film.

In one embodiment, the filter is washed sequentially with a solubilization agent, a DNAse and an RNAse, and a surfactant. However, the order of wash steps can be re-ordered. As a non-limiting example, in one embodiment, the filter is washed sequentially with a soubilization agent, a surfactant, and a DNAse and an RNAse.

In some embodiments, the solubilization agent is selected from the group consisting of guanidine HCl (also known as guanidinium hydrochloride), urea, dimethyl sulfoxide (DMSO), sodium dodecyl sulfate (SDS), beta-mercaptoethanol, and n-propanol.

In some embodiments, the surfactant is selected from the group consisting of SDS, 4-octylphenol polyethoxylate (also known as Triton X-100™), polyethylene glycol sorbitan monolaurate (also known as Tween® 20), polyethylene glycol sorbitan monooleate (also known as Tween® 80).

In one embodiment, the amyloid fiber is selected from the group consisting of a curli fiber, a fiber comprising CsgA, a fiber comprising β-lactoglobulin, a fiber comprising sup-35, a fiber comprising Ure2p, a fiber comprising α-synuclein, a fiber comprising amyloid β-protein (Aβ), a fiber comprising medin, a fiber comprising prolactin, a fiber comprising gelsolin, a fiber comprising calcitonin, a fiber comprising cystatin, a fiber comprising transthyretin, a fiber comprising Pmell 7, and a fiber comprising β2-microglobulin.

In one embodiment, the curli fiber comprises a CsgA polypeptide. In one embodiment, the curli fiber comprises a CsgA polypeptide fused to another polypeptide. In one embodiment, the curli fiber comprises a CsgA polypeptide that is fused to another polypeptide that is not normally associated with CsgA in nature.

In one embodiment, the CsgA polypeptide further comprises a linker and an activity polypeptide, wherein the activity polypeptide is a polypeptide selected from the group consisting of: a conjugation domain, a functionalizing polypeptide, a Histidine tag, a silk protein, a nanobody, a metal binding domain (MBD), a graphene binding (GBP) domain, a carbon nanotube binding (CBP) domain, a gold binding (A3) domain, CT43, FLAG, Z8, E14, QBP1, CLP12, and AFP8; and wherein the linker is attached at one end to the CsgA polypeptide and at the other end to the activity polypeptide. In one embodiment, the linker is attached to the C-terminus of the CsgA polypeptide or the N-terminus of the CsgA polypeptide.

In one embodiment, the conjugation domain is selected from the group consisting of: SpyTag, EFCA, WRESAI, ARVCF, CaM, SZ21, VMAN11, and DnaEΔC35. In one embodiment, the conjugation domain is selected from the group consisting of: SpyCatcher, a PDZ domain, Tip1, InaD, M13, SZ16, VMAΔN11, and DnaEC35. In one embodiment, the CsgA polypeptide is contacted with a partner conjugation domain attached to a functionalizing polypeptide, wherein the partner conjugation domain is selected from the group consisting of SpyCatcher, a PDZ domain, Tip1, InaD, M13, SZ16, VMAΔN11, and DnaEC35. In one embodiment, the CsgA polypeptide is contacted with a partner conjugation domain attached to a functionalizing polypeptide, wherein the partner conjugation domain is selected from the group consisting of SpyTag, EFCA, WRESAI, ARVCF, CaM, SZ21, VMAN11, and DnaEΔC35.

In one embodiment, the CsgA polypeptide and the partner conjugation domain are contacted on the filter before the washing or after the washing.

In one embodiment, the functionalizing protein is an enzyme or a metal binding domain.

In one embodiment, the method also purifies a component of the extracellular matrix of bacteria or a filamentous protein structure; wherein the component is cellulose, a flagella, a *Geobacter* pili, a bacterial nanowire, or a *Shewanella* nanowire; or wherein the filamentous protein structure is a filamentous bacteriophage, a M13 bacteriophage, a recombinant protein fiber, silk, collagen, or a fiber-like structure.

In one embodiment, an engineered microbial cell produces the amyloid fiber. In one embodiment, the method further comprises expressing the amyloid fiber from an engineered microbial cell before the contacting step. In one embodiment, the engineered microbial cell is a bacterium or a fungi. In one embodiment, the bacterium or fungi is selected from the group consisting of *E. coli, Salmonella*, or yeast (e.g., *Saccharomyces cerevisiae* or *Schizosaccharomyces pombe*). In one embodiment, the bacterium is a genetically engineered *E. coli* which comprises a csgBACEFG operon. In one embodiment, the bacterium is a genetically engineered *E. coli* which comprises a csgACEFG operon. In some embodiments, the bacterium is an *E. coli* strain comprising a deletion in an endogenous csgB gene. In some embodiments, the bacterium is *E. coli* strain comprising a deletion in an endogenous csgD gene.

In one embodiment, the filter is a filter membrane, a mesh, a cloth (e.g., a porous cloth), or a textile. In one embodiment, the filter membrane is a polycarbonate, nylon, cellulose, polytetrafluoroethylene (Teflon™), polyethersulfone, polyvinylidene fluoride, or polyvinyidene chloride filter. In one embodiment, the filter membrane is a polycarbonate membrane. In one embodiment, the mesh is a metal mesh, a glass mesh, a ceramic mesh, a plastic mesh, or a polymer mesh. In some embodiments, the cloth is a cotton cloth (e.g., a thin cotton cloth or a thick cotton cloth). In one embodiment, the amyloid fiber is removed from the filter after washing. In one embodiment, the amyloid fiber is removed from the filter after washing, and the CsgA polypeptide is contacted with the partner conjugation domain attached to the functionalizing polypeptide after the removal. In one embodiment, the filter is a polycarbonate filter membrane, and the polycarbonate filter membrane is dissolved using dichloromethane after the washing step, thereby purifying the amyloid fiber. In one embodiment, the filter is a polycarbonate filter membrane, and the polycarbonate filter membrane is dissolved using dimethylformamide after the washing step, thereby purifying the amyloid fiber.

In one embodiment, the filter comprises pores, and wherein the pores are 1 μm to 100 μm in size. In one embodiment, the pore is a circular pore or a mesh-like pore.

In one embodiment, the filter comprises one filter. In one embodiment, the filter comprises at least a first filter and a second filter, arranged in layers. In one embodiment, the first filter comprises a different pore size than the second filter. In one embodiment, the first filter traps a first amyloid fiber that is different than a second amyloid fiber that is trapped by the second filter.

In one embodiment, the composition comprising the amyloid fiber that is being purified comprises a bacterial culture, a yeast culture, a cell lysate, a mixture of proteins comprising an amyloid fiber, etc.

In one embodiment, the method comprises contacting at least a first composition comprising a first amyloid fiber and a second composition comprising a second amyloid fiber with the filter; and washing the filter; thereby purifying the first amyloid fiber and the second amyloid fiber.

In one aspect, the invention provides a method of producing an amyloid fiber thin film comprising contacting a composition comprising amyloid fibers with a filter membrane; washing the filter membrane; crosslinking the amyloid fibers on the filter membrane using a crosslinking agent, thereby producing crosslinked amyloid fibers; placing a second membrane on top of the crosslinked amyloid fibers, such that the crosslinked amyloid fibers are positioned between the filter membrane and the second membrane, wherein the second membrane is of a different material than the filter membrane; dissolving the filter membrane with a solvent; drying the crosslinked amyloid fibers on the second membrane; and removing the crosslinked amyloid fibers from the second membrane; thereby producing a amyloid fiber thin film. In another aspect, the invention provides a method of producing an amyloid fiber thin film comprising contacting a composition comprising amyloid fibers with a polycarbonate filter membrane; washing the polycarbonate filter membrane; crosslinking the amyloid fibers on the polycarbonate filter membrane using a crosslinking agent, thereby producing crosslinked amyloid fibers; placing a Teflon™ membrane on top of the crosslinked amyloid fibers, such that the crosslinked amyloid fibers are positioned between the Teflon™ membrane and the polycarbonate membrane; dissolving the polycarbonate membrane with dichloromethane (DCM); drying the crosslinked amyloid fibers on the Teflon™ membrane; and removing the crosslinked amyloid fibers from the Teflon™ membrane; thereby producing a amyloid fiber thin film.

In one embodiment, the method further comprises removing the amyloid fiber from the filter, thereby creating a free-standing amyloid fiber. In one embodiment, the method further comprises removing the amyloid fiber from the filter, thereby creating a free-standing amyloid fiber thin film.

In one embodiment, the amyloid fiber is selected from the group consisting of a curli fiber, a fiber comprising CsgA, a fiber comprising β-lactoglobulin, a fiber comprising sup-35, a fiber comprising Ure2p, a fiber comprising α-synuclein, a fiber comprising amyloid β-protein (Aβ), a fiber comprising medin, a fiber comprising prolactin, a fiber comprising gelsolin, a fiber comprising calcitonin, a fiber comprising cystatin, a fiber comprising transthyretin, a fiber comprising Pmel17, and a fiber comprising β2-microglobulin.

In one embodiment, the curli fiber comprises a CsgA polypeptide. In one embodiment, the CsgA polypeptide further comprises a linker and an activity polypeptide, wherein the activity polypeptide is a polypeptide selected from the group consisting of: a conjugation domain, a functionalizing polypeptide, a Histidine tag, a silk protein, a nanobody, a metal binding domain (MBD), a graphene binding (GBP) domain, a carbon nanotube binding (CBP) domain, a gold binding (A3) domain, CT43, FLAG, Z8, E14, QBP1, CLP12, and AFP8; and wherein the linker is attached at one end to the CsgA polypeptide and at the other end to the activity polypeptide. In one embodiment, the linker is attached to the C-terminus of the CsgA polypeptide or the N-terminus of the CsgA polypeptide.

In one embodiment, the conjugation domain is selected from the group consisting of: SpyTag, EFCA, WRESAI, ARVCF, CaM, SZ21, VMAN11, and DnaEΔC35. In one embodiment, the conjugation domain is selected from the group consisting of: SpyCatcher, a PDZ domain, Tip1, InaD, M13, SZ16, VMAΔN11, and DnaEC35. In one embodiment, the CsgA polypeptide is contacted with a partner conjugation domain attached to a functionalizing polypeptide, wherein the partner conjugation domain is selected from the group consisting of SpyCatcher, a PDZ domain, Tip1, InaD, M13, SZ16, VMAΔN11, and DnaEC35. In one embodiment, the CsgA polypeptide is contacted with a partner conjugation domain attached to a functionalizing polypeptide, wherein the partner conjugation domain is selected from the group consisting of SpyTag, EFCA, WRESAI, ARVCF, CaM, SZ21, VMAN11, and DnaEΔC35.

In one embodiment, the functionalizing protein is an enzyme or a metal binding domain. In one embodiment, the activity of the enzyme is maintained after the dissolving step.

In one aspect, the invention provides a method of recycling purified curli fibers, comprising dissolving purified curli fibers in a solution; dropcasting the solution comprising the dissolved curli fibers onto a substrate; and drying the substrate, thereby recycling the purified curli nanofibers. In another aspect, the invention provides a method of recycling purified curli fibers, comprising dissolving purified curli fibers in a solution; dropcasting the solution comprising the dissolved curli fibers onto an oxygen plasma-treated substrate; and drying the substrate, thereby recycling the purified curli nanofibers.

In one embodiment, the amyloid fiber is selected from the group consisting of a curli fiber, a fiber comprising CsgA, a fiber comprising β-lactoglobulin, a fiber comprising sup-35, a fiber comprising Ure2p, a fiber comprising α-synuclein, a fiber comprising amyloid β-protein (Aβ), a fiber comprising medin, a fiber comprising prolactin, a fiber comprising gelsolin, a fiber comprising calcitonin, a fiber comprising cystatin, a fiber comprising transthyretin, a fiber comprising Pmell 7, and a fiber comprising β2-microglobulin.

In one embodiment, the curli fiber comprises a CsgA polypeptide. In one embodiment, the CsgA polypeptide further comprises a linker and an activity polypeptide, wherein the activity polypeptide is a polypeptide selected from the group consisting of: a conjugation domain, a functionalizing polypeptide, a Histidine tag, a silk protein, a nanobody, a metal binding domain (MBD), a graphene binding (GBP) domain, a carbon nanotube binding (CBP) domain, a gold binding (A3) domain, CT43, FLAG, Z8, E14, QBP1, CLP12, and AFP8; and wherein the linker is attached at one end to the CsgA polypeptide and at the other end to the activity polypeptide. In one embodiment, the linker is attached to the C-terminus of the CsgA polypeptide or the N-terminus of the CsgA polypeptide.

In one embodiment, the conjugation domain is selected from the group consisting of: SpyTag, EFCA, WRESAI, ARVCF, CaM, SZ21, VMAN11, and DnaEΔC35. In one embodiment, the conjugation domain is selected from the group consisting of: SpyCatcher, a PDZ domain, Tip1, InaD, M13, SZ16, VMAΔN11, and DnaEC35. In one embodiment, the CsgA polypeptide is contacted with a partner conjugation domain attached to a functionalizing polypeptide, wherein the partner conjugation domain is selected from the group consisting of SpyCatcher, a PDZ domain, Tip1, InaD, M13, SZ16, VMAΔN11, and DnaEC35. In one embodiment, the CsgA polypeptide is contacted with a partner conjugation domain attached to a functionalizing polypeptide, wherein the partner conjugation domain is selected from the group consisting of SpyTag, EFCA, WRESAI, ARVCF, CaM, SZ21, VMAN11, and DnaEΔC35.

In one embodiment, the functionalizing protein is an enzyme or a metal binding domain.

In one aspect, the invention provides an amyloid fiber produced by any of the methods described herein. In one aspect, the invention provides an amyloid fiber thin film produced by any of the methods described herein. In one embodiment, the invention provides a curli fiber produced by any of the methods described herein.

In one embodiment, at least 30 mg of amyloid fiber is purified per liter of microbial culture contacted with the filter. In one embodiment, at least 50 mg of amyloid fiber is purified. In one embodiment, the amyloid fiber is a curli nanofiber.

BRIEF DESCRIPTION OF THE FIGURES

FIG. 1A depicts the morphological differences between filtered bacterial cultures producing CsgA expressed along with (top) or without (bottom) CsgB, visualized with SEM prior to any purification. FIG. 1B depicts a schematic of the filtration purification process to trap large curli nanofiber aggregates on filter membranes and remove any impurities or cell debris via filtration. SEM images of large purified curli aggregates on a 10 µm polycarbonate membrane are shown.

FIG. 2A shows that several final washing steps (NaOH, HCl, SDS, formic acid) result in varying CsgA purities. The GdmCl wash was fixed at 8 M. SDS was selected for further experiments because it best facilitated removal of fibers from the membrane. FIG. 2B shows curli nanofiber purity as a function of GdmCl concentration used for the on-filter incubation step. FIG. 2C shows that further purification of isolated curli fibers by dialysis in a 6-8 kDa MWCO membrane led to removal of some low MW impurities (black box). CsgA-HisTag appears at its expected molecular weight of 16.7 kDa. FIG. 2D depicts curli nanofibers, composed of CsgA-HisTag and purified by filtration, visualized with SDS-PAGE/Coomassie (left) and detected by Western blot (right) using an anti-His antibody.

FIG. 3A shows Congo Red staining of membranes after filtration of the bacterial cultures, without additional treatment (top) and with full treatment with GdmCl, nuclease and SDS (bottom) for bacteria producing wild-type curli fibers (CsgA) or MBP as a negative control. FIG. 3B shows that after the SDS treatment, filtered curli fibers can easily be scraped off of the filters to obtain semi-pure protein.

FIG. 4A. shows that GdmCl effectively removes cells from the curli fibers, leaving behind voids where cells used to be (black arrows). The aggregation state of the fibers also appears to be affected. 10 µm pores of the membrane are also indicated (white arrows). FIG. 4B shows that SDS treatment after cell removal causes the film to wrinkle (black dashed arrows) and makes removal straightforward from the membrane surface.

FIG. 5A depicts His-tagged curli nanofibers visualized with SDS-PAGE (left) and detected by Western blot (right) using an anti-his antibody, after filtration purification and removal from the filter. FIG. 5B shows that CsgA-SpyTag fusions can bind fluorescent Venus-SpyCatcher proteins after purification, as visualized by Venus fluorescence on the filter, but controls cannot. FIG. 5C shows that CsgA-SpyCatcher fusions can bind fluorescent Venus-SpyTag proteins after purification, as visualized by Venus fluorescence on the filters, but controls cannot.

FIG. 6A shows that a Teflon™ membrane is placed on top of the filtered curli fibers (1), and the sandwiched fibers are immersed in DCM (2). Within seconds, the polycarbonate membrane is dissolved and the curli film begins to float (3). The Teflon™ membrane is used to collect the floating film (4). The curli film is dried on the Teflon™ membrane (5), after which it can be peeled off (6) to yield an intact macroscopic thin film composed of assembled curli fibers (7). FIG. 6B shows that the thin films are transparent. FIG. 6C shows that the thin films are flexible. FIG. 6D shows that the thin films display functional peptide tags that remain active throughout the process. Free-standing films, composed of either CsgA-His or CsgA-SpyTag were exposed to Venus-SpyCatcher, washed, and visualized with fluorescence. FIG. 6E depicts SEM of dried, free-standing curli thin films. The pore pattern of the filter membrane is reproduced in the film, with extrusions (white arrows) where portions of the film were sucked through the filter pore. FIG. 6F shows FTIR analyses of the amide I of crosslinked films compared to that of scraped CsgA powder (solid lines). Spectra were reconstituted by a linear sum of two amide-related peaks: indicative of the presence of β-sheets (indicated with "*") and disordered or aggregated structures (indicated with "**").

FIG. 7A shows that curli fibers scraped from filter membranes (1) and dried (2) are disassembled using HFIP/TFA, producing a clear solution (3). The solution can be dropcast onto various substrates (4) including silicon (left) and glass (right, after Congo Red staining) to form thin films. After rinsing with SDS, the curli fiber film delaminates from the substrate to form a flexible free-standing film (5), which can then be recycled by disassembling the fibers again with HFIP/TFA to fabricate a new curli-based material. Substrates shown have 1 cm by 1 cm dimensions. FIG. 7B shows that thin curli films formed by dropcasting a 15 mg/mL solution of curli in HFIP and TFA are fibrous and porous, as visualized by SEM. The cross-section of the film is shown (left) and a higher magnification image (right) allows for fiber visualization.

FIGS. 9A and 9B depict the detection of curli fibers and nucleic acids for purified curli fibers. FIG. 9A shows filter membranes stained with ThT (curli fibers stained). FIG. 9B shows filter membranes stained with SYTO 59 Red Fluorescent Nucleic Acid Stain (DNA and RNA stained) for filter membranes treated or not with nuclease Benzonase®. Images have 600 μm by 600 μm dimensions.

FIG. 11A depicts a 142 mm diameter filter membrane with curli nanofibers deposited, and spatula used for scraping off the fibers from the membrane. FIG. 11B depicts lyophilized curli nanofibers collected from a total of 100 mL of culture.

FIG. 12A shows that various solvents were used to dissolve filter membranes with Congo Red-stained curli films (left vial), or bare filter membranes (right vial). FIG. 12B shows the discoloration of curli fibers after overnight incubation in dimethylformamide.

FIG. 14 is illustrative only, providing an example of CsgA polypeptides are that linked to SpyCatcher conjugation domains that bind to SpyTag partner conjugation domains attached to Venus.

DETAILED DESCRIPTION

Definitions

Figure 1A:
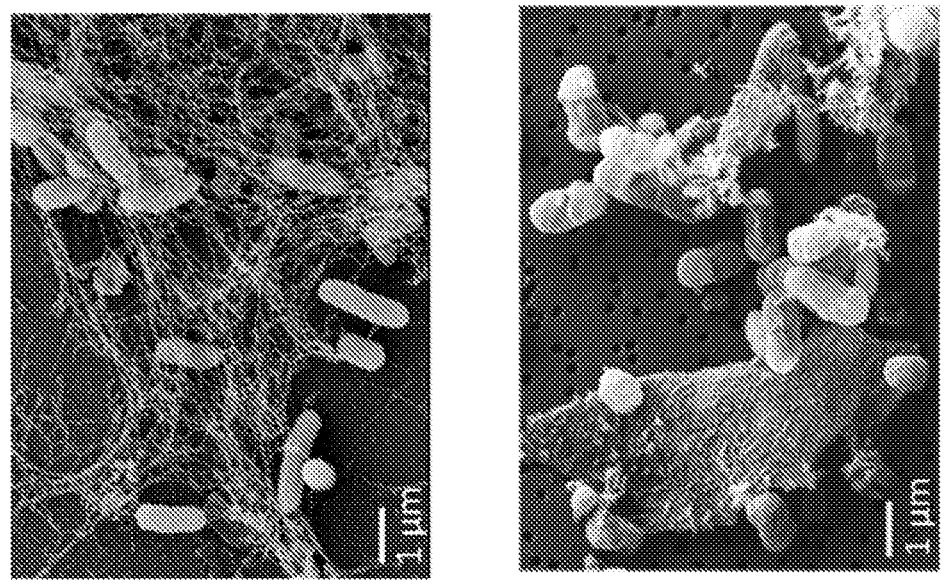
FIGS. 1A and 1B show that size-dependent separation of curli nanofibers is possible due to the formation of large curli aggregates in the absence of the curli nucleator protein CsgB.
Figure 1A:
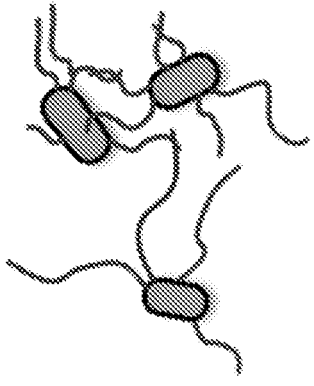
Figure 1A:
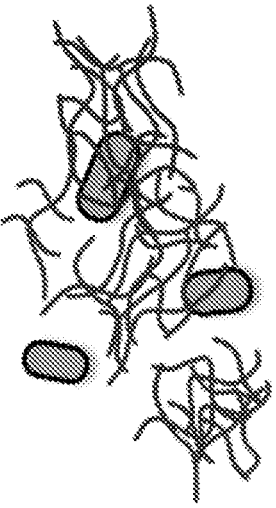
Figure 1B:
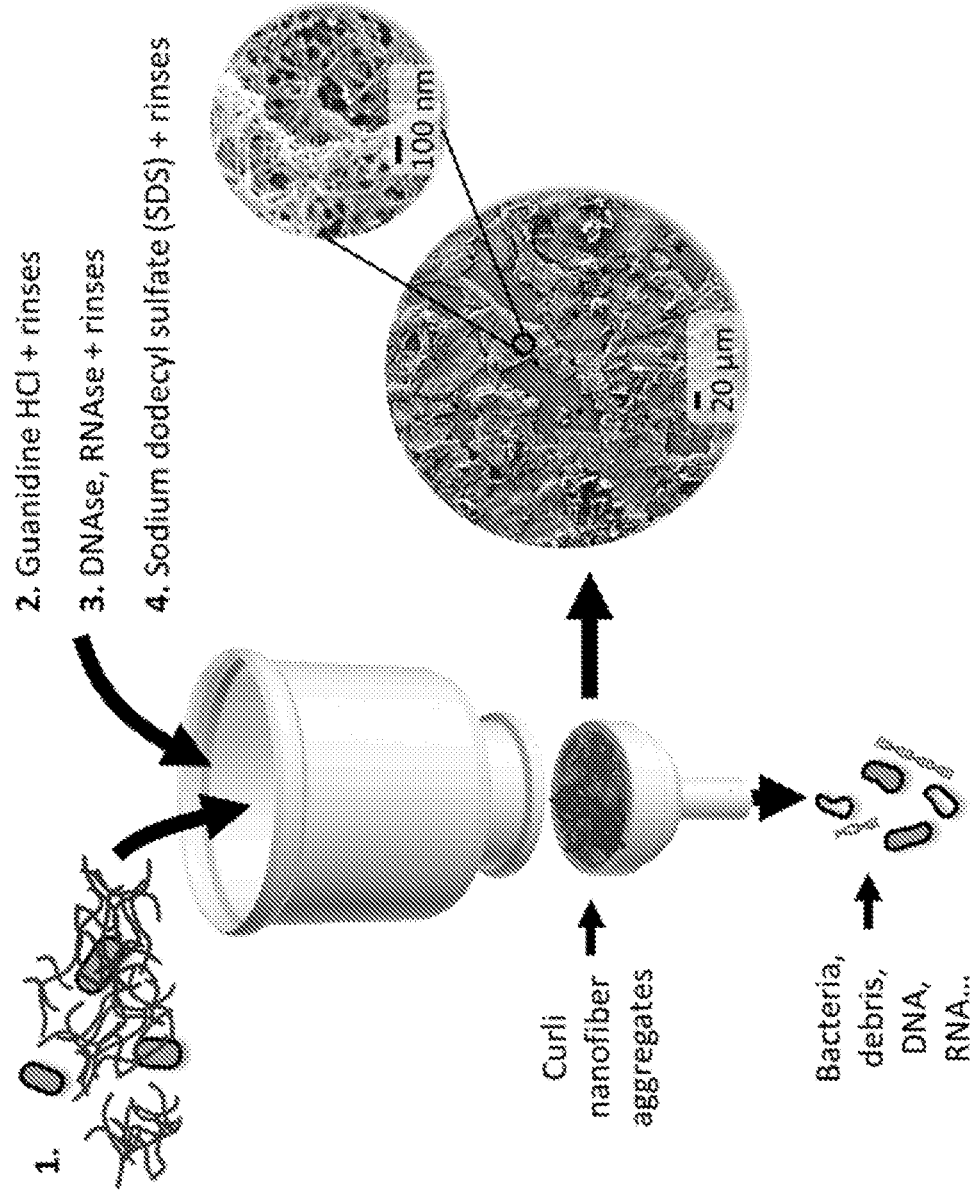

In order that the present invention may be more readily understood, certain term are first defined.

As used herein, the term "amyloid fiber" refers to a primary proteinaceous structural component. Amyloid fibers comprise, but are not limited to, curli fibers, or fibers composed of CsgA, β-lactoglobulin, sup-35, Ure2p, α-synuclein, amyloid β-protein (Aβ), medin, prolactin, gelsolin, calcitonin, cystatin, transthyretin, Pmell 7, and β2-microglobulin As used herein, the term "curli fiber" refers to the primary proteinaceous structural component of E. coli biofilms. Curli fibers are highly robust functional amyloid nanofibers with a diameter of ~4-7 nm that exist as extended tangled networks encapsulating the cells. Curli fibers are formed from the extracellular self-assembly of CsgA, a small secreted 13-kDa protein As used herein, "CsgA" refers to the major structural subunit of the curli fiber. The sequences of CsgA and its homologs are known in a number of species. For example, the sequence of E. coli CsgA is known (NCBI Gene ID NO: 949055; (polypeptide)). CsgA polypeptide (NCBI Ref Seq: NP_415560): mkllkvaaiaaivfsgsalagvvpqyggggnhgggg-nnsgpnselniyqygggnsalalqtdarnsdltitqhgggngadvgqg sddssidltqrgfgnsatldqwngknsemtvkqfgggngaavdq-
tasnssvnvtqvgfgnnatahqy (SEQ ID NO:1).

A CsgA protein may include naturally occurring mutations or variants of CsgA, homologs of CsgA, or engineered mutations or variants of CsgA. In some embodiments, "CsgA" refers to E. coli CsgA. In some embodiments, "CsgA" refers to a polypeptide having at least 80% homology to SEQ ID NO:1 (e.g., 80% or greater homology, 90% or greater homology, or 95% or greater homology).

As used herein, the term "curli nanofibers" or "curli nanofiber aggregates" are used interchangeably to refer to curli fibers that do not contain CsgB polypeptides. A "curli nanofiber" or "curli nanofiber aggregate" may be produced by a bacterium engineered to produce curli fibers without CsgB, or it can be a curli fibers that have had CsgB polypeptides removed during or after curli formation. Curli nanofibers can be naturally occurring (but have the CsgB removed), or genetically engineered.

The terms "protein" and "polypeptide" are used interchangeably herein to designate a series of amino acid residues, connected to each other by peptide bonds between the alpha-amino and carboxy groups of adjacent residues. The terms "protein," and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the term "gene" refers to a nucleic acid fragment that encodes a protein or fragment thereof, optionally including regulatory sequences preceding (5' non-coding sequences) and following (3' non-coding sequences) the coding sequence. In one embodiment, a "gene" does not include regulatory sequences preceding and following the coding sequence. Each gene may be present on a plasmid or bacterial chromosome. In addition, multiple copies of any gene may be present in the bacterium, wherein one or more copies of the gene may be altered as described herein.

A "native gene" refers to a gene as found in nature, optionally with its own regulatory sequences preceding and following the coding sequence. A "chimeric gene" refers to any gene that is not a native gene, optionally comprising regulatory sequences preceding and following the coding sequence, wherein the coding sequences and/or the regulatory sequences, in whole or in part, are not found together in nature. Thus, a chimeric gene may comprise regulatory sequences and coding sequences that are derived from different sources, or regulatory and coding sequences that are derived from the same source, but arranged differently than is found in nature.

As used herein, the term "endogenous gene" refers to a native gene in its natural location in the genome of an organism.

As used herein, a "heterologous" gene or "heterologous sequence" refers to a nucleotide sequence that is not normally found in a given cell in nature. As used herein, a heterologous sequence encompasses a nucleic acid sequence that is exogenously introduced into a given cell. "Heterologous gene" includes a native gene, or fragment thereof, that has been introduced into the host cell in a form that is different from the corresponding native gene. For example, a heterologous gene may include a native coding sequence that is a portion of a chimeric gene to include a native coding sequence that is a portion of a chimeric gene to include non-native regulatory regions that is reintroduced into the host cell. A heterologous gene may also include a native gene, or fragment thereof, introduced into a non-native host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature.

As used herein, the term "expression" refers to the transcription and stable accumulation of sense (mRNA) or anti-sense RNA derived from a nucleic acid, and/or to translation of an mRNA into a polypeptide.

As used herein, the term "plasmid" or "vector" refers to an extrachromosomal nucleic acid, e.g., DNA, construct that is not integrated into a bacterial cell's genome. Plasmids are usually circular and capable of autonomous replication. Plasmids may be low-copy, medium-copy, or high-copy, as is well known in the art. Plasmids may optionally comprise a selectable marker, such as an antibiotic resistance gene, which helps select for bacterial cells containing the plasmid and which ensures that the plasmid is retained in the bacterial cell. A plasmid may comprise a nucleic acid sequence encoding a heterologous gene or gene cassette.

As used herein, the term "transform" or "transformation" refers to the transfer of a nucleic acid fragment into a host bacterial cell, resulting in genetically-stable inheritance. Host bacterial cells comprising the transformed nucleic acid fragment are referred to as "recombinant" or "transgenic" or "transformed" organisms.

As used herein, the term "engineered microbial cell" or "engineered bacterial cell" refers to a bacterial cell or bacteria that have been genetically modified from their native state. For instance, an engineered bacterial cell may have nucleotide insertions, nucleotide deletions, nucleotide rearrangements, and nucleotide modifications introduced into their DNA. These genetic modifications may be present in the chromosome of the bacteria or bacterial cell, or on a plasmid in the bacteria or bacterial cell. Engineered bacterial cells disclosed herein may comprise exogenous nucleotide sequences on plasmids. Alternatively, engineered bacterial cells may comprise exogenous nucleotide sequences stably incorporated into their chromosome.

As used herein, a "CsgA fusion" or an "engineered CsgA polypeptide" refers to a CsgA polypeptide comprising an activity polypeptide attached to the CsgA at either the C-terminus or the N terminus or both, but without interrupting the sequence of the CsgA polypeptide. In one aspect, a CsgA fusion self-assembles into a curli fiber and is used to capture and immobilize a functionalizing polypeptide which comprises a partner conjugation domain.

As used herein, the term "fusion" or "protein fusion" refers to a chimeric protein created through the joining of two or more genes that originally encoded separate proteins. A protein fusion is created artificially using recombinant DNA technology. Disclosed herein are CsgA proteins fused, or linked, to conjugation domains. Also disclosed herein are functionalizing polypeptides fused, or linked, to partner conjugation domains.

As used herein, the term "bound to" refers to an interaction between to molecules or proteins. A protein may be covalently or non-covalently bound to another protein or molecule. As used herein, a "covalent bond" refers to a chemical bond that involves the sharing of electron pairs between atoms. In contrast, a "non-covalent bond" does not involve the sharing of electrons, but involves more dispersed variations of electromagnetic interactions between molecules. Non-covalent bonds include, but are not limited to, electrostatic, van der Walls forces, and hydrophobic effects.

As used herein, the term "activity polypeptide" refers to a polypeptide having an activity or function, such that when it is present on a curli nanofiber, it confers upon the curli nanofiber a property, function, or activity which it did not have in the absence of the activity of the polypeptide. Accordingly, an activity polypeptide can be, e.g., an enzyme, a polypeptide that binds another molecule (e.g., a metal), a binding domain, a peptide that is bound by another molecule (e.g., a ligand or epitope), or the like. Examples of polypeptides for use as activity polypeptides include, but are not limited to, Metal binding domain (MBD); SpyTag; SpyCatcher, a silk protein, a nanobody, graphene binding (GBP) domain; carbon nanotube binding (CBP) domain; gold binding (A3) domain; CT43; FLAG; Z8; E14; QBP1; CLP12; and AFP8.

As used herein, the term "conjugation domain" refers to a polypeptide that can specifically bind to a partner conjugation domain. A conjugation domain may bind to a partner conjugation domain covalently or non-covalently. A conjugation domain can be, e.g., about 100 amino acids or less in size, about 75 amino acids or less in size, about 50 amino acids or less in size, about 40 amino acids or less in size or smaller. Conjugation domains described herein are linked, or fused, to a CsgA protein. Examples of conjugation domains are well known in the art and are described in more detail, below.

As used herein, the term "partner conjugation domain" refers to a polypeptide that can specifically bind to a conjugation domain. A partner conjugation domain may bind to a conjugation domain covalently or non-covalently and may be about the same size as the conjugation domain or larger. For example, a partner conjugation domain can be about 4000 amino acids or less in size, about 3000 amino acids or less in size, about 2000 amino acids or less in size, about 1000 amino acids or less in size, about 500 amino acids or less in size, about 200 amino acids or less in size, about 100 amino acids or less in size, about 75 amino acids or less in size, about 50 amino acids or less in size, about 40 amino acids or less in size, or smaller. Partner conjugation domains described herein are linked, or fused, to a functionalizing polypeptide. Examples of conjugation domains are well known in the art and are described in more detail, below.

As used herein, the term "functionalizing polypeptide" refers to a polypeptide having an activity or function, such that when it is present on a curli fiber and/or in a biofilm, it confers upon the curli fiber and/or biofilm a property, function, or activity which it did not have in the absence of the polypeptide. Such functions include catalytic function, recognition function, or structural function. A functionalizing polypeptide can be of any size and include, e.g., an enzyme, a polypeptide that binds another molecule, a polypeptide that binds a metal, an antibody, a therapeutic agent, a diagnostic agent, a metal, an antimicrobial agent, an anti-inflammatory agent, or an anticancer agent. Examples of polypeptides for use as functionalizing polypeptides include, but are not limited to, an enzyme, a silk protein, a nanobody, a metal binding domain (MBD), a graphene binding (GBP) domain, a carbon nanotube binding (CBP) domain, a gold binding (A3) domain, CT43, FLAG, Z8, E14, QBP1, CLP12, and AFP8.

As used herein, the term "filter" refers to a surface used to trap curli nanofiber aggregates while allowing microbes or microbial cells, nucleic acids, and proteins that are not expressed as part of the curli fiber or are otherwise attached to the curli fiber to flow through the surface, thereby purifying or isolating the curli nanofiber aggregates. A filter can be, for example, a filter membrane, a mesh, a cloth, a textile or other fabric having pores of a size capable of purifying or isolating amyloid fibers, e.g., curli fibers.

As used herein, the term "filtration" or "filtering" refers to the process of purifying curli nanofiber aggregates away from microbes or microbial cells, such as bacteria or viruses, nucleic acids, such as DNA or RNA, and proteins that are not expressed as part of the curli fiber or are otherwise attached to the curli fiber, using a filter. As used herein, the term filtration includes processes mediated by, but not limited to, vacuum filtration, centrifugal filtration, positive pressure filtration, electrophoresis through a membrane, use of high-energy acoustics for shifting materials through a filter or membrane, and belt press filtration.

As used herein, the term "thin film" or "nanofiber film" refers to one or more layers of amyloid nanofibers, e.g., curli fibers, that form a film. A thin film can be removed from a purification filter so that it is free-standing, or it can be applied to the surface of a substrate. A "free-standing film" refers to a film that is capable of supporting its own weight, e.g., after removal from a filter. A thin film can be completely free of microbes, such as bacteria, or can include microbes, such as bacteria.

As used herein, the term "biofilm matrix" or "biofilm extracellular matrix" refers to a matrix of extracellular polymeric substances, including, but not limited to extracellular DNA, proteins, glycopeptides, and polysaccharides, which was produced by a mass of microorganisms, such as bacteria, but wherein the microorganisms have been completely or almost completely killed or removed. Accordingly, in one embodiment, a "biofilm matrix" does not comprise any microorganisms, such as bacteria. In one embodiment, a "biofilm matrix" does not comprise any live microorganisms, such as bacteria.

As used herein, the term "biofilm" refers to a matrix of extracellular polymeric substances, including, but not limited to extracellular DNA, proteins, glycopeptides, and polysaccharides, which are produced by a mass of microorganisms, such as bacteria. In one embodiment, a biofilm comprises a biofilm matrix and bacteria. In one embodiment, the bacteria are live bacteria.

As used herein, the term "crosslinking agent" refers to a substance that is able to form chemical linkages between two polymers (e.g., two polypeptides) or two different regions of the same polymer (e.g., two regions of one protein).

As used herein, the term "enzyme" refers to a polypeptide that can act as a catalyst to accelerate or catalyze a chemical reaction. As used herein, the term "enzymatic cascade" refers to two or more polypeptides which are involved in a series of successive chemical reactions.

As used herein, the term "surfactant" refers to a natural or synthetic amphiphilic compound. In some embodiments, the surfactant is non-ionic. In some embodiments, the surfactant is zwitterionic. In some embodiments, the surfactant is ionic. Exemplary surfactants include, but are not limited to, SDS, 4-octylphenol polyethoxylate, polyethylene glycol sorbitan monolaurate, and polyethylene glycol sorbitan monooleate.

As used herein, the term "solvent" generally refers to a liquid capable of holding a substance in solution.

The term "recycle" or "recycling" refers to the process of disassembling or breaking down a curli nanofiber or curli nanofiber film, and then reassembling the curli nanofiber or curli nanofiber film. For example, a curli nanofiber may be disassembled into CsgA polypeptides in solution and then the CsgA polypeptides can be reassembled into a curli nanofiber in solution or on the surface of a substrate.

The term "textile" refers to a cloth or composition produced, e.g., by weaving, knitting, or felting. A textile may comprise natural or synthetic fibers.

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Microorganisms

The methods of the present disclosure may be used to purify amyloid fibers produced by microorganisms. In exemplary embodiments, curli nanofibers are produced by bacteria and purified using the methods of the present disclosure. However, the filtration purification methods of the present disclosure may also be used to purify fibrous materials or amyloids, such as curli fibers, away from cultures of microorganisms, such as bacteria, yeast or other fungi, bacteriophages, cell lysates, or mixtures of proteins comprising curli fibers.

Any bacteria that can be used to produce protein fibers or amyloids are suitable for use with the methods of the present disclosure. In some embodiments, the filtration purification methods of the present invention are used to purify amyloid fibers produced by a bacterium of the family Enterobacteriaceae. In exemplary embodiments, the filtration purification methods of the present invention are used to purify amyloid fibers produced by $E.$ $coli$. In other embodiments, the filtration purification methods of the present invention are used to purify amyloid fibers produced by $Salmonella$ spp.

The methods of the present disclosure may be used to purify components of the extracellular matrix of bacteria. In exemplary embodiments, the methods can be used to purify any type of amyloid fiber by filtration, including, but not limited to curli fibers, or fibers composed of CsgA, β-lactoglobulin, sup-35, Ure2p, α-synuclein, amyloid β-protein (Aβ), medin, prolactin, gelsolin, calcitonin, cystatin, transthyretin, Pmel1 7, β2-microglobulin. The methods of the present disclosure may also be used to purify other components of bacterial extracellular matrix, including, but not limited to, cellulose, flagella, a pili (e.g., $Geobacter$ pili, a bacterial nanowire (e.g., a $Shewanella$ nanowire), or any nanowire-like or fiber-like structure.

The methods of the present disclosure can be used to purify a variety of protein structures that are not necessarily part of an extracellular matrix of bacteria, including, for example, filamentous bacteriophage, such as M13 bacteriophage, or recombinant protein fibers, such as collagen or silk.

Methods of Purifying Curli Fibers

In some embodiments, the filter membranes used in the presently disclosed methods may be, but are not limited to, polymer membranes made of polycarbonate, nylon, cellulose, Teflon™, polyethersulfone, polyvinylidene fluoride, polyvinyidene chloride, or other materials. In some embodiments, curli fiber aggregates can be filtered on cloths, or any other fabrics with pores of the appropriate size, as described herein. In some embodiments, curli fiber aggregates can be filtered on porous mesh with pores of the appropriate size, as described herein, such as, but not limited to, metal meshes, plastic meshes, glass meshes, ceramic meshes, or polymer meshes. In some embodiments, curli fiber aggregates can be filtered on a cloth (e.g., a cotton cloth) or textile.

In some embodiments, a combination of two or more filters, cloths (e.g., porous clothes), textiles, or meshes with different pore sizes can used in the purification process. For example, two filters, cloths (e.g., porous clothes) or meshes, each with a different pore size, so that one of the filters, cloths or meshes can be used to isolate or trap bacteria, and then the other filter, cloth or mesh can be used to isolate or trap curli aggregates. In another example, two filters, cloths (e.g., porous cloths) or meshes, each with a different pore size, can be used to isolate or trap two different types of amyloid fibers or aggregates.

In some embodiments, the filter membrane can have pores of any size larger than the size of a bacterium (approximately >1 μm) and smaller than the size of an aggregate of curli fibers (approximately ~1 to 100 μm). In some embodiments, the filter membrane can have pores that are 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, 30 μm, 31 μm, 32 μm, 33 μm, 34 μm, 35 μm, 36 μm, 37 μm, 38 μm, 39 μm, 40 μm, 41 μm, 42 μm, 43 μm, 44 μm, 45 μm, 46 μm, 47 μm, 48 μm, 49 μm, 50 μm, 51 μm, 52 μm, 53 μm, 54 μm, 55 μm, 56 μm, 57 μm, 58 μm, 59 μm, 60 μm, 61 μm, 62 μm, 63 μm, 64 μm, 65 μm, 66 μm, 67 μm, 68 μm, 69 μm, 70 μm, 71 μm, 72 μm, 73 μm, 74 μm, 75 μm, 76 μm, 77 μm, 78 μm, 79 μm, 80 μm, 81 μm, 82 μm, 83 μm, 84 μm, 85 μm, 86 μm, 87 μm, 88 μm, 89 μm, 90 μm, 91

µm, 92 µm, 93 µm, 94 µm, 95 µm, 96 µm, 97 µm, 98 µm, 99 µm, or 100 µm. In some embodiments, the filter membrane can have pores that are 1 µm to 100 µm, 1 µm to 50 µm, 50 µm to 100 µm, 25 µm to 75 µm, 10 µm to 100 µm, 10 µm to 90 µm, 20 µm to 80 µm, 30 µm to 70 µm, 40 µm to 60 µm, 30 µm to 100 µm, 40 µm to 100 µm, 50 µm to 100 µm, 60 µm to 100 µm, 70 µm to 100 µm, 80 µm to 100 µm, 90 µm to 100 µm, or other ranges comprised therein. Generally, larger pores could result in greater loss of curli fiber aggregates, but increase purity after purification.

The filter membranes can have a pores of any shape or geometry. For example, in some embodiments, the pores can be circular. In other embodiments, the pores can be mesh-like. In some embodiments, the filter membranes can have pores of more than one shape or geometry.

The filter membrane may be of any geometric (e.g., circular, octagonal, rectangular, squared) or non-structured shape. The filter membrane may be of any size since the yield of purified amyloid fibers depends on the surface area of the filter membrane. Thus, larger filters allow for scaling-up of the purification process. In some embodiments, the filter membrane is at least 10 mm in diameter. For example, the filter membrane of the present invention may be at least 10 mm in diameter, 15 mm in diameter, 20 mm in diameter, 25 mm in diameter, 30 mm in diameter, 35 mm in diameter, 40 mm in diameter, 45 mm in diameter, 50 mm in diameter, 55 mm in diameter, 60 mm in diameter, 65 mm in diameter, 70 mm in diameter, 75 mm in diameter, 80 mm in diameter, 85 mm in diameter, 90 mm in diameter, 95 mm in diameter, 100 mm in diameter, 110 mm in diameter, 120 mm in diameter, 130 mm in diameter, 140 mm in diameter, 150 mm in diameter, 160 mm in diameter, 170 mm in diameter, 180 mm in diameter, 190 mm in diameter, or 200 mm in diameter. In some embodiments, the filter membrane is 47 mm in diameter.

In some embodiments, milligram quantities of amyloid fibers can be purified per liter of microbial culture using the methods described herein. In some embodiments, at least mg of amyloid fiber is purified per liter of microbial culture. In some embodiments, at least 10 mg of amyloid fiber is purified per liter of microbial culture. In some embodiments, at least 20 mg of amyloid fiber is purified per liter of microbial culture. In some embodiments, at least 30 mg of amyloid fiber is purified per liter of microbial culture. In some embodiments, at least 40 mg of amyloid fiber is purified per liter of microbial culture. In some embodiments, at least 50 mg of amyloid fiber is purified per liter of microbial culture. In some embodiments, at least 60 mg of amyloid fiber is purified per liter of microbial culture. In some embodiments, at least 70 mg of amyloid fiber is purified per liter of microbial culture. In some embodiments, at least 80 mg of amyloid fiber is purified per liter of microbial culture. In some embodiments, at least 90 mg of amyloid fiber is purified per liter of microbial culture. In some embodiments, at least 100 mg of amyloid fiber is purified per liter of microbial culture. In some embodiments, at least 150 mg of amyloid fiber is purified per liter of microbial culture. In some embodiments, at least 200 mg of amyloid fiber is purified per liter of microbial culture. In some embodiments, at least 300 mg of amyloid fiber is purified per liter of microbial culture. In some embodiments, at least 400 mg of amyloid fiber is purified per liter of microbial culture. In some embodiments, at least 500 mg of amyloid fiber is purified per liter of microbial culture. In some embodiments, at least 1000 mg of amyloid fiber is purified per liter of microbial culture.

In some embodiments, the methods of the present invention yield at least 1 mg of semi-purified amyloid fibers, at least 5 mg of semi-purified amyloid fibers, at least 10 mg of semi-purified amyloid fibers, at least 15 mg of semi-purified amyloid fibers, at least 20 mg of semi-purified amyloid fibers, at least 25 mg of semi-purified amyloid fibers, at least 30 mg of semi-purified amyloid fibers, at least 35 mg of semi-purified amyloid fibers, at least 40 mg of semi-purified amyloid fibers, at least 45 mg of semi-purified amyloid fibers, at least 50 mg of semi-purified amyloid fibers, at least 55 mg of semi-purified amyloid fibers, at least 60 mg of semi-purified amyloid fibers, at least 65 mg of semi-purified amyloid fibers, at least 70 mg of semi-purified amyloid fibers, at least 75 mg of semi-purified amyloid fibers, at least 80 mg of semi-purified amyloid fibers, at least 85 mg of semi-purified amyloid fibers, at least 90 mg of semi-purified amyloid fibers, at least 95 mg of semi-purified amyloid fibers, at least 100 mg of semi-purified amyloid fibers, at least 110 mg of semi-purified amyloid fibers, at least 120 mg of semi-purified amyloid fibers, at least 130 mg of semi-purified amyloid fibers, at least 140 mg of semi-purified amyloid fibers, at least 150 mg of semi-purified amyloid fibers, at least 160 mg of semi-purified amyloid fibers, at least 170 mg of semi-purified amyloid fibers, at least 180 mg of semi-purified amyloid fibers, at least 190 mg of semi-purified amyloid fibers, at least 200 mg of semi-purified amyloid fibers, at least 250 mg of semi-purified amyloid fibers, at least 300 mg of semi-purified amyloid fibers, at least 350 mg of semi-purified amyloid fibers, at least 400 mg of semi-purified amyloid fibers, at least 450 mg of semi-purified amyloid fibers, at least 500 mg of semi-purified amyloid fibers, or at least 1000 mg of semi-purified amyloid fibers.

In some embodiments, 1 to 50 mg of amyloid fiber is purified from 1 liter of microbial culture, 50 to 100 mg of amyloid fiber is purified from 1 liter of microbial culture, 150 to 200 mg of amyloid fiber is purified from 1 liter of microbial culture, 200 to 250 mg of amyloid fiber is purified from 1 liter of microbial culture, 300 to 350 mg of amyloid fiber is purified from 1 liter of microbial culture, 350 to 400 mg of amyloid fiber is purified from 1 liter of microbial culture, 400 to 450 mg of amyloid fiber is purified from 1 liter of microbial culture, 500 to 1000 mg of amyloid fiber is purified from 1 liter of microbial culture.

In some embodiments, semi-pure amyloid fibers are isolated in 30 minutes or less. In some embodiments, semi-pure amyloid fibers are isolated in one hour or less. In some embodiments, semi-pure amyloid fibers are isolated in two hours or less. In some embodiments, semi-pure amyloid fibers are isolated in five hours of less.

In some embodiments, two or more cultures of different bacteria engineered to express different engineered amyloid fibers can be filtered purified at the same time so as to isolate two or more different types of engineered amyloid fibers on the same filter membrane. In some embodiments, the different bacteria can be co-cultured before filter purification. In some embodiments, separate cultures of different bacteria can be mixed on the filter membrane during filter purification. In some embodiments, the filter purification of two or more types of fibers on the same filter membrane can result in purified co-assembled CsgA fibers or purified mixed curli fibers.

Filter purification of amyloid fibers according to the methods of the present disclosure require the addition of at least one solubilization agent to a bacterial culture that has been induced to produce extracellular amyloid, followed by vacuum filtration on a membrane filter. The filter membrane may be subjected to subsequent incubations with at least one solubilization agent, at least one nuclease, and at least one surfactant, with washes in between each incubation and filtration step. The filter membrane may be contacted with any one of a solubilization agent, a nuclease (e.g., a DNAse or an RNAse), and a surfactant, or to any combination thereof, as desired. In some embodiments, if the filter membrane is not contacted with a solubilization agent, bacteria may still be present in the purified amyloid fibers. In some embodiments, if the filter membrane is not contacted with a DNAse, DNA may still be present in the purified amyloid fibers. In some embodiments, if the filter membrane is not contacted with a RNAse, RNA may still be present in the purified amyloid fibers. The concentration of nuclease may affect the efficiency of nucleic acid removal. In some embodiments, the filter is contacted with a surfactant which facilitates the removal of the amyloid fibers from the membrane. In some embodiments, the filter is washed with water between each incubation and filtration step. In some embodiments, the filter is washed with a buffered solution (e.g., phosphate buffered saline) between each incubation and filtration step. The filters may be washed or incubated with the desired reagent, for a short or an extended period of time, as necessary. For example, each incubation and/or wash step may be performed for at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 15 minutes, at least 20 minutes, at least 30 minutes, at least 1 hour, at least 2 hours, at least 3 hours, at least 4 hours at least 5 hours, at least 6 hours, at least 12 hours, at least 18 hours, at least 24 hours, or more.

In some embodiments, the solubilization agent can be a denaturing solubilization agent, a non-denaturing solubilization agent, or a mild denaturing solubilization agent. In some embodiments, the solubilization agent can be, but is not limited to, guanidine, urea, DMSO, SDS, β-mercaptoethanol, or n-propanol. In some embodiments, the solubilization agent is any agent or reagent capable of inducing lysis of a microbial cell (e.g., a bacterial cell) including a lysis buffer, lysozyme, a base such as sodium hydroxide, and others. The concentration of the solubilization agent that is used may be varied, and without wishing to be bound by any particular theory, may affect the purity of the amyloid fibers that are ultimately obtained using the methods described herein. In some embodiments, the solublization agent is used at a concentration capable of inducing lysis of a bacterial cell. One of ordinary skill may readily ascertain the concentration of the solubilization agent necessary in order to induce lysis of a bacterial cell. For example, when guanidine hydrochloride is the solubilization agent that is used in the methods described herein, the concentration of guanidine hydrochloride may range from 0.1-10 M. In some embodiments, the concentration of guanidine hydrochloride is about 0.1 M, about 0.2 M, about 0.3 M, about 0.4 M, about 0.5 M, about 1 M, about 2 M, about 3 M, about 4.0 M, about 5.0 M, about 6.0 M, about 7.0 M, about 8.0 M, about 9.0 M, about 10.0 M, or more.

In some embodiments, the surfactant can be an ionic surfactant or a non-ionic surfactant. In some embodiments, the surfactant can be, but is not limited to, SDS, 4-octylphenol polyethoxylate (also known as Triton X-100™), polyethylene glycol sorbitan monolaurate (also known as Tween® 20), polyethylene glycol sorbitan monooleate (also known as Tween® 80). In some embodiments, the surfactant is used at a concentration suitable for facilitating the removal of the purified amyloid fibers from the filter. For example, when the surfactant is SDS, the filter may be contacted with a solution comprising 1% (w/v), 2%, 3%, 4%, 5%, 6%, 7%, 8%, 9%, 10% or more. In some embodiments, the surfactant is SDS at a concentration of 5% (w/v).

The methods described herein may be performed at a small scale (i.e., as a batch process) or may be adapted for large scale purification. For example, in some embodiments, the methods may be adapted to allow for the continuous and sequential contacting of microbial culture with a filter, followed by sequential incubation and wash steps (e.g., using a roll-to-roll process).

In some embodiments, the methods described herein may comprise using a filter (e.g., a cloth or textile) thereby depositing or immobilizing the amyloid onto filter. In some embodiments, the filter comprising the deposited amyloid is functionalized. For example, the deposited amyloid may comprise an activity polypeptide which allows for the subsequent attachment of a polypeptide (e.g., an enzyme onto the amyloid) such that the filter comprises an enzymatic activity. In some embodiments, multiple enzymes may be attached to the amyloid deposited on the filter such that an enzymatic cascade may be performed by the filter.

In some embodiments, the compositions and methods are used for multi-transformation cascades, wherein multiple immobilized enzymes on a biofilm carry out chemical transformations on a substrate in series in a single step manufacturing process. In some embodiments, the compositions and methods described herein are used to produce a chemical, e.g., a pharmaceutically useful product. In some embodiments, the compositions and methods described herein are used to clean up or remediate a harmful chemical spill, e.g., by catalyzing chemical reactions that transform the harmful chemical into a more benign chemical.

The compositions and methods described herein can be used in a bioreactor. In some embodiments, a curli fiber, plurality of curli fibers, genetically engineered microorganism, biofilm and/or filter comprising a curli fiber or amyloid is used in a bioreactor to catalytically transform a substrate.

EXAMPLES

Example 1: Microorganisms Engineered to Produce Unanchored Amyloid Nanofibers

The divergent curli operon regions consisting of csgBAC and csgEFG were PCR isolated from *E. coli* K12 substr. W3110 and cloned by overlap extension into the pET21d plasmid, to create a single operon, csgBACEFG, under the control of the T7 promoter. The csgB gene was then deleted from the curli operon in order to allow for secretion of the curli fibers directly into the culture medium, free from any anchoring to the bacterial surface. As shown in Table 1, genes encoding for different CsgA fusions were cloned, with modifications added to the C-terminus: 1) a six-histidine tag (HisTag) was added to allow for immunodetection, 2) a SpyTag sequence and 3) a SpyCatcher sequence. The SpyTag peptide and SpyCatcher domain form two halves of an engineered split protein system, driving spontaneous covalent bond formation between any two proteins that are fused to them. Zakeri et al., Peptide tag forming a rapid covalent bond to a protein, through engineering a bacterial adhesin. *Proc. Nat'l Acad. Sci. USA*, 109(12):E690-E697 (2012). An $L_{36}$ flexible glycine-serine linker $(GSGGSGGSGGSG)_3$ was also added to the C-terminus of CsgA, so that the linker sequence was between the CsgA sequence and the six Histidine tag, SpyTag, or SpyCatcher sequence. Table 1 depicts the sequences of the CsgA fusion proteins. A control plasmid was constructed by cloning the malE gene encoding for the maltose binding protein (MBP) from the W3110 genome into pET21d at the ndeI and bamHI cloning sites.

TABLE 1

C-terminal modifications of CsgA.

| Construct name | N-terminal sequence addition to CsgA | Function |
|---|---|---|
| CsgA-His-tag | $L_{36}$-HHHHHH (SEQ ID NO: 2) | Tag for immunodetection |
| CsgA-SpyTag | $L^{36}$-AHIVMVDAYKPTK (SEQ ID NO: 3) | Covalent binding with proteins fused to SpyCatcher domain |
| CsgA-SpyCatcher | $L^{36}$-GAMVDTLSGLSSEQGQSGDMTIEEDSATHIKFS KRDEDGKELAGATMELRDSSGKTISTWISDGQVKDF YLPGKYTFVETAAPDGYEVATAITFTVNEQGQVTVN GKATKGDAHI (SEQ ID NO: 4) | Covalent binding with proteins containing a SpyTag |

Modifications could be made to the N-terminus of CsgA, in addition to, or alternative to, modifications made at the C-terminus of CsgA.

Protein expression was performed in a curli operon deletion mutant, PQN4, an *E. coli* strain derived from LSR10 (MC4100, ΔcsgA, Δ(DE3), Cam®), so as to prevent chromosomally expressed curli proteins. PQN4 was constructed by genomic insertion of T7 RNA Polymerase using the λDE3 Lysogenization Kit (Merck-Millipore) into LSR10, verifying for T7-dependent pET expression, and then using Lambda Red recombination to knockout the curli operon using pKD46 and pKD3 (plasmids obtained from *Coli* Genetic Stock Center, Yale University). The deletion of the curli operon was confirmed by sequencing of the curli operon region. Venus yellow fluorescent protein constructs (Venus-SpyTag, Venus-SpyCatcher) were cloned into and expressed from a pDEST14 backbone (Addgene #35044), followed by purification using a Ni-NTA affinity column.

PQN4 was derived from a strain that does not produce any other extracellular polymers (e.g., flagella, pili, cellulose). Chapman et al., Role of *Escherichia coli* Curli Operons in Directing Amyloid Fiber Formation, *Science* 295(5556): 851-855 (2002). PQN4 was complemented by a plasmid encoding a subset of the genes necessary for curli production and secretion (csgACEFG), without the presence of csgD and csgB. csgD is not included because its primary role is regulating the expression of the curli genes through transcriptional repression, and is therefore unnecessary for purposes of the invention. The gene product of csgB is a membrane bound protein (CsgB) whose main roles are to initiate amyloid formation at the cell surface and anchor curli fibers to the cell. Therefore, csgB was not included in the plasmid so that secreted and assembled CsgA would remain untethered to the bacterial surface, thereby simplifying purification.

Transformed PQN4 cells were streaked onto lysogeny broth (LB) agar plates containing 100 μg/mL carbenicillin and 0.5% (m/v) glucose (for catabolite repression of T7RNAP). Colonies were picked from the plates and 5 mL cultures were inoculated (in LB containing and 100 μg/mL carbenicillin and 2% (m/v) glucose). Cultures were grown overnight at 37° C. The overnight cultures were diluted 100-fold in fresh LB medium with 100 μg/mL carbenicillin and 2% (m/v) glucose, and cultured at 37° C. until they reached an optical density (OD) at 600 nm of 0.6 to 0.8. Cells were pelleted at 4000×g, and gently resuspended in an induction medium (LB without glucose, containing 0.4 mM IPTG and 100 μg/mL carbenicillin). Protein expression was allowed to occur at 37° C. overnight.

As shown in FIG. 1, CsgA proteins overexpressed in the absence of CsgB spontaneously assemble into large aggregates in solution, while they remain more dispersed and anchored to the bacteria in the presence of CsgB. Although CsgB is known to act as a nucleator for the polymerization of CsgA in vivo, it has also been demonstrated that CsgA can self-polymerize in vitro in the absence of CsgB. Hammer et al., The curli nucleator protein, CsgB, contains an amyloidogenic domain that directs CsgA polymerization. *Proc. Nat'l Acad. Sci USA* 104(30):12494-12499 (2007); Wang et al., The Molecular Basis of Functional Bacterial Amyloid Polymerization and Nucleation. *The Journal of Biological Chemistry* 283(31): 21530-21539 (2008). The absence of CsgB also facilitates lateral aggregation of fibers during the self-assembly process, which would otherwise be prevented if fibers were only nucleated at distinct, spatially separated sites on the cell surface, i.e., in the presence of CsgB. The novel curli purification process of the present invention takes advantage of this phenomenon. The curli fiber aggregates, which were tens to hundreds of microns in size, allowed for their size-dependent separation from bacteria and other small molecules or debris.

Example 2: Filtration Purification of Amyloid Nanofibers

After the overnight induction of bacterial cultures to produce extracellular CsgA, guanidinium chloride (GdmCl) was added to the cultures to reach a final concentration of 0.8 M and they were incubated for 1 to 2 hours at 4° C. prior to filtration. 30 to 50 mL of the Gdm-containing cultures were then vacuum-filtered onto 47 mm polycarbonate filter membranes with 10 μm pores (EMD Millipore). The first incubation with GdmCl, allowed for significantly larger culture volumes to be filtered without clogging the membranes. Since GdmCl is a strong chaotropic agent that can disrupt the integrity of the bacterial cell membranes, this was likely due to partial cell lysis. Andreev et al., Guanidino groups greatly enhance the action of antimicrobial peptidomimetics against bacterial cytoplasmic membranes. *Biochimica et Biophysica Acta (BBA)—Biomembranes* 1838(10):2492-2502 (2014). Next, three sequential incubations, each followed by water rinses, were performed directly on the filter membranes: 1) 8 M GdmCl was used to lyse any remaining bacterial cells and remove non-specifically bound proteins from the curli fibers, 2) a solution of a nuclease with DNAse and RNase activity was used to digest nucleic acids that tend to bind to curli fibers, (Gallo, P. M et al., Amyloid-DNA composites of bacterial biofilms stimulate autoimmunity, *Immunity* 42(6):1171-1184 (2015)) and 3) incubation with SDS allowed for delamination of curli aggregates from the membrane and easy collection of the purified fibers with a spatula. More specifically, the filtered biomass was incubated with 5 mL of 8 M GdmCl for 5 min, followed by vacuum filtration of the liquid and 3 rinses with 5 mL of DI water. Next, the filtered biomass was subjected to 5 mL of an aqueous solution (2 µM $MgCl_2$) of nuclease (Benzonase®, Sigma-Aldrich, 1.5 U/mL) for 10 min, followed by vacuum filtration to remove the liquid and 3 rinses with 5 mL of DI water. Finally, 5 mL of 5% (m/v) sodium dodecyl sulfate (SDS) in water was incubated on the filter for 5 min, followed by vacuum filtration of the liquid and 5 rinses with 5 mL of DI water. Semi-purified curli nanofibers were removed from the filter membrane by gently scraping the filter with a flat spatula. Purified curli nanofibers were lyophilized and subsequently stored at 4° C.

Figure 2B:
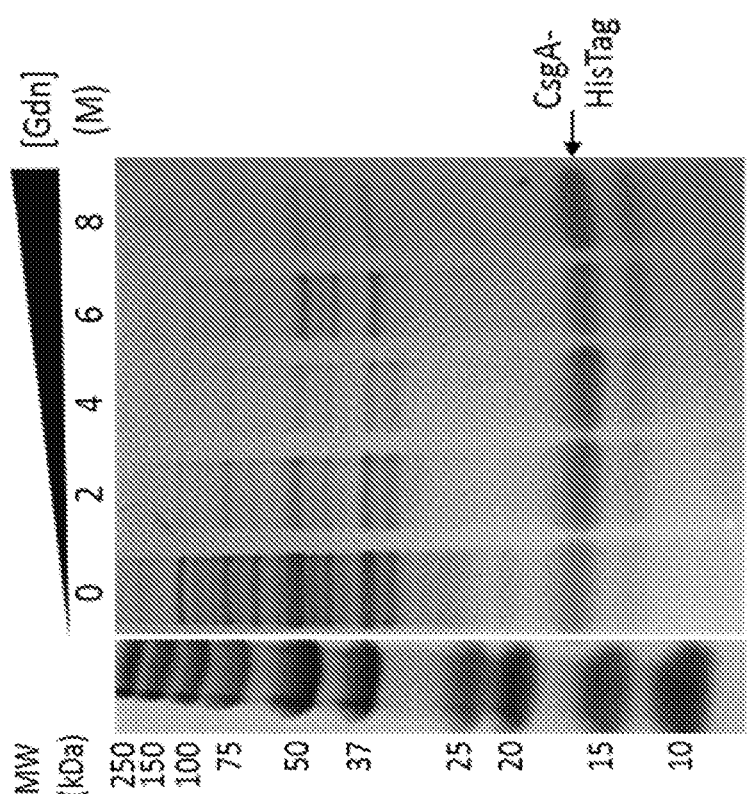
FIGS. 2A, 2B, 2C, and 2D show SDS-PAGE analysis of CsgA purity after treatment of filtered bacterial cultures with GdmCl and subsequent washing steps, followed by removal from membranes.
Figure 2A:
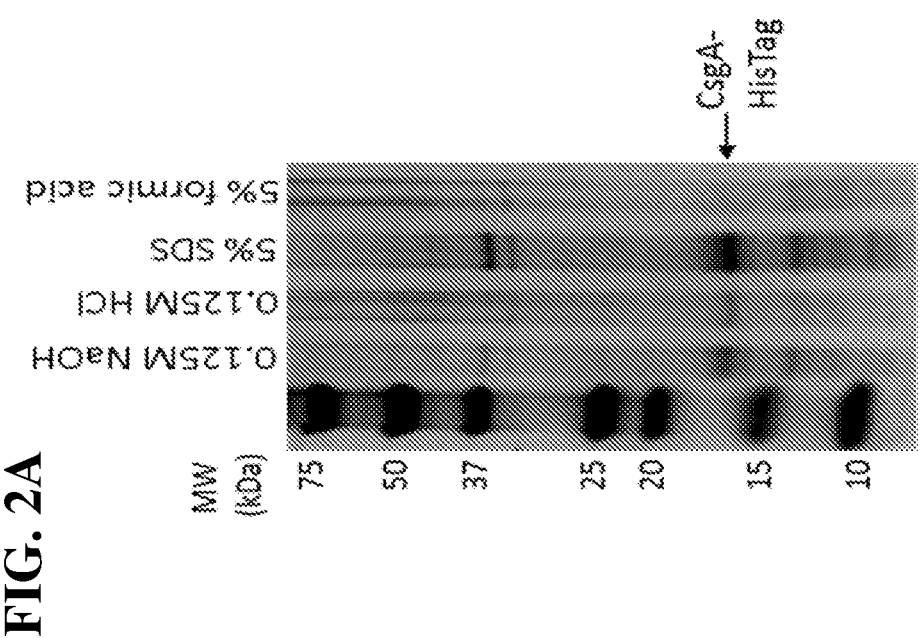

An SDS incubation was selected as the last step in the purification process, after trying several solvents to facilitate removal of the curli fibers from the membrane, because it allows for the delamination of the curli nanofiber films from the membranes. As shown in FIG. 2A, if the SDS incubation step is replaced with an incubation with bases or acids, the yield of nanofibers decreases significantly after scraping the curli nanofibers off of the membrane. Surprisingly, formic acid did not facilitate the removal of the fibers from the membranes, even though it is known to disassemble curli fibers. Zhou et al., Experimental Manipulation of the Microbial Functional Amyloid Called Curli. In *Bacterial Cell Surfaces: Methods and Protocols*, Delcour, H. A., Ed. Humana Press: Totowa, N.J., 2013; pp 53-75.

Figure 2D:
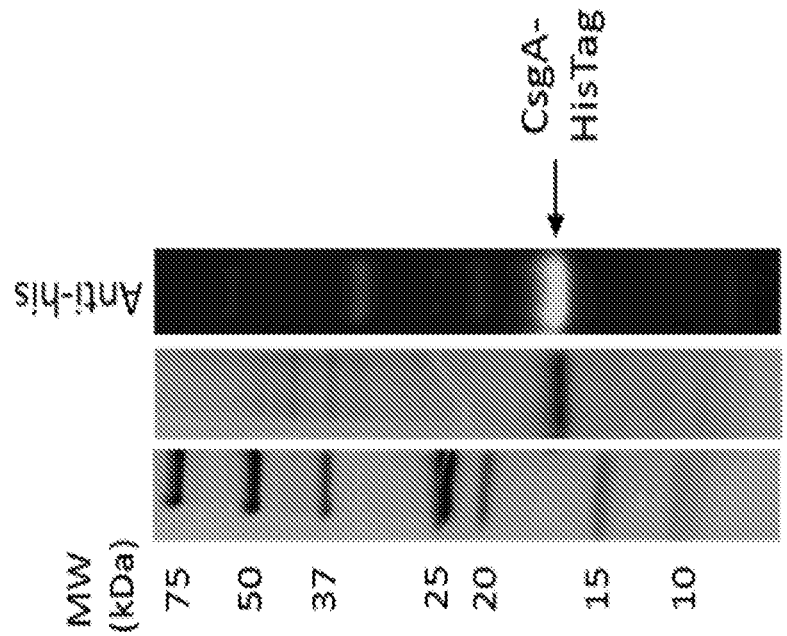
Figure 2C:
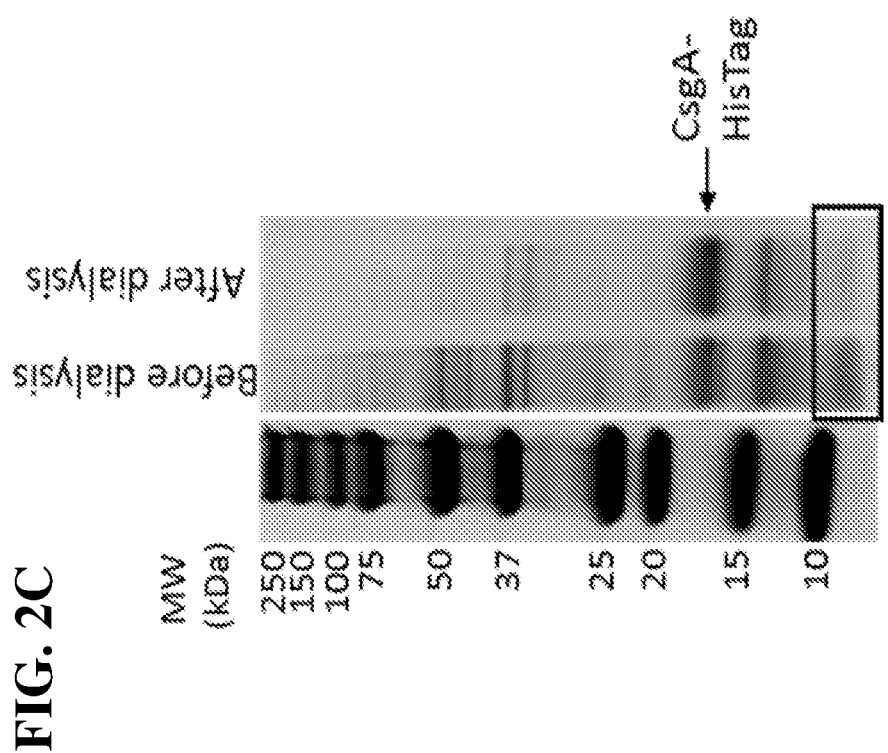

To investigate the impact of the GdmCl incubation step on purity, curli nanofibers were collected from filter membranes after being treated with varying concentrations of GdmCl from 0 to 8 M. As shown in FIG. 2B, the number and concentration of impurities decreases as the concentration of GdmCl increased, although some impurities persisted even at the highest GdmCl concentrations. It is possible to adjust the guanidine HCl concentration as a function of the desired final product purity and the sensitivity of CsgA fusion proteins to this chaotropic agent. For example, if the domains that are fused to CsgA are prone to denaturation, lower concentrations of GdmCl could be used, at the expense of protein purity. Relatively pure CsgA can be obtained at GdmCl concentrations as low as 2 or 4 M, which could allow for the purification of a wide variety of genetically engineered CsgA fusions. While concentrations of GdmCl in the range of 4 to 8M are normally known to cause partial or full protein denaturation, curli nanofibers are highly resistant to denaturing agents and solvents and likely create a protective mesh that could prevent or reduce denaturation of protein domains fused to CsgA, as observed previously for bio-active molecules like enzymes immobilized onto protein scaffolds. Gallo et al., Amyloid-DNA composites of bacterial biofilms stimulate autoimmunity. *Immunity* 42(6):1171-1184 (2015); Camilloni et al., Urea and Guanidinium Chloride Denature Protein L in Different Ways in Molecular Dynamics Simulations. *Biophysical Journal* 94(12):4654-4661 (2008); Collinson et al., Purification and characterization of thin, aggregative fimbriae from *Salmonella enteritidis*. *Journal of Bacteriology* 173 (15):4773-4781 1991); Evans & Chapman, Curli Biogenesis: Order out of Disorder. *Biochimica et biophysica acta* 1843(8):1551-1558 (2014); Botyanszki et al., Engineered catalytic biofilms: Site-specific enzyme immobilization onto *E. coli* curli nanofibers. *Biotechnology and Bioengineering* 112(10):2016-2024 (2015); Domachuk et al., Bioactive "self-sensing" optical systems. *Applied Physics Letters* 95(25):253702 (2009). As depicted in FIG. 2C, if desired, further purification of the curli fibers can be achieved via dialysis, to remove any small residual proteins or peptides. As shown in FIG. 2D, the presence of CsgA in the final purified product was confirmed using Western blot.

The main impurity observed by Coomassie staining of the gels, at ~14 kDa was identified by mass spectrometry as partially degraded CsgA (see Table 2), and other impurities correspond to a mixture of other *E. coli* proteins. Densitometry analysis of the Coomassie gel bands from the purification using 8M GdmCl indicates that CsgA proteins make up ~80% of the total protein content of the material, with 15% of this in the degraded form. CsgA-HisTag was used to identify peptides, and an *E. coli* protein database was used to calculate the ratio (intensity %) of peptides identified in CsgA to the total peptides identified in CsgA-HisTag and in the *E. coli* database for each band.

TABLE 2

Peptide match to CsgA-HisTag using microcapillary LC/MS/MS mass spectrometry.

| Construct name | Unique peptides | Total peptides | Reference sequence | Sum Intensity | Intensity % |
|---|---|---|---|---|---|
| CsgA-HisTag at 16.7 kDa | 147 | 218 | CsgA-HisTag | $1.8 \times 10^9$ | 64.51 |
| Partially degraded CsgA at 14 kDa | 100 | 124 | CsgA-HisTag | $3.4 \times 10^8$ | 53.76 |

Example 3: Characterization of Filtration Purified Amyloid Nanofibers

Curli nanofiber expression was confirmed directly from suspension culture using a Congo Red pull down assay. Nguyen et al., Programmable biofilm-based materials from engineered curli nanofibres. *Nat Commun* 5 (2014). Briefly, 1 mL of culture expressing curli was centrifuged and the pellet was resuspended in phosphate buffer. Congo Red was added to a concentration of 0.00015% (m/v). After a 10 minute incubation, cells were centrifuged and the absorption at 490 nm of the supernatant was measured to quantify the amount of Congo Red that did not bind to the cells. The deposition of curli nanofibers on filter membranes was also assessed using Congo Red dye binding. After all the filtration steps, 5 mL of a 0.015% (m/v) of Congo Red dye was incubated on the filters for 10 min, followed by vacuum filtration of the liquid and 3 rinses with 5 mL of DI water. As controls, Congo Red dye was also incubated on clean filter membranes and on membranes with control cells expressing MBP instead of curli fibers.

Figure 3A:
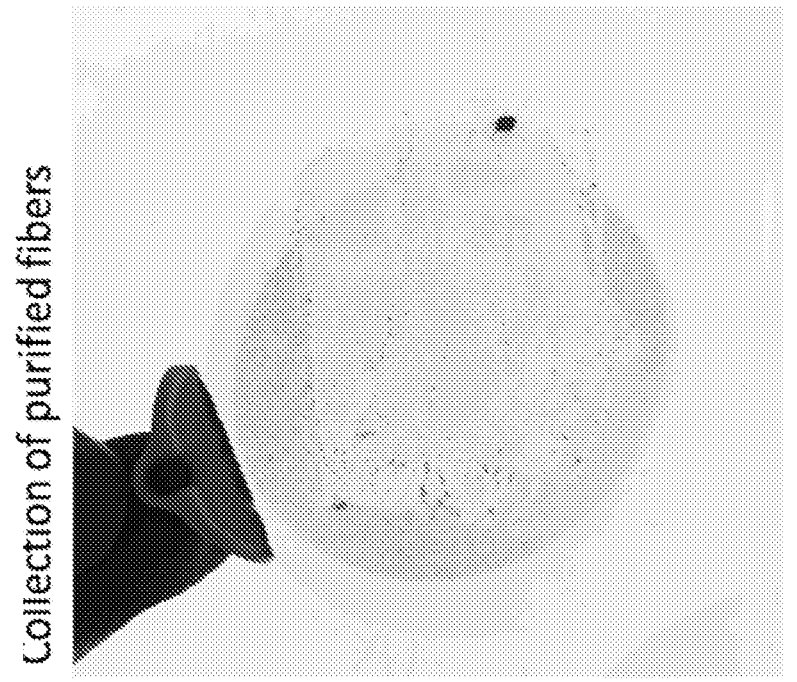
FIGS. 3A and 3B depict Congo Red staining showing the presence of curli fibers on filter membranes.

The amyloid-specific dye, Congo Red, was used in order to visually monitor the retention of assembled curli fibers during the filtration process. As depicted by FIG. 3A, after the initial filtration of the bacterial culture, followed by water rinses to remove any non-specifically adsorbed dye, a bright red color was observed for membranes containing wild-type curli nanofibers. Although the color was mostly retained during the sequential purification steps, a slight decrease in dye intensity was observed, which could be attributed to a loss of curli fibers material, or to the removal of other aggregated proteins or cellular debris that binds Congo Red non-specifically. A negative control with bacteria expressing only maltose binding protein did not show any Congo Red retention, as expected.

Figure 3B:
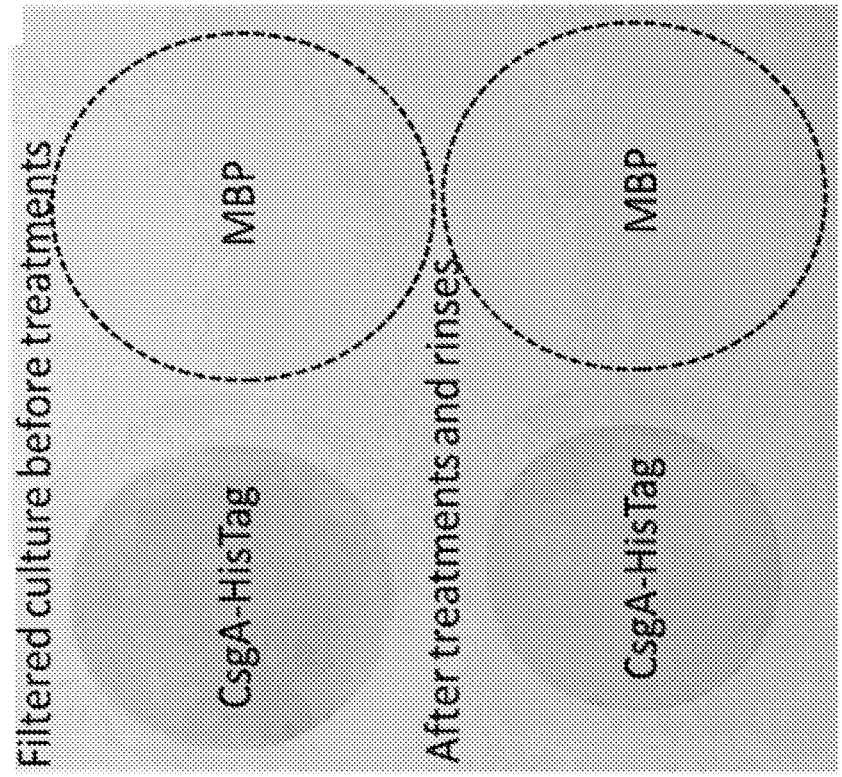

Purified curli fibers could be used in downstream applications when in various forms, including as purified fibers, as curli fiber films, or when deposited on a filter membrane. Some applications for amyloid-based materials, such as water decontamination, could directly make use of curli nanofiber films deposited on filter membranes. Bolisetty & Mezzenga, Amyloid-carbon hybrid membranes for universal water purification. *Nat Nano* 11(4):365-371 (2016). However, other applications would benefit from the removal of nanofibers aggregates from the membranes, or even solubilization and disassembly of the fibers into monomeric CsgA subunits. As shown in FIG. 3B, after the full purification sequence, curli nanofibers can be simply scrapped off of the membrane surface using a spatula. In addition, they can be solubilized, disassembled using a 1:1 HFIP/TFA mixture and reassembled in water or buffer.

SDS-PAGE/Western Blot:

The purity of filtered curli nanofibers was assessed using SDS-PAGE. Curli fibers scrapped off from filter membranes were disassembled by dissolving them in a 1:1 (v/v) HFIP/TFA mixture, and incubating with sonication until the solution turned clear. After evaporating the solvent, the samples were resuspended in DI water and loading buffer. Western blotting was used to confirm the presence of HisTags on curli fibers after filtration. Samples were run on a NuPAGE Novex 4-12% Bis-Tris gel and transferred on an iBlot PVDF membrane (Invitrogen). After blocking with 5% milk in TBST, the membrane was treated with a monoclonal mouse anti-His antibody HRP conjugate (ThermoFischer). Chemiluminescence was detected using a FluorChem™ M system (Protein Simple).

Electron Microscopy:

Scanning electron microscopy (SEM) samples were prepared by washing the filter membranes with deposited curli nanofibers with 0.1 M sodium cacodylate buffer, and fixing with 2% (m/v) glutaraldehyde and 2% (m/v) paraformaldehyde for 2 hours at room temperature. The membranes were then washed in water, and the solvent was gradually exchanged to ethanol with an increasing ethanol 15 minute incubation step gradient (25%, 50%, 75% and 100% (v/v) ethanol). The membranes were dried in a critical point dryer and sputtered until they were coated in a 5 nm layer of Pt/Pd. Imaging was performed using a Zeiss Ultra 55 Field Emission SEM.

Figure 4A:
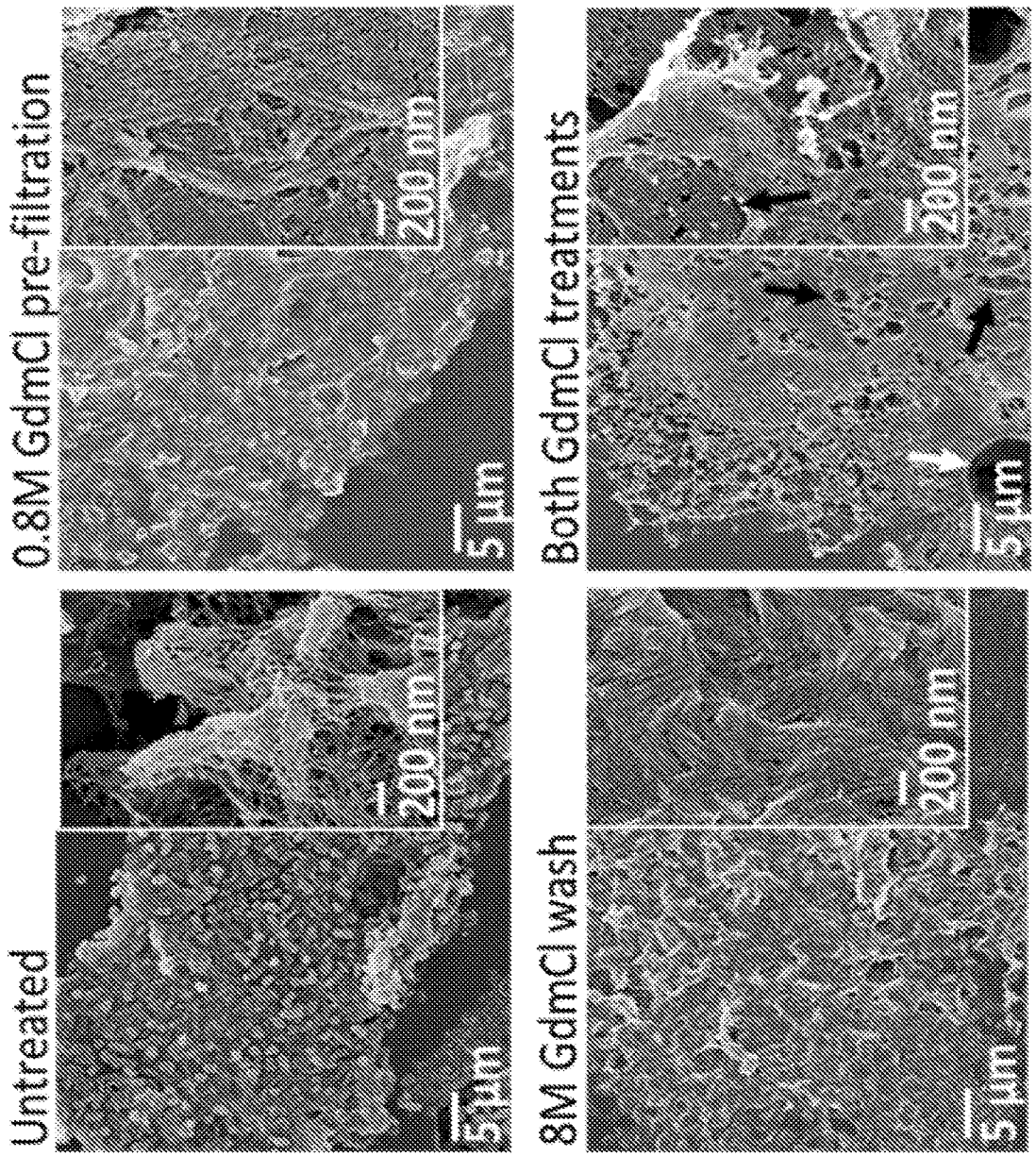
FIGS. 4A and 4B show that GdmCl and SDS treatments allow for purification and delamination of the curli nanofiber films. Scanning electron microscopy images after various treatments are provided.

As depicted in FIG. 4, scanning electron microscopy (SEM) was used to visualize the curli thin films directly on filter membranes after fixation with glutaraldehyde and paraformaldehyde to preserve their native morphology. As shown in FIG. 4A, without any GdmCl treatment, several bacteria were present on the surface of the curli aggregates. The vast majority of bacteria were removed by treating the cultures with 0.8 M GdmCl prior to filtration, but a few intact cell bodies could still be identified. The most effective step for removing bacterial cells was the 8 M GdmCl rinse after filtration of the culture. After both the GdmCl pretreatment, and the 8 M GdmCl wash step, several empty spaces in the film appeared, which were presumably occupied by bacteria previously. In all cases, nanofibrous features remained visible after GdmCl incubations (FIG. 4, insets), but the fibers tended to aggregate more with exposure to GdmCl.

Figure 4B:
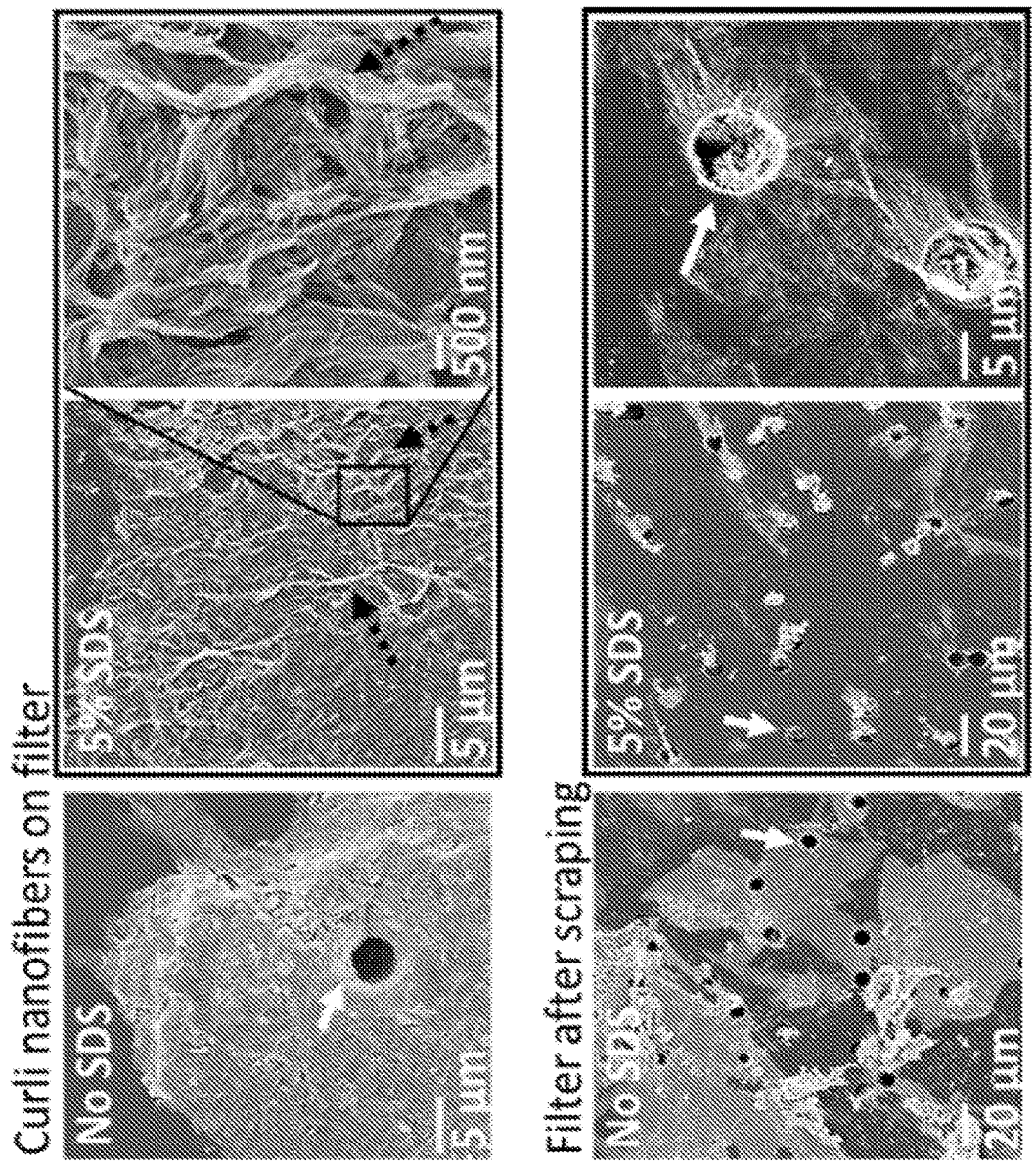

As shown in FIG. 4B, SEM images of filtered films were also obtained before and after SDS treatment in order to determine why SDS made removal so much easier compared to other treatments. SDS treatment caused the film to wrinkle and partially delaminate from the surface of the membrane. We then attempted to scrape off curli nanofibers from filters treated with SDS filters that were untreated. Without SDS incubation, it was impossible to remove the curli nanofibers from the surface and the aggregates remained intact, deposited on the membrane. In contrast, very little material remained on the surface of filters treated with SDS after scraping. Interestingly, surface wrinkling is also used in microbiological studies as a phenotypic marker for the presence of curli fibers in biofilms. White et al., Extracellular Polysaccharides Associated with Thin Aggregative Fimbriae of *Salmonella enterica* Serovar *enteritidis*. *Journal of Bacteriology* 185(18):5398-5407 (2003); Lim et al., Community behavior and amyloid-associated phenotypes among a panel of uropathogenic *E. coli*. *Biochemical and Biophysical Research Communications* 443(2):345-350 (2014).

Confocal Microscopy:

Curli nanofibers deposited on membranes were stained with thioflavin T (ThT) (20 mM solution in water) for 1 h, and DNA with SYTO 59 Red Fluorescent Nucleic Acid Stain (5 µM solution in water) for 30 min. A Leica SP5×MP Inverted Confocal Microscope was used for imaging.

As depicted in FIG. 9, the purification of curli nanofibers from DNA was further confirmed by confocal microscopy using SYTO 59 Red Fluorescent Nucleic Acid Stain to stain DNA and RNA. After treatment with nuclease, a significant decrease in the amount of nucleic acids was observed within the curli fiber mesh, and only a background fluorescence signal remained. The presence of the curli fibers on the membrane through the process was also confirmed by Thioflavin T (ThT) staining.

Fourier-Transformed Infrared Spectroscopy (FTIR):

FTIR was used to evaluate the secondary structure of CsgA in lyophilized curli fibers obtained via filtration and in free-standing curli films. The measurements were performed with a Brucker Vertex 70 Spectrometer. Attenuated total reflection (ATR) spectra in the 1550-1750 $cm^{-1}$ range were obtained with a 1 $cm^{-1}$ resolution. Curve fitting was performed using the OPUS software.

Mass Spectrometry: Bands were cut from Coomassie blue-stained SDS-PAGE gels and digested with trypsin. Microcapillary electrospray LC/MS/MS analysis was performed at the Taplin Mass Spectroscopy Facility using an Orbitrap mass spectrometer (Thermo Scientific).

Example 4: Purification of Amyloid Nanofibers Using Different Types of Filters

The filter membranes used to purify curli nanofibers may be different materials, including, but are not limited to, polymer membranes made of polycarbonate, nylon, cellulose, Teflon™, polyethersulfone, polyvinylidene fluoride, polyvinyidene chloride, or other materials. FIGS. 13A-13D depicts SEM images following filtration purification of wild-type curli fibers on a nylon filter.

Example 5: Fabrication of Free-Standing Amyloid Films

Purified curli nanofibers on polycarbonate filter membranes were crosslinked by immersing the membrane in a 2% (m/v) glutaraldehyde and 2% (m/v) paraformaldehyde solution for 2 hours at room temperature. After water rinses, the polycarbonate filter membranes with crosslinked fibers were placed on a Teflon™ support membrane, and immersed in a dichloromethane bath for approximately 1 minute to dissolve the polycarbonate filter membrane. Free-floating curli nanofiber films were collected from the dichloromethane bath using the Teflon™ support and allowed to dry in air for an hour. Dried curli films were gently peeled off the Teflon™ support.

Figure 12B:
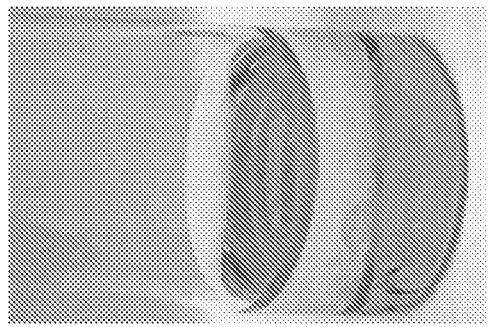
FIGS. 12A and 12B show that polycarbonate filter membranes are dissolved to obtain free-floating fibers. The curli fiber films were not crosslinked prior to membrane dissolution, resulting in the formation of several disconnected curli film pieces.
Figure 12A:
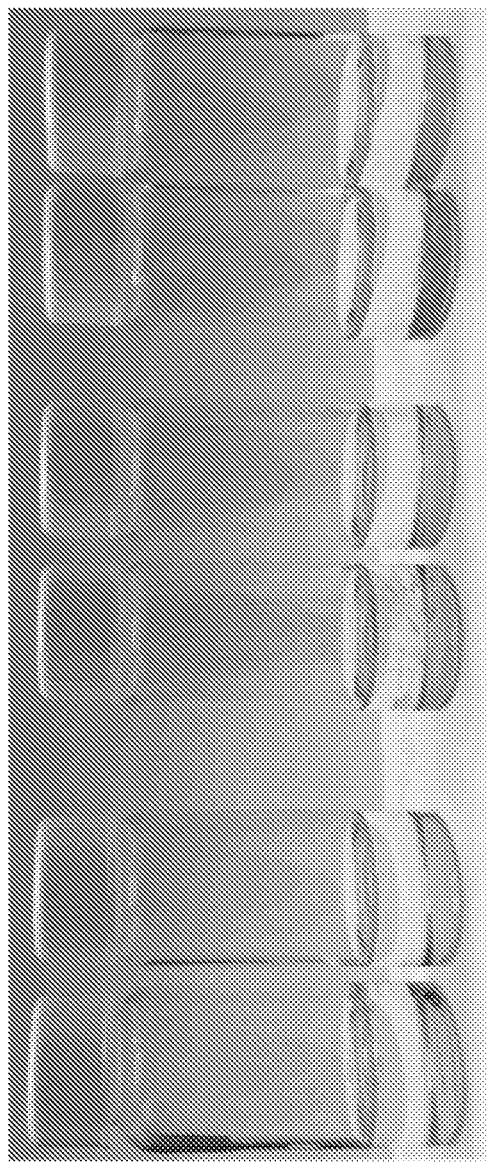
Figure 13C:
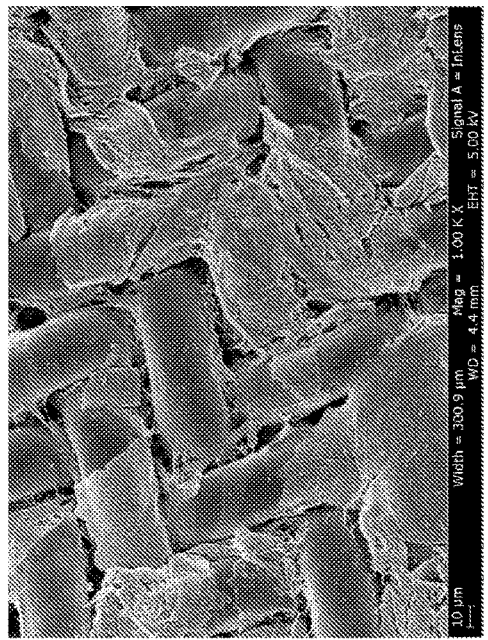
FIGS. 13A, 13B, 13C, and 13D depict SEM images following filtration purification of wild-type curli fibers on a nylon filter from (FIGS. 13A and 13B) a 40 ml culture or a 100 ml culture of bacteria (FIGS. 13C and 13D).
Figure 13D:
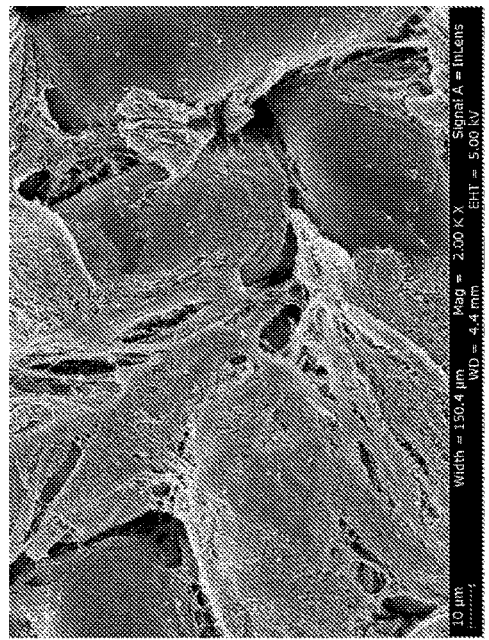
Figure 13A:
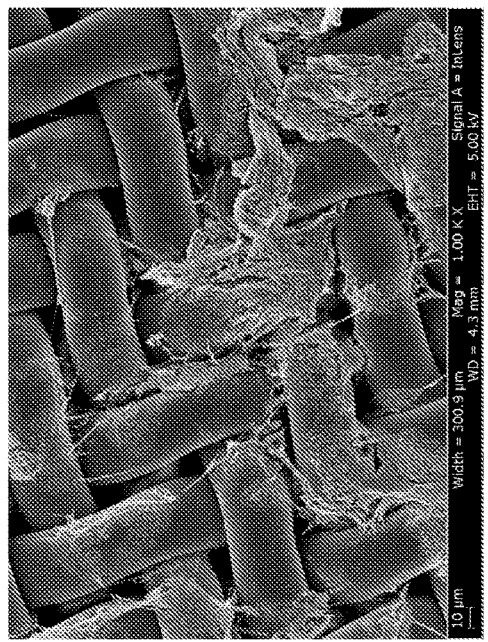
Figure 13B:
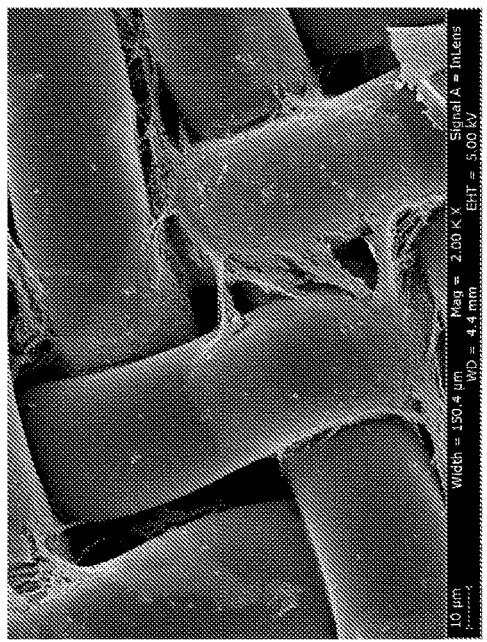
Figure 14:
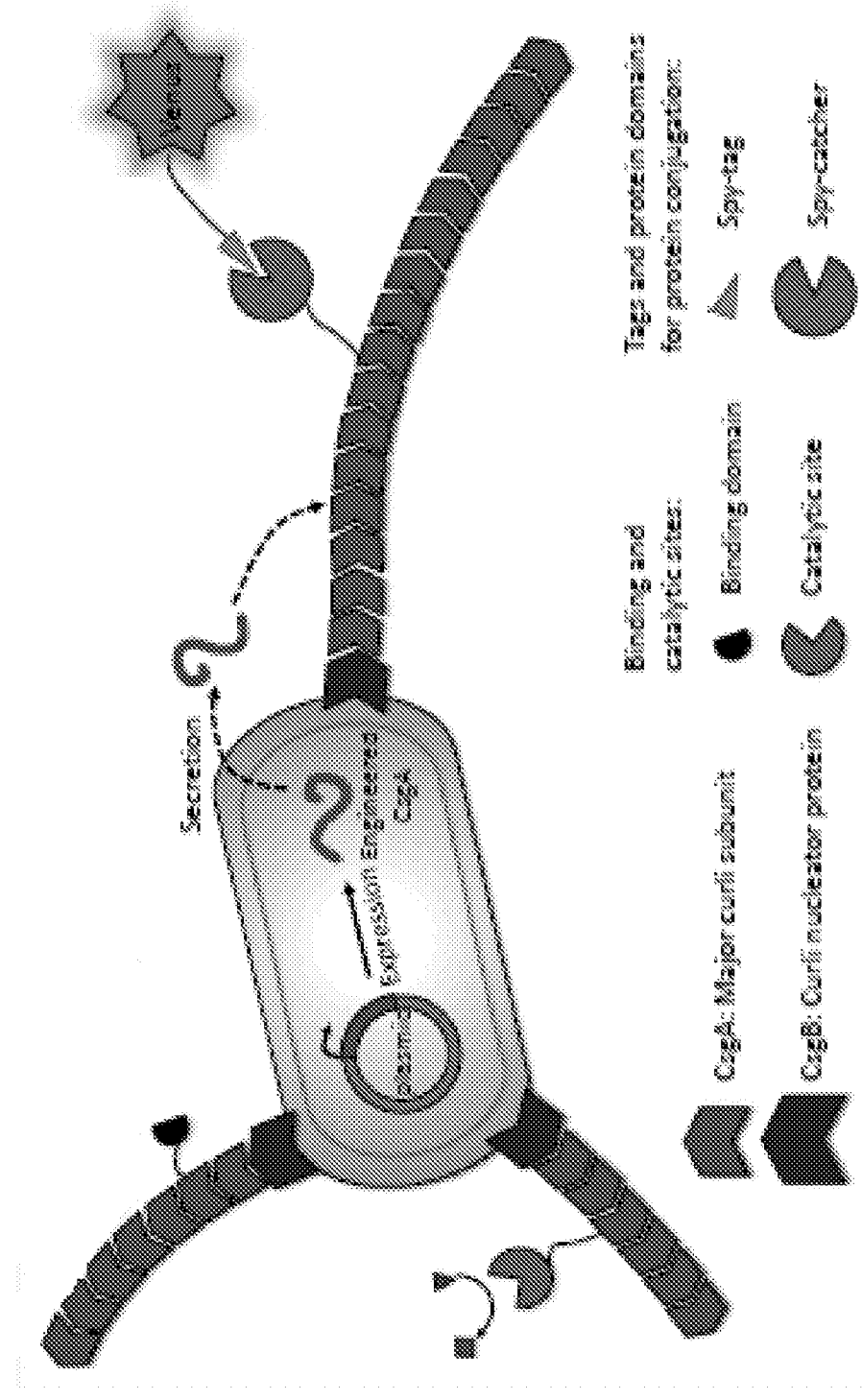
FIG. 14 depicts a recombinant bacterium expressing CsgA and CsgB to produce curli fibers anchored to the surface of the bacterium. The CsgA polypeptides may be fused or attached to a variety of functionalizing polypeptides, including domains that bind other proteins, polypeptides containing catalytic sites (e.g., enzymes), and/or conjugation domains (e.g., SpyCatcher or SpyTag) that bind to partner conjugation domains (e.g., SpyTag or SpyCatcher) attached to other proteins.
Figure 15B:
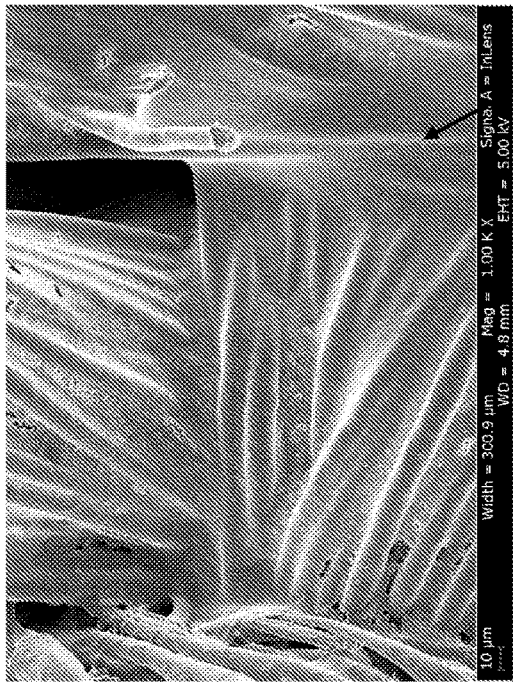
FIGS. 15A, 15B and 15C depict scanning electron microscopy imaging at three magnifications of curli fibers purified onto a porous cloth. Bacterial culture was filtered onto the porous cloth, and rinses and washes were performed to purify the fibers and remove bacteria. The purified curli fibers form bridges between textile fibers.
Figure 15A:
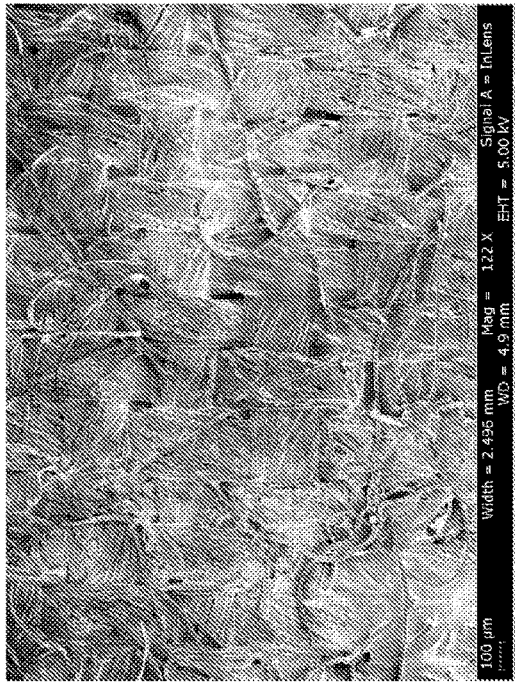
Figure 15C:
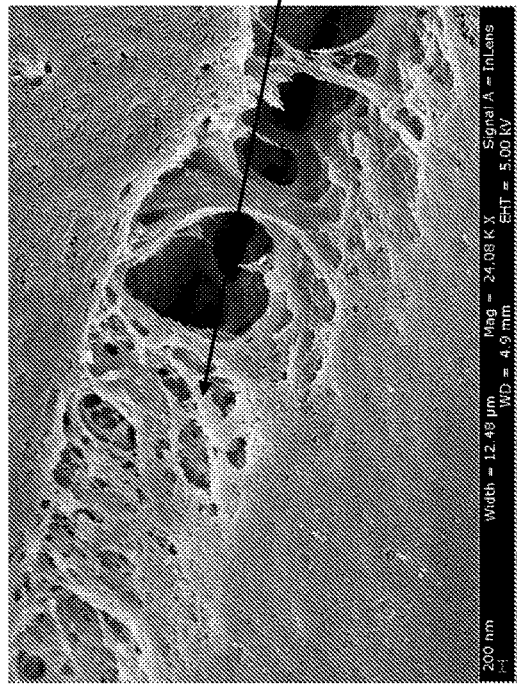

As depicted by FIG. 6, in addition to isolating recombinant protein fibers, the filtration protocol can be used as a fabrication method for producing self-standing, macroscopic, amyloid-based films. The filter membrane-supported curli fibers were crosslinked using a mixture of glutaraldehyde and paraformaldehyde. Then, as depicted in FIG. 12, the underlying polycarbonate membrane was dissolved in a dichloromethane bath. In less than a minute, the polycarbonate membrane fully dissolved, and the curli film floats in solution. As shown in FIG. 6A, Teflon™ membrane was used to collect the free-standing curli film, and, after drying, the curli film can be peeled off of the Teflon™ support. As shown in FIG. 6B-C, the resulting thin film is transparent and flexible. FIG. 6D shows that the activity of the displayed SpyTag fusion was remarkably maintained, even after cross-linking and immersion in organic solvent.

Figure 6A:
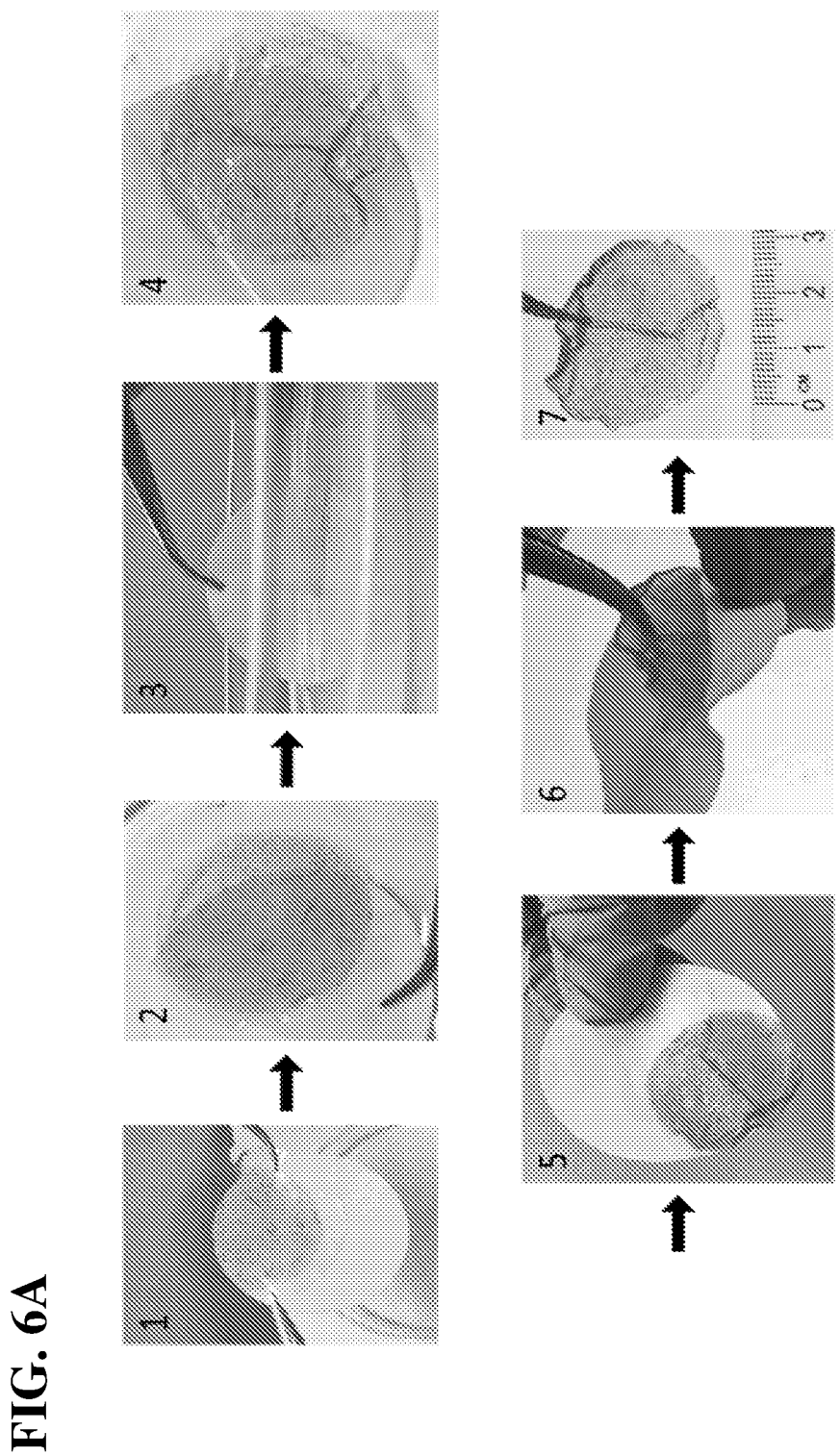
FIGS. 6A, 6B, 6C, 6D, 6E, and 6F depict free-standing curli fiber thin films fabricated via filtration. A. The fabrication protocol begins with purified, crosslinked fibers on a polycarbonate filter membrane.
Figure 6B:
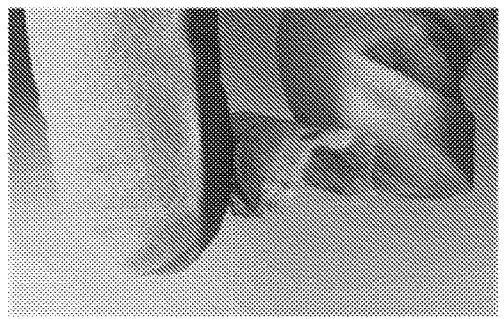
Figure 6C:
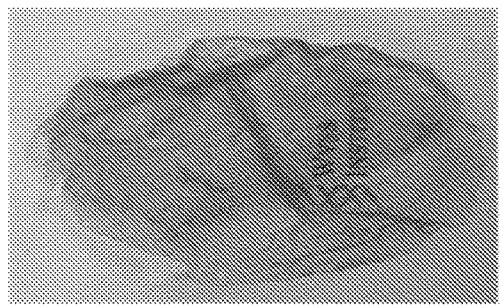
Figure 6D:
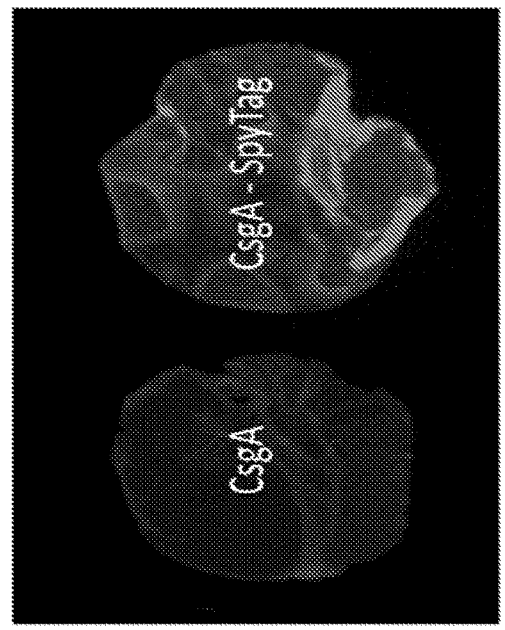
Figure 6F:
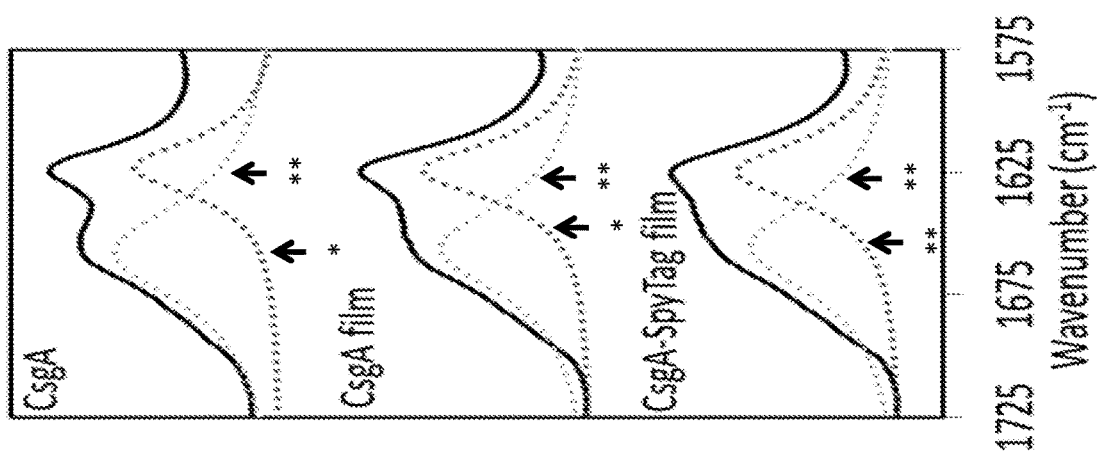
Figure 6E:
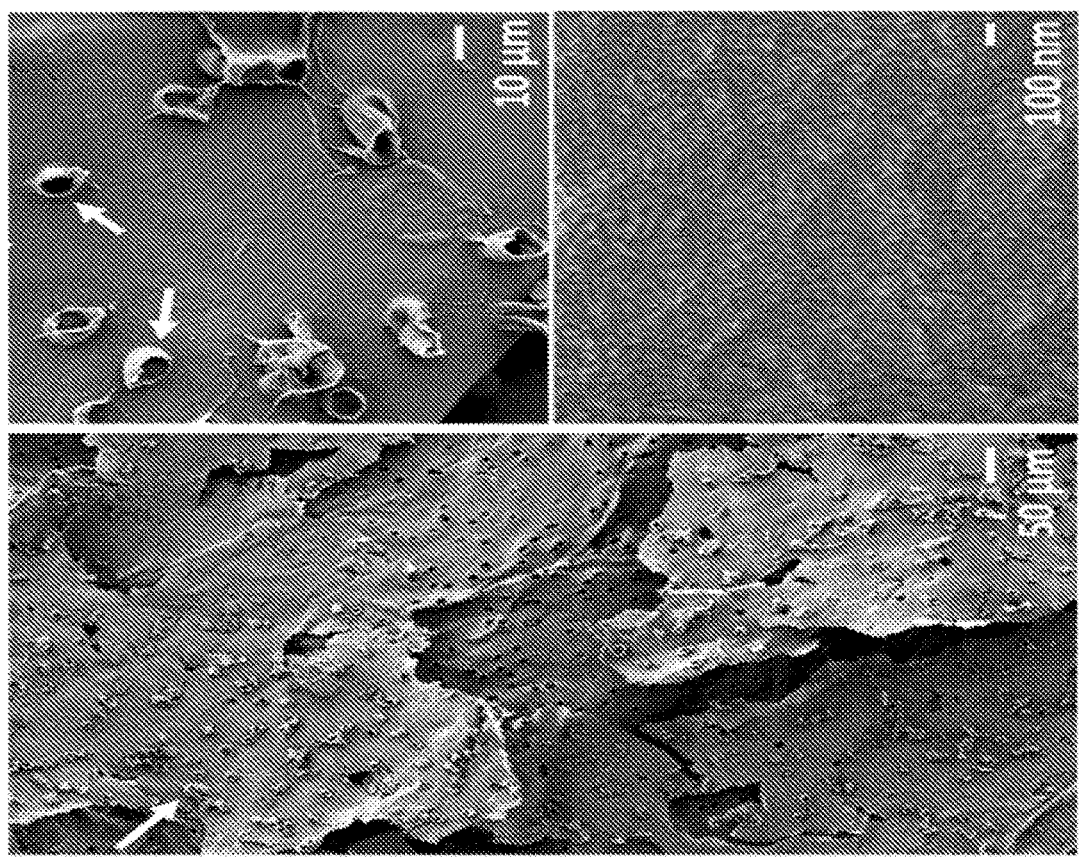

The morphology and secondary protein structure of the films were investigated. As depicted in FIG. 6E, SEM was used to visualize free-standing films that had been air-dried on the bench top and revealed the presence of large overlapping sheets of material, with dimensions corresponding approximately to the size of the curli aggregates previously observed on polycarbonate membranes after filtration. The pores from the polycarbonate were imprinted in the curli structure in some images, and that portions of the curli fiber mats that were pulled into the pores during filtration formed extruded cylindrical structures. At higher magnifications, a tightly interconnected nanoporous structure is observed, likely corresponding to curli fibers that collapsed onto each other due to drying. FTIR further confirmed that the free-standing films were composed of material with secondary structure similar to lyophilized curli fibers scraped from filter membranes. FIG. 6F shows the amide I peak spectra for lyophilized purified curli, and for free-standing films of CsgA and CsgA-SpyTag. In all cases the curves can be fitted with two Lorentz peaks corresponding to β-sheet folded proteins (around 1624 cm$^{-1}$) and to disordered or aggregated structures (around 1650 cm$^{-1}$).[34][35]

With preserved secondary structure and binding activity, the free-standing curli fiber films could be used to bind a variety of functional proteins, enzymes or molecules using the SpyTag-SpyCatcher system for a wide range of applications.

Example 6: Assessing the Activity of CsgA-SpyTag and CsgA-SpyCatcher Fusions on Filter Membranes and Free-Standing Curli Films After determining that the filtration scheme purified tag-less, wild-type CsgA, a similar demonstration was conducted for amyloid fibers displaying fused functional domains, thereby providing an entry point to genetically engineered protein-based materials. The SpyTag-SpyCatcher conjugation scheme is highly effective for immobilization of proteins to assembled curli fibers. Zakeri et al., Peptide tag forming a rapid covalent bond to a protein, through engineering a bacterial adhesin. *Proc. Nat'l Acad. Sci.* 109(12):E690-E697 (2012).

Venus yellow fluorescent protein fusions containing either SpyTag or SpyCatcher were used to assess the binding activity of engineered curli nanofibers, as described previously. Venus-SpyCatcher and Venus-SpyTag fusion proteins were produced recombinantly. Nagai et al., A variant of yellow fluorescent protein with fast and efficient maturation for cell-biological applications. *Nat Biotech* 20(1):87-90 (2002); Nguyen et al., Programmable biofilm-based materials from engineered curli nanofibres. *Nat Commun* 5 (2014). The Venus fusion protein solutions were diluted to 10 µM in 50 mM phosphate buffer pH 7.2 and incubated on filter membranes with purified CsgA-SpyTag or CsgA-SpyCatcher nanofibers for 90 minute at 4° C. The liquid was then filtered through, and the membrane was rinsed with 5 times with 5 mL of DI water. To exclude non-specific binding on filter membranes, the following controls were also incubated with Venus-SpyCatcher or Venus-SpyTag: 1) purified CsgA-HisTag nanofibers, 2) cells expressing only MBP and subjected to the same filtration treatment, and 3) bare untreated filter membranes. The same protocol was used for Venus-SpyCatcher binding on free-standing CsgA-SpyTag curli films.

Figure 5A:
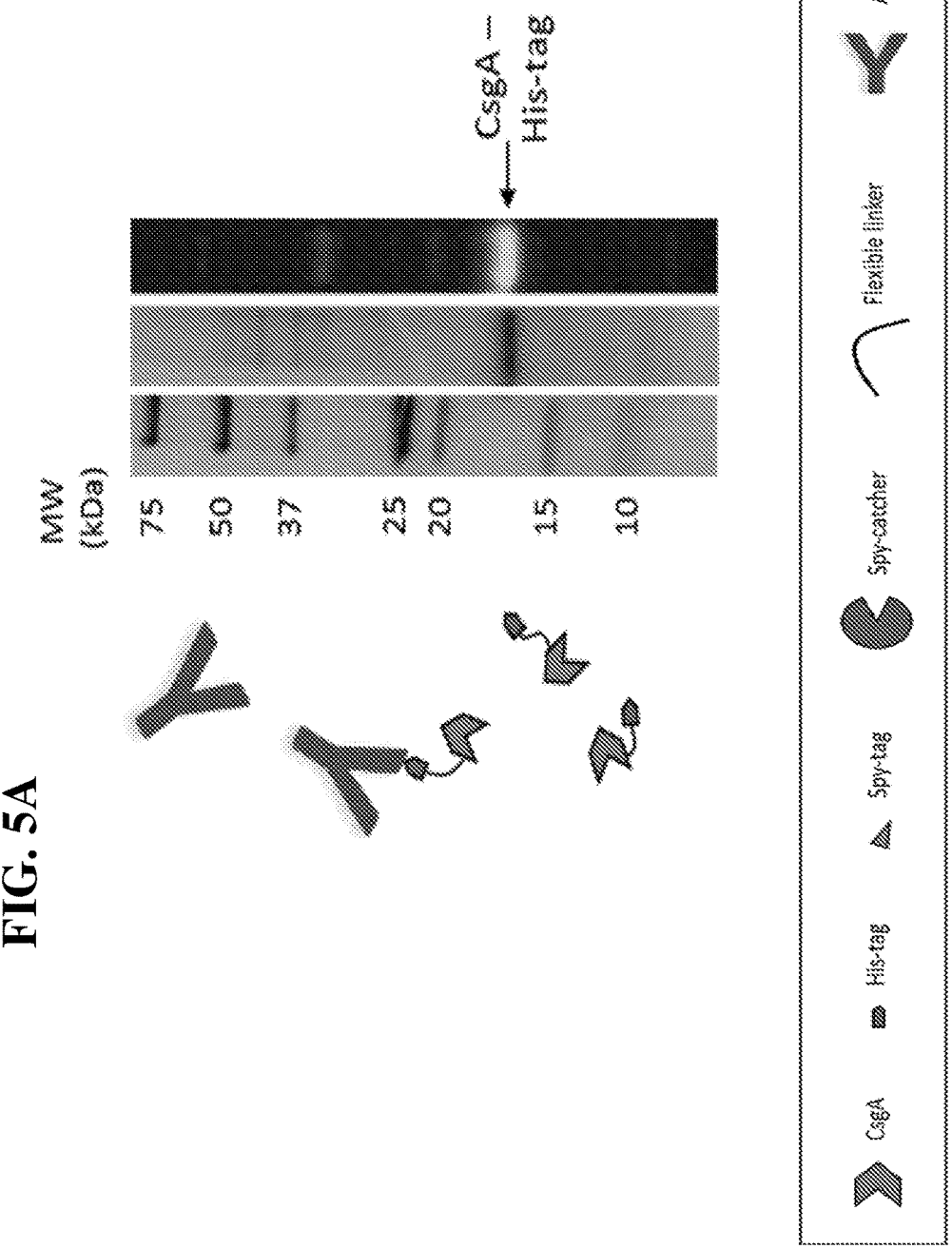
FIGS. 5A, 5B, and 5C show that engineered curli nanofibers displaying small tags or larger protein domains remain active after purification.

To confirm that the 13 amino acid SpyTag domain was active after exposure to the rigorous filtration protocol, filtered curli fibers displaying SpyTag were treated to the washing protocol, then exposed to Venus-SpyCatcher fusion protein. As shown by FIG. 5A, filters coated with SpyTag fibers retained the Venus-SpyCatcher protein after washing, while those coated with CsgA-His fibers did not, suggesting that the fluorescent protein capture was specific to the SpyTag-SpyCatcher interaction. Filters treated with MBP-expressing bacteria, His-tagged curli nanofibers on filters, and bare filters also did not trap the Venus-SpyCatcher chimera.

Figure 5B:
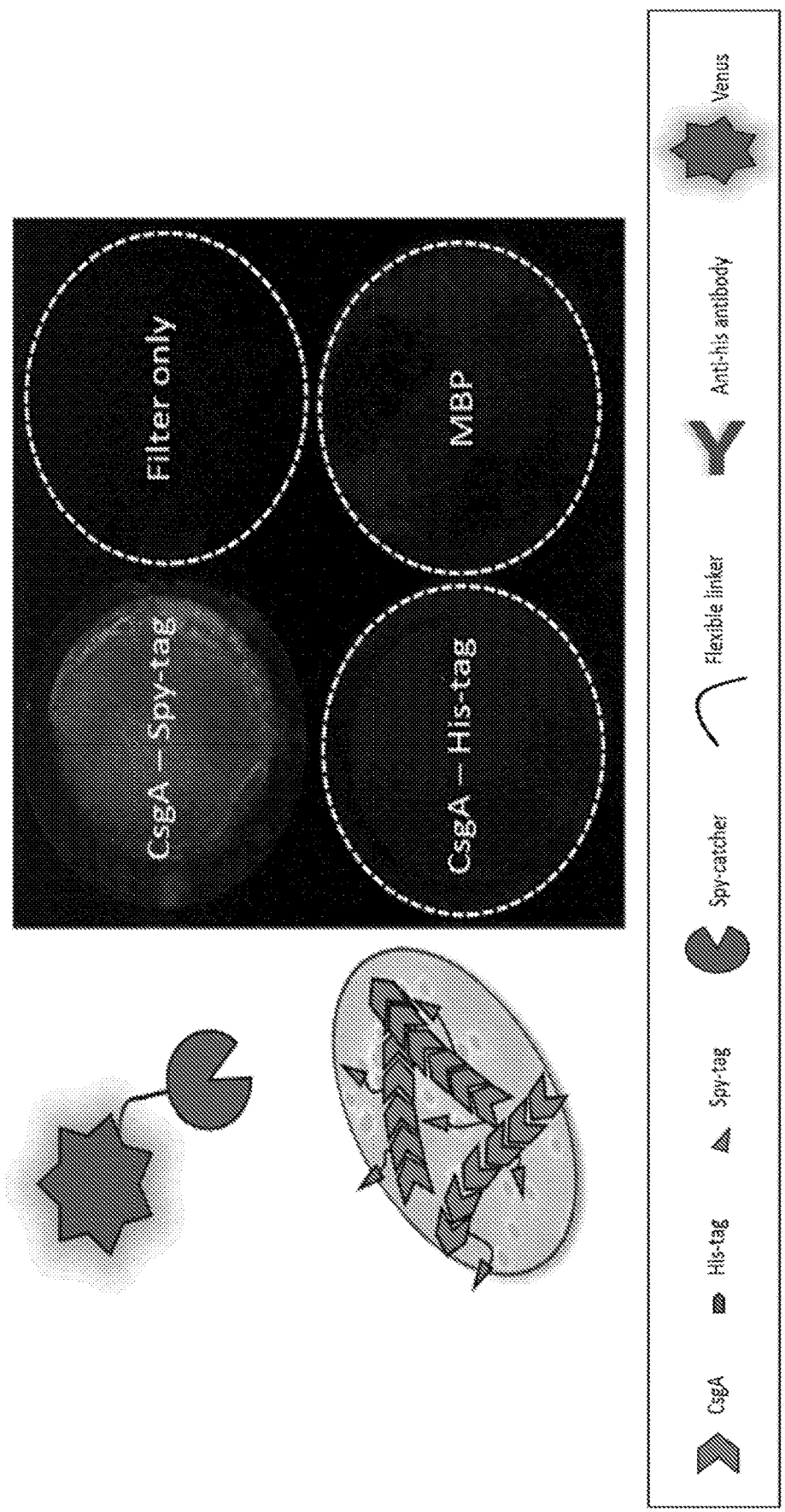
Figure 5C:
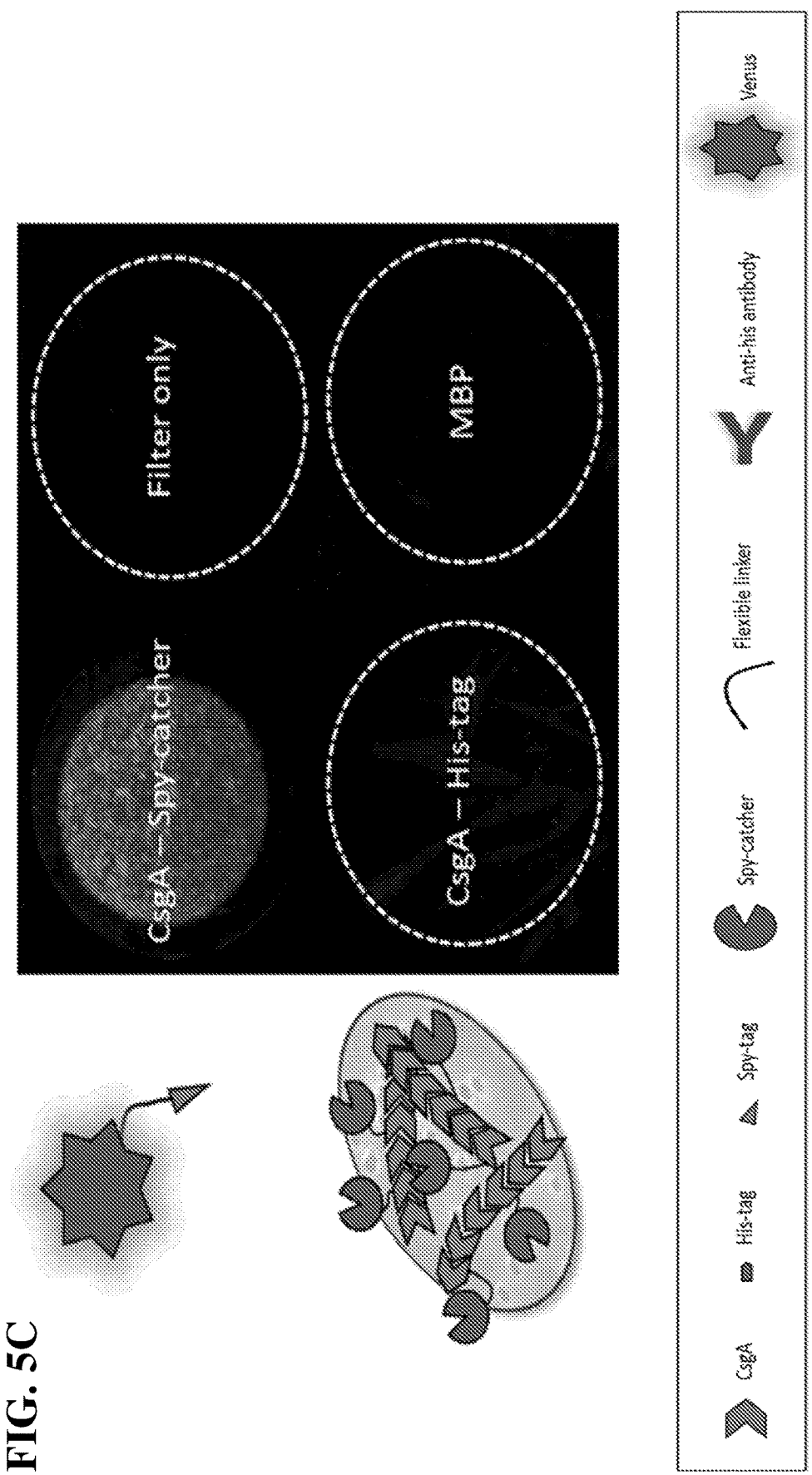
Figure 10:
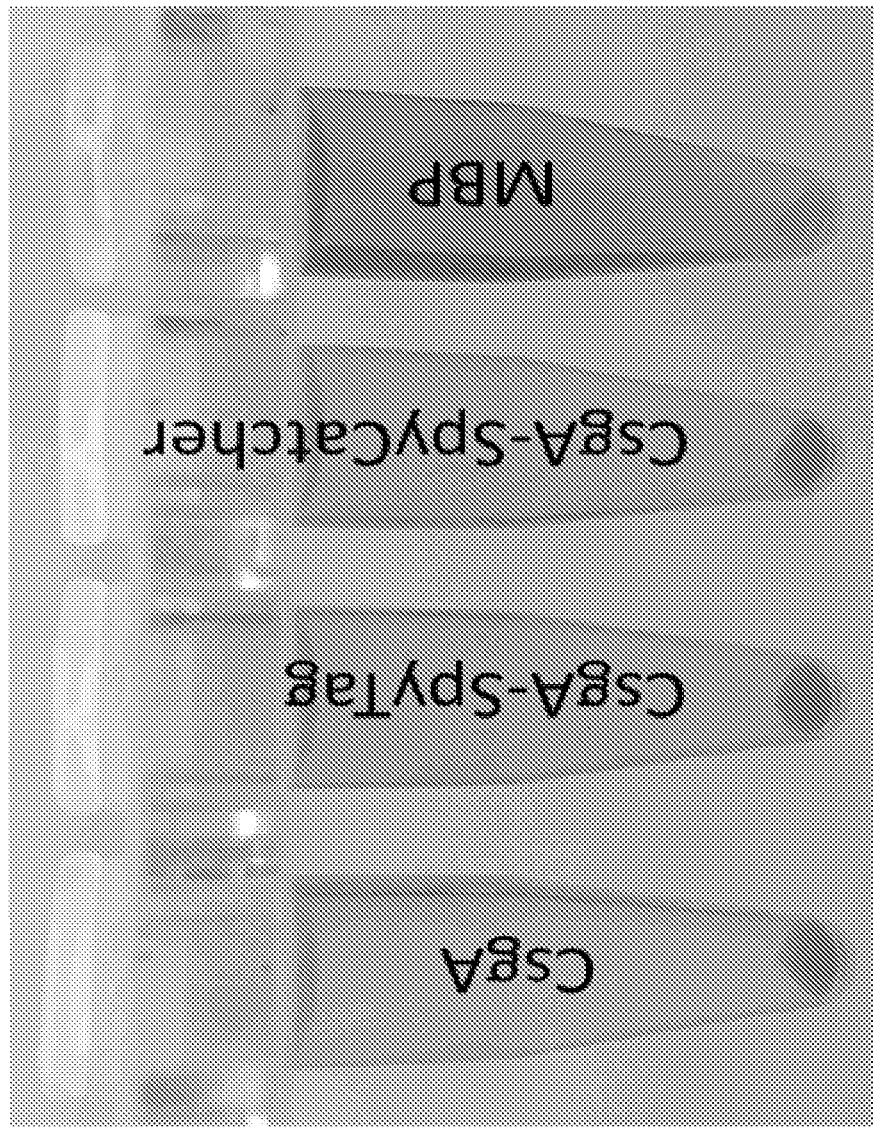
FIG. 10 depicts a Congo Red pull down assay for CsgA, CsgA-SpyTag, CsgA-SpyCatcher, and a maltose-binding protein control. A clear supernatant indicates that Congo Red is bound to curli fibers in the pellet.

In addition to short peptide tags, the utility of the methods of the present invention to the display of longer functional protein sequences was demonstrated. Secretion efficiency is difficult to predict a priori based on size and sequence alone. Genes encoding CsgA-SpyCatcher fusions were constructed. The SpyCatcher domain is 116 residues with a complex β-sheet structure. As shown in FIG. 10, the CsgA-SpyCatcher fusions could be expressed and purified as assembled curli fibers using the filtration protocol. As shown in FIG. 5B, the SpyCatcher domain also remarkably remained active and could covalently capture fluorescent Venus-SpyTag proteins, even after exposure to the highly denaturing filtration protocol.

These results suggest that engineered amyloid fibers that vary widely in sequence length (e.g., CsgA fusions containing small tags or large protein domains) could be purified via filtration and remain functional.

Example 7: Recycling Purified Curli Fibers

Curli fibers purified via filtration were dissolved in a 1:1 hexafluoroisopropnaol (HFIP):trifluoroacetic acid (TFA) solution, with sonication for 1 h. After complete dissolution, the fibers were reformed by dropcasting the CsgA containing solutions directly onto oxygen plasma-treated silicon or glass substrates, and the substrates were allowed to dry under ambient conditions for 1 hour. After drying, the substrates were rinsed with water and 70% (v/v) ethanol.

Figure 7A:
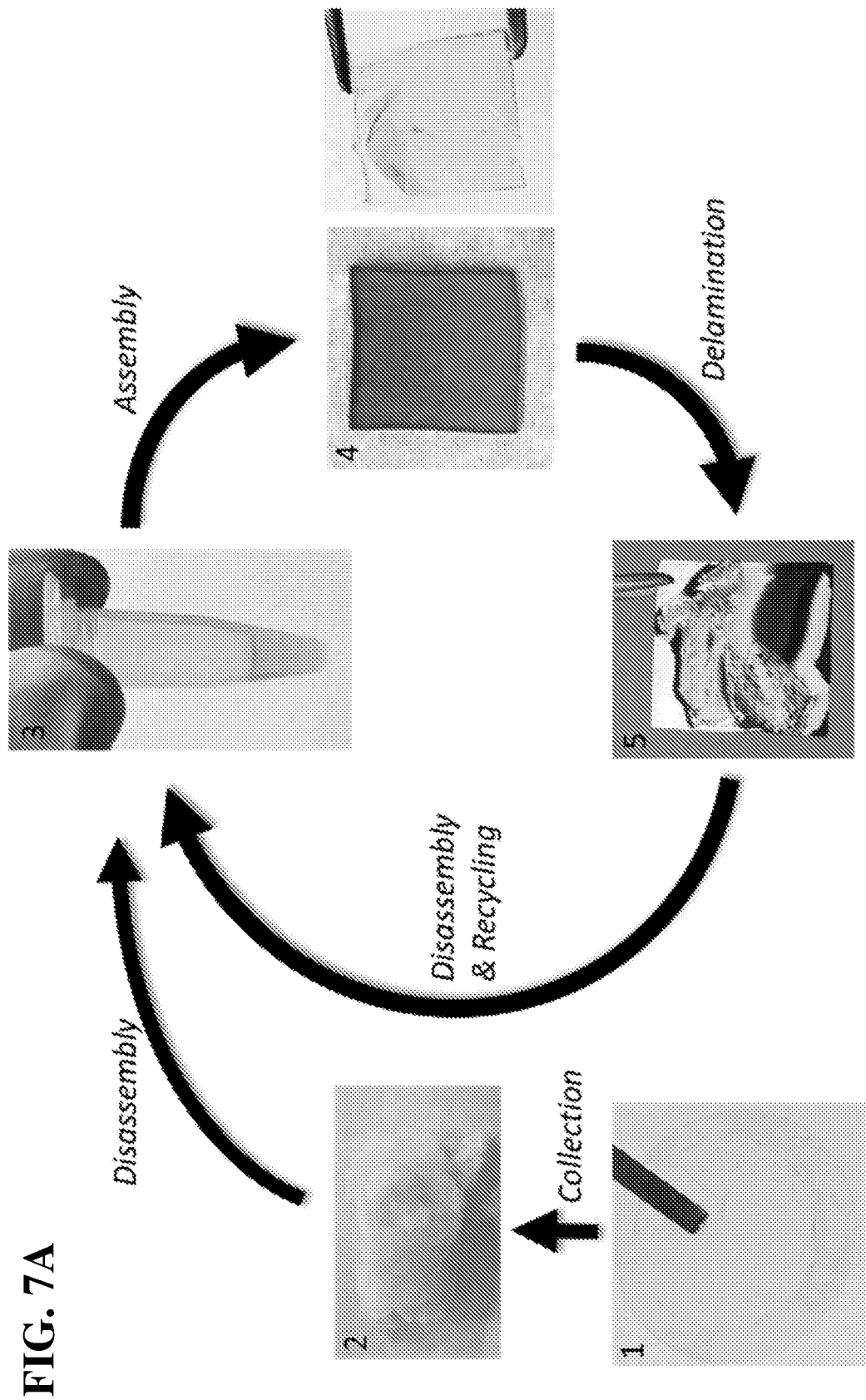
FIGS. 7A and 7B depict the formation and recycling of thin films fabricated from filtered curli fibers.
Figure 7B:
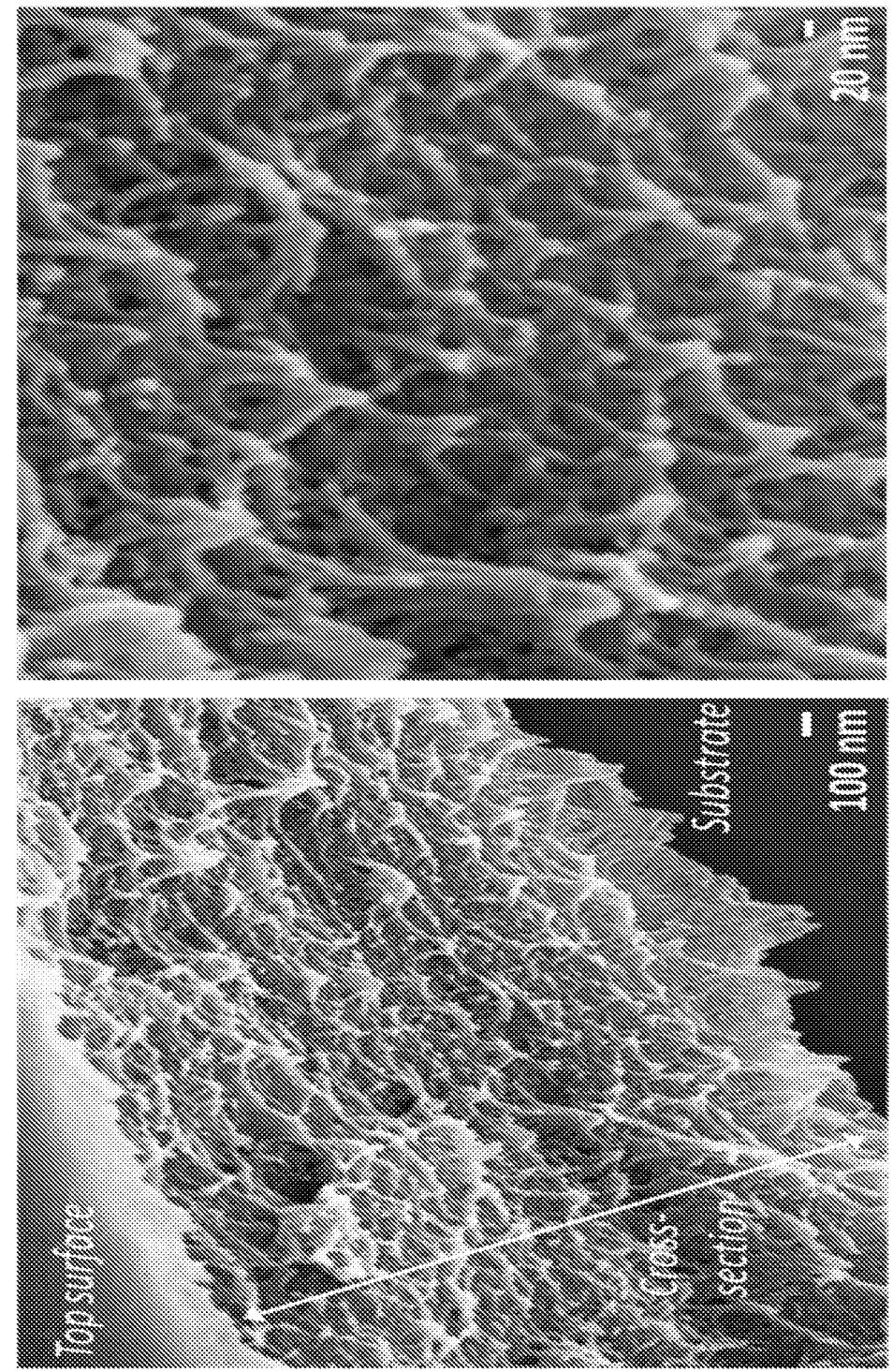

As depicted in FIG. 7A, fibers collected via filtration can be dissolved in an HFIP/TFA mixture with sonication until the solution turns clear, and thin films of fibers can be directly obtained by dropcasting the fiber solution onto substrates. The thin films can be stained with Congo Red, showing the presence of assembled amyloid fibers. The thin films can also be delaminated from the substrates after rinsing with surfactants like SDS, and then re-used to form other films or materials. This cycle can be repeated due to the properties of curli fibers to disassemble on-demand in certain solvents, and to reassemble when these solvents evaporate. As shown by FIG. 7B, SEM imaging confirmed that the fibers reassembled upon drying, showing a highly porous and fibrous film cross-section. Such recycling of curli nanofibers could greatly reduce the production cost of curli-based materials that require different material shapes or coating geometries.

Example 8: Scale Up of Curli Nanofiber Filtration Purification and Production

Figure 11B:
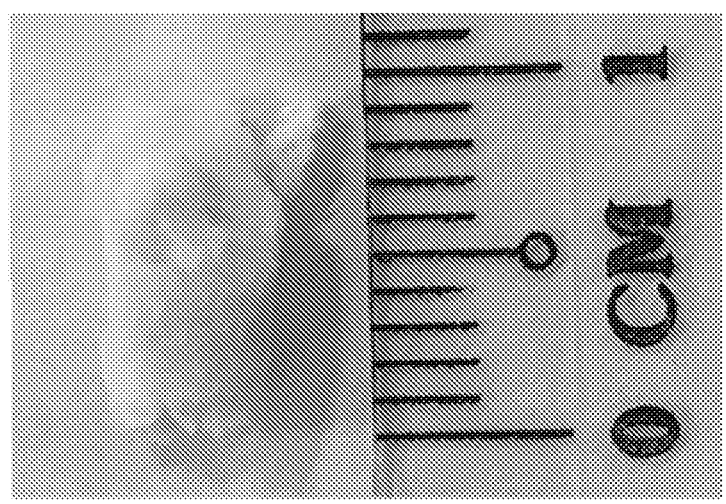
FIGS. 11A and 11B show that filtration purification of curli nanofibers can be scaled up using large filter membranes.
Figure 11A:
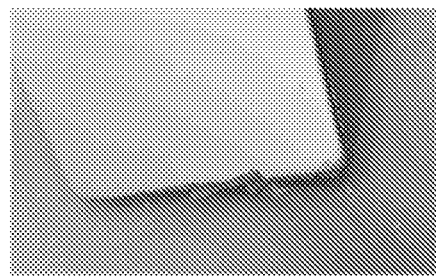
Figure 11A:
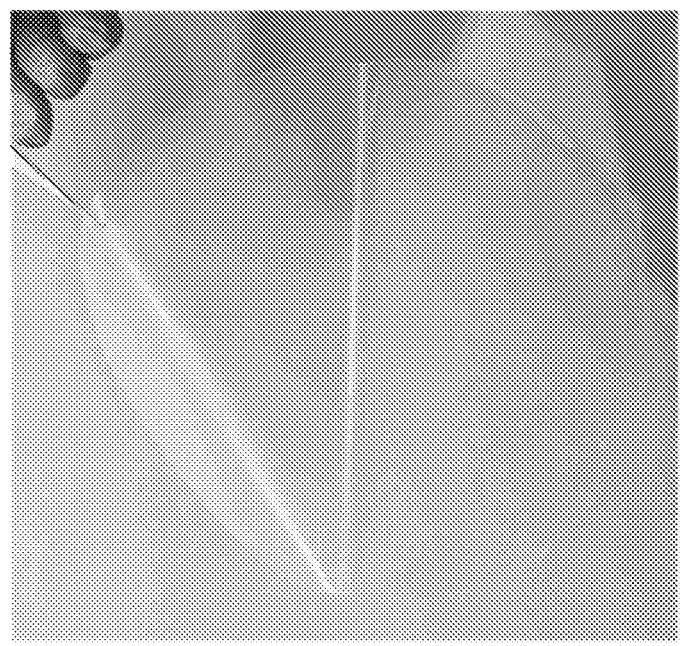

The production yield of pure curli nanofibers was determined by weighing the purified fibers obtained from 40 mL of induced bacterial culture filtered through a single 47 mm diameter membrane after scraping them off with a spatula, as shown in FIG. 11. In a representative filtration procedure, 30 to 45 mg of CsgA-HisTag is yielded per liter of culture. The limiting factor in the scalability of this protocol is clogging of the filter lyophilized purified fibers. By increasing the surface area of the filter membrane, scaling up the filtration purification process is facilitated and can allow for large-scale production of genetically engineered curli nanofibers with a desired function. For example, FIG. 11A-B depicts using a 142 mm diameter filter membrane to filter up to 10 times more culture volume. Filtering large volumes of culture allows the production of hundreds of milligrams of purified curli materials, which translates to easier, low-cost and rapid scalability. In comparison with affinity purification methods for curli fibers, the mass of amyloid materials obtained by filtration is one to two orders of magnitude greater. Collinson et al., Purification and characterization of thin, aggregative fimbriae from *Salmonella enteritidis*. *Journal of Bacteriology* 173(15): 4773-4781 (1991). Coupled with further optimization of the biosynthetic machinery, and the use of batch fermentation, this technique could yield significantly greater quantities of pure protein.

Example 9: Use of Cotton Cloth for Up-Scaling the Use of Catalytic Biofilms

Here we report a modular, multi-enzymatic, self-assembling flow reactor based on enzyme decorated *E. coli* amyloid fibers (curli). The system reduces the cost and increases the predictability of enzyme immobilization procedures by autonomously assembling a biosynthetically-produced enzyme modified matrix without the need for any enzyme purification and with the potential to regenerate itself.

The development of the Biofilm-Integrated Nanofiber Display (BIND) platform, which allows for genetic fusing of peptides or even proteins to CsgA, the monomeric subunit of curli fibers, has been used to generate curli fibers modified to present different substrate binding peptides (e.g., steel, carbon nanotubes, gold surfaces) or peptides for metal sequestration. Additionally, CsgA has been modified with peptides that interact with small protein units forming covalent or non-covalent interaction for enzyme immobilization on curli fibers (Nguyen et al. (2014) *Nature Comm.* 5: 4945; and Botyanszki et al. (2015) *Biotechnol. Bioengin.* 112(10): 2016-24).

By filtering the modified curli fibers onto cotton cloth, the time- and cost-consuming impediments of biofilm formation are resolved. Because the bacteria grow and the expression of curli fibers occurs in suspension, the formation of the biomass only takes one day and the whole biomass can be filtered on the cotton cloth. During this filtering process, curli fibers are deposited on the cotton fibers. Because the curli fibers bind to cellulose (Blanco et al. (2012) *Trends Microbiol* 20(2): 66-73), this binding process is highly effective and the vast majority of the curli fibers can be bound onto the cotton cloth. Additionally, cotton cloth is a very cheap supporting material, is flexible and thin. Immobilizing curli fibers onto cotton results in a big active surface, which can present a variety of peptides for interaction with different materials and allow for the immobilization of an enzyme onto the cotton cloth. For example, enzymes can be immobilized onto cotton cloth for biocatalysis purposes (as both single enzymes or multiple enzymes may be displayed on curli fibers immobilized onto the cotton cloth to build an enzymatic cascade). The immobilization step can be performed using crude cell lysate and does not require a cost-intensive protein purification step, which allows for inexpensive production of our enzymatically active surfaces.

The cotton cloth comprising immobilized curli fibers can be wrapped and placed into a flow cartridge. Enzymes may be contacted with the cartridge containing the cloth, where they are immobilized onto the curli fibers, resulting in a enzymatically-active flow reactor. However, enzymatically-active flow reactors are not the sole field of use for this system. Enzymes attached to curli fiber-modified cotton may also be used as filters. For example, the system may also be used for the degradation of organophosphates (e.g., the active agents in chemical warfare agents such as Sarin, Tabun, and VX nerve agents), wastewater treatment (e.g., to degrade hormones). Further, by displaying heavy metal-binding peptides on curli fibers, the filters may also be used for the sequestration of toxic metals. Moreover, textiles with enhanced functionalities may be produced. For example, by immobilizing enzymes such as amylase, proteases or lipases, which are used in laundry detergents, the system may be used to degrade stains immediately upon contact of the enzyme substrate with the textile. Curli fibers displaying antimicrobial peptides may be used eliminate the emergence of bad odors in clothes.

Expression of SpyTag-Curli Nanofibers

Colonies of transformed PQN4 and PHL628-cells were picked for inoculation of 5 mL LB containing 100 µg/mL carbenicillin, and additional 2% (m/v) glucose for PQN4 cultures. Cultures were grown for 6 hours at 37° C. and shaken at 225 rpm (Multitron Standard Incubator, Infors HT). For curli fiber expression in PQN4, cultures were diluted 100-fold in fresh LB medium with 100 µg/mL carbenicillin, and expression was allowed overnight at 37° C. 225 rpm. For expression in PHL628, cultures were diluted 100-fold in YESCA medium and incubated at 37° C. and shaken at 225 rpm until an optical density (OD) of 0.5-0.6 at 600 nm was reached. Expression was induced by adding Isopropyl-β-D-thiogalactopyranoside (IPTG) to a final concentration of 3 mM, and the cultures were incubated at 25° C. overnight. For relative quantification of curli nanofiber expression, a pulldown assay was performed by spinning down 1 mL of cell culture for 5 min at 8,000×g and resuspending the pellet in 1 mL 0.0015% (m/v) Congo Red solution, followed by a 10 min incubation and centrifugation for 10 min at 16,900×g. Absorbance was measured in triplicate at 490 nm, and absorbance values of the samples were subtracted from absorbance of Congo Red solution.

Preparation of SpyCatcher-Enzyme Cell Lysate

Colonies of transformed BL21 cells grown on LB agar plates with 100 µg/mL carbenicillin were picked for inoculation of 5 mL LB medium with 100 µg/mL carbenicillin. Cultures were grown overnight at 37° C. and shaken at 225 rpm, and the overnight cultures were subsequently diluted 100-fold in fresh LB medium with 100 µg/mL carbenicillin. When an OD of 0.5-0.6 at 600 nm was reached, expression was induced with 3 mM IPTG and cultures were incubated overnight at 20° C. and shaken at 225 rpm. Next, cell cultures were centrifuged for 15 min at 5,000×g, and the pellet was resuspended in 30 mL lysis buffer (30 mL TBS-T (20×TBS Tween 20 Buffer (28360, ThermoFisher); 1.2 µL benzonase=1 U/mL; 2 mM $Mg^{2+}$; 2 cOmplete Ultra tablets (Mini, EASYpack Protease Inhibitor Cocktail (Sigma Aldrich)) per 500 mL cell culture. Resuspended cells were subjected to 6 sonication cycles with 30 s sonication at 40% amplitude each followed by a 30 s break, and centrifuged at 20,000×g for 30 min. The supernatant was collected and stored on ice.

Enzyme Immobilization on Cotton Pieces

Cotton pieces with 5 cm diameter were cut out of cotton fabric. The cotton pieces were washed by vacuum-filtering 10 mL TBS-T, and 40 mL curli nanofiber culture were applied and filtered. After three rinses with 5 mL TBS-T, the cloth was incubated with 10 mL 8 M guandine hydrochloride (GdmCl) for 10 min. Next, three rinses with 5 mL TBS-T followed, and the cotton pieces were cut to fit to 6-well plates and each piece was transferred into a well with the upper side of the cotton pieces facing upwards. 3 mL 5% milk in TBS-T were added and incubated for 1 hour with a VWR Standard Orbital shaker at RT, and subsequently a 2 hour incubation in 2-fold diluted enzyme lysate in 5% milk in TBS-T followed under the same conditions. After three rinses with 3 mL TBS-T, 3 mL assay buffer were added and incubated for 30 min under constant shaking.

Amylase Activity Measurement on Cotton Pieces

All experiments were carried out in duplicate, and activity was determined by using 10 mM NAD+ in 100 mM Tris pH 7.5 as assay buffer and measuring NADH absorbance at 340 nm after 30 min shaking at a VWR Standard Orbital shaker at RT. All measurements were performed in triplicate and absorbance of a substrate blank was subtracted.

PTDH Activity Measurement on Cotton Pieces

All experiments were carried out in duplicate, and activity was determined by using 1 mM pNPMP in PBS pH 7.4 as assay buffer. After 60 min shaking with a VWR Standard Orbital shaker at RT, 5% v/v 1 M NaOH was added to stop the reaction and to convert all pNP to the deprotonated state. The pNP absorbance was measured at 405 nm. All measurements were performed in triplicate and absorbance of a substrate blank was subtracted.

Stability Experiments on Cotton Pieces

Stability measurements under varying conditions were performed either solely on curli SpyTag-nanofibers that were treated with GdmCl and washed three times (as described above), or on curli SpyTag-nanofibers with immobilized PTDH SpyCatcher after rinsing them three times. Drying was performed by drying cotton pieces for 10 min under air flow. For imitating washing conditions, the cotton pieces were incubated at 30° C. and 0.01% SDS for half an hour under constant stirring.

Bioreactor Set-Up

A 13 cm diameter circle was cut out of cloth, and 35 mL TBS-T were filtered by vacuum filtration as a washing step. Subsequently, 200 mL of untreated cell culture were applied and another washing step was performed by filtering 35 mL TBS-T. Two strips (5 cm wide each) were cut out of one circle and a total of 6 strips was assembled into an acrylamide cartridge, with the side with curli fibers pointing towards the outside of the cartridge in order to assemble the bioreactor. All subsequent steps were performed in the assembled reactor through a bottom-up liquid flow controlled by a peristaltic pump. 30 mL 8 M GdmCl were pumped through the reactor at a rate of 3 mL/min. Subsequently, a washing step with TBS-T (40 mL at 6 mL/min) and a blocking step with 5% milk in TBS-T (180 mL at 3 mL/min) were performed, before applying crude cell lysate of PTDH-SpyCatcher expressing BL21 cells (180 mL at 3 mL/min) for enzyme immobilization. The reactor was washed with milk (40 mL, 6 mL/min) and once with 100 mL TBS-T (6 mL/min) to remove non-specifically bound enzyme. The reactor was stored at 4° C. in 0.02% Sodium azide in TBS-T and for every activity measurement, the reactor was washed with 40 mL of TBS-T (3 mL/min) and two 1 mL samples were taken during the subsequent incubation in assay buffer (3 ml/min). Absorbance measurements at 340 nm were performed in triplicates in 96-well plates at a Synergy H1 Hybrid Multi-Mode Microplate reader (BioTek). 100 µL of a 5-fold diluted PTDH-SC sample in substrate, incubated for 10 min at 750 rpm RT in an Eppendorf thermocycler, served as control.

Results

Figure 16A:
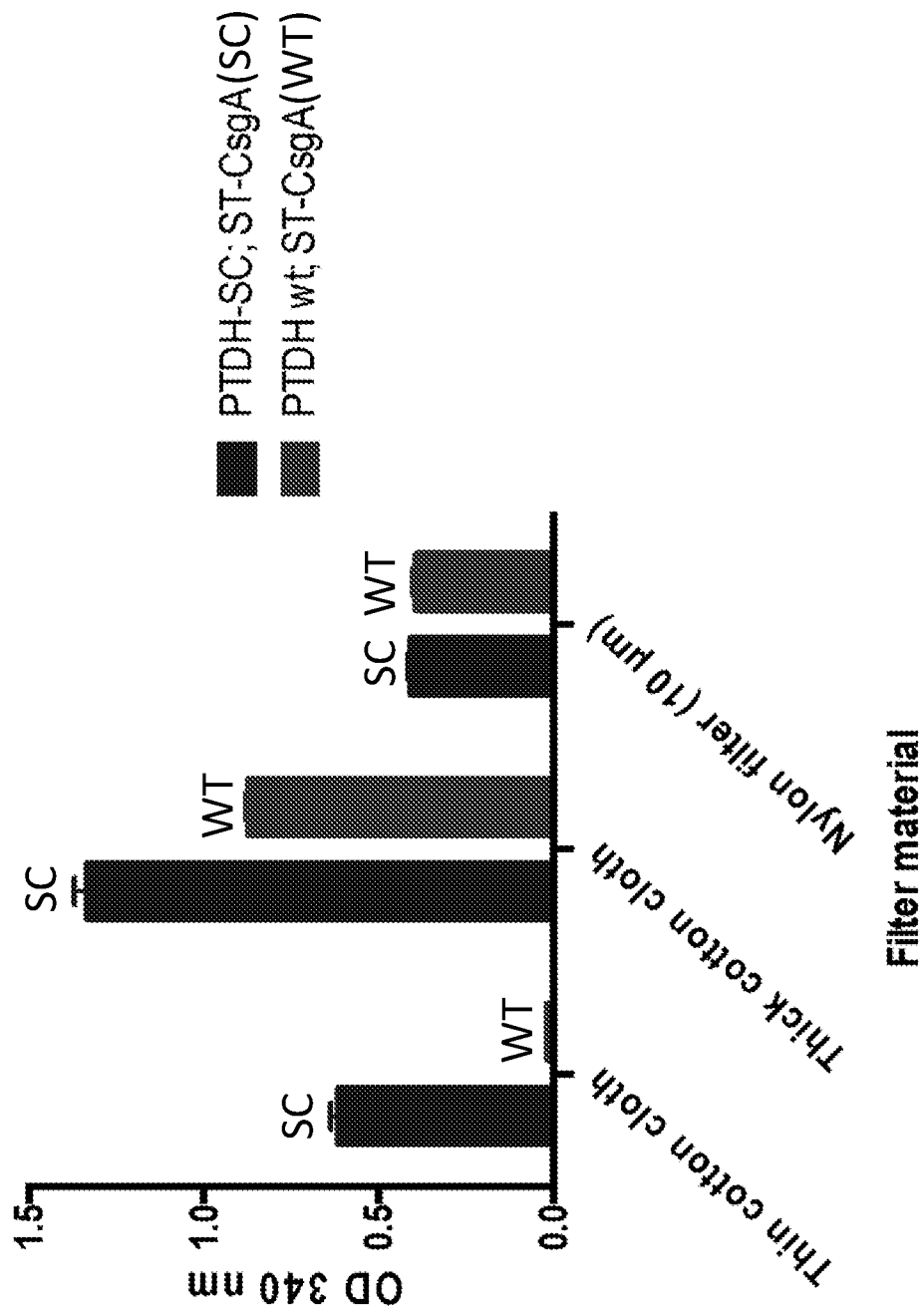
FIG. 16A is a bar graph showing PTDH activity observed in three different filter materials wherein curli fibers comprising SpyTag-CsgA were deposited, after treatment with either wild-type phosphite dehydrogenase (PTDH) or PTDH-SpyCatcher to immobilize the enzyme onto the curli fibers. OD 340 nm corresponds to the absorbance of formed NADH.
Figure 16C:
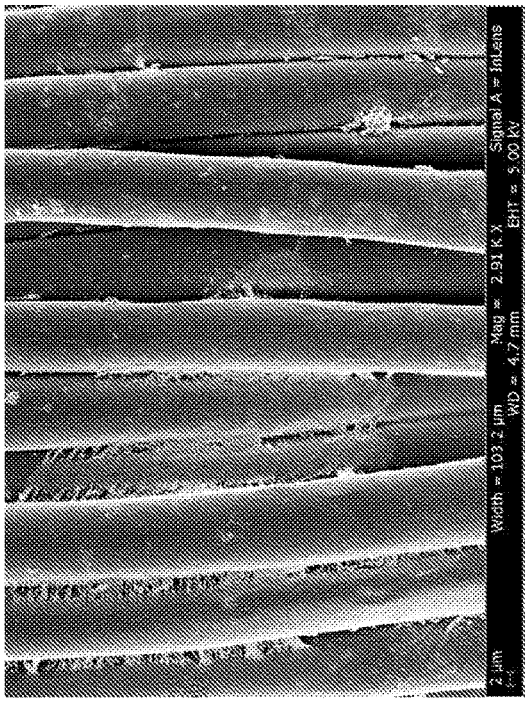
FIG. 16C is an SEM image of ST-CsgA deposited on a thick cotton cloth.
Figure 16B:
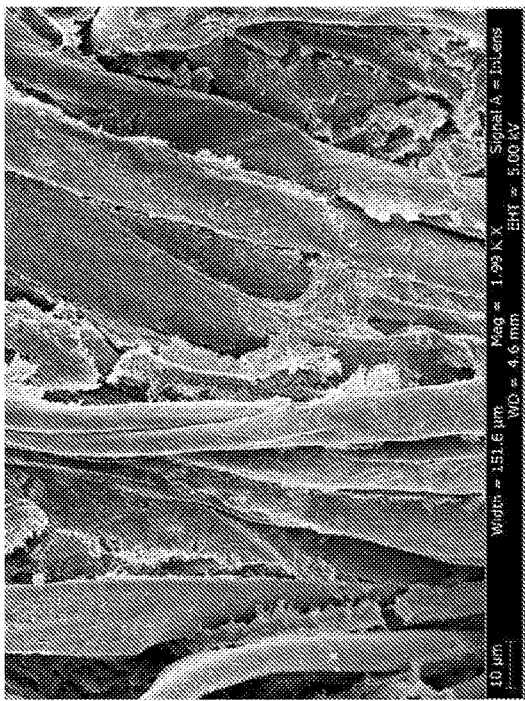
FIG. 16B is an SEM image of ST-CsgA deposited on a thin cotton cloth.
Figure 16D:
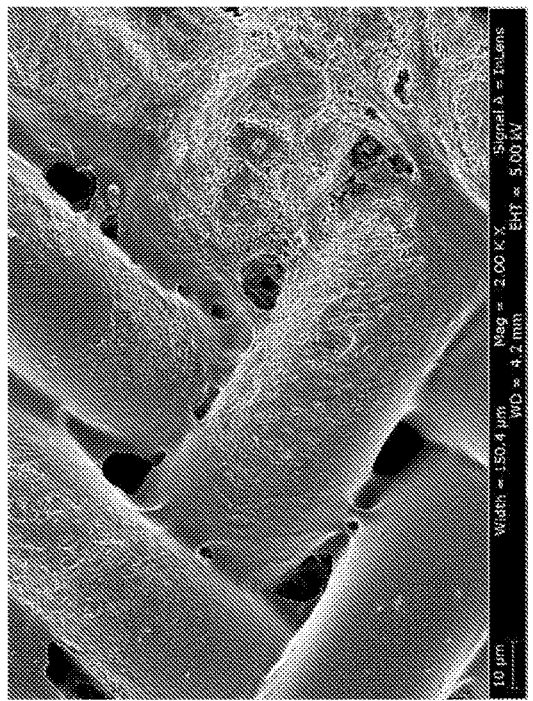
FIG. 16D is an SEM image of St-CsgA deposited on a nylon filter.

Curli fibers comprising SpyTag-CsgA (ST-CsgA) was deposited onto different filter materials (i.e., thin cotton cloth, thick cotton cloth or nylon filter) to evaluate their potential for the use in a flow-based reactor. Subsequently the filter materials were incubated with either wild-type phosphite dehydrogenase (PTDH) or PTDH-SpyCatcher. Scanning electron microscopy was performed to assess the morphology of the ST-CsgA bound to the different filter materials (see FIGS. 16B-16C). The specificity of binding of the PTDH-SpyCatcher to the SpyTag-CsgA deposited on the filters was assessed using the assay described above. As shown in FIG. 16A, the thick cotton cloth showed the highest enzyme activity, but non-specific bound enzyme was observed. Further, the PTDH enzyme bound non-specifically to the nylon filter (pore size: 10 µm). In contrast, the thin cotton cloth exhibited almost exclusive specific-enzyme binding. Due to the small thickness and the good performance of the thin cotton cloth, the remaining experiments were performed using this material.

Figure 17:
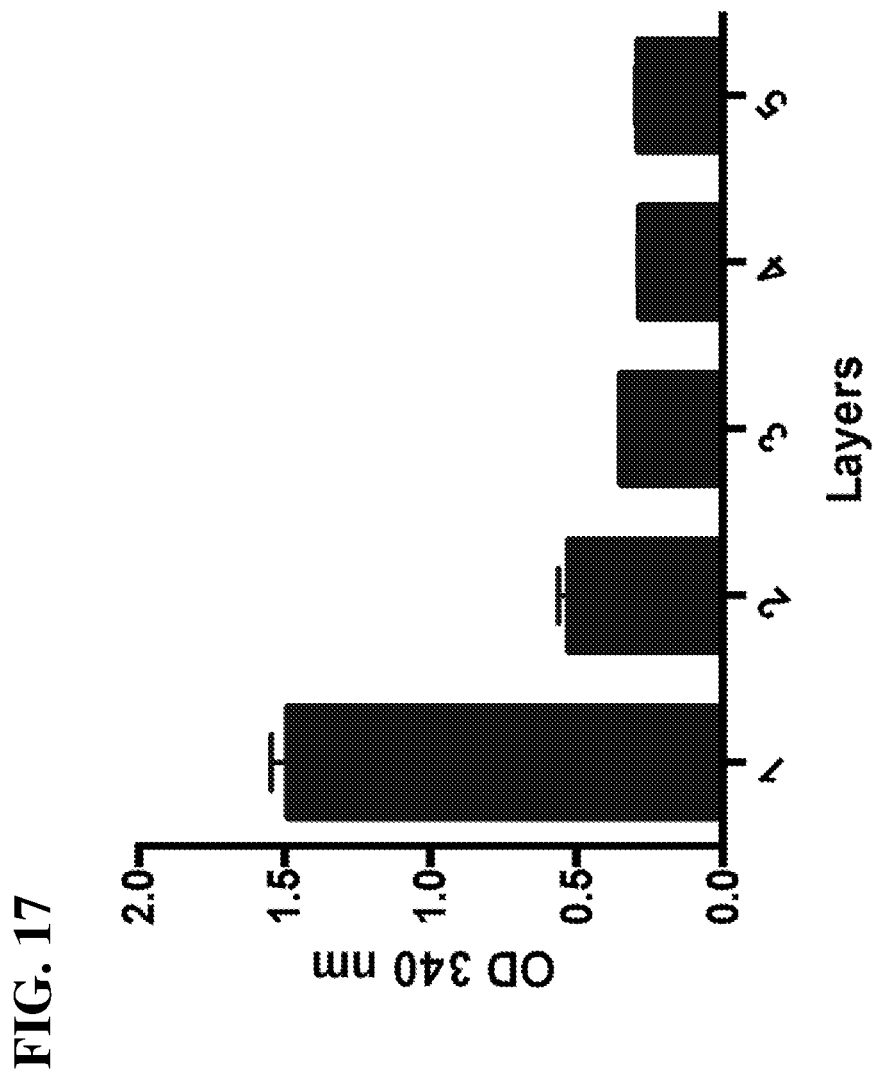
FIG. 17 is a bar graph showing the PTDH activity observed in each of five layers of cotton cloth in which curli fibers comprising SpyTag-CsgA were deposited, followed by PTDH-SpyCatcher enzyme immobilization. OD 340 nm corresponds to the absorbance of formed NADH.

To optimize the procedure for curli fiber deposition onto thin cotton cloth, five layers of cloth were stacked, and curli fibers comprising the ST-CsgA were deposited on the layers of cloths. Subsequently, the PTDH-SpyCatcher enzyme was individually immobilized onto each layer and activity was measured as described above. As shown in FIG. 17, the top layer (1) showed clearly the highest enzyme activity of all the layers. This observation implies that the most effective curli binding occurred at the first layer and therefore, curli fibers cannot be deposited on multiple cotton cloths simultaneously.

Figure 18B:
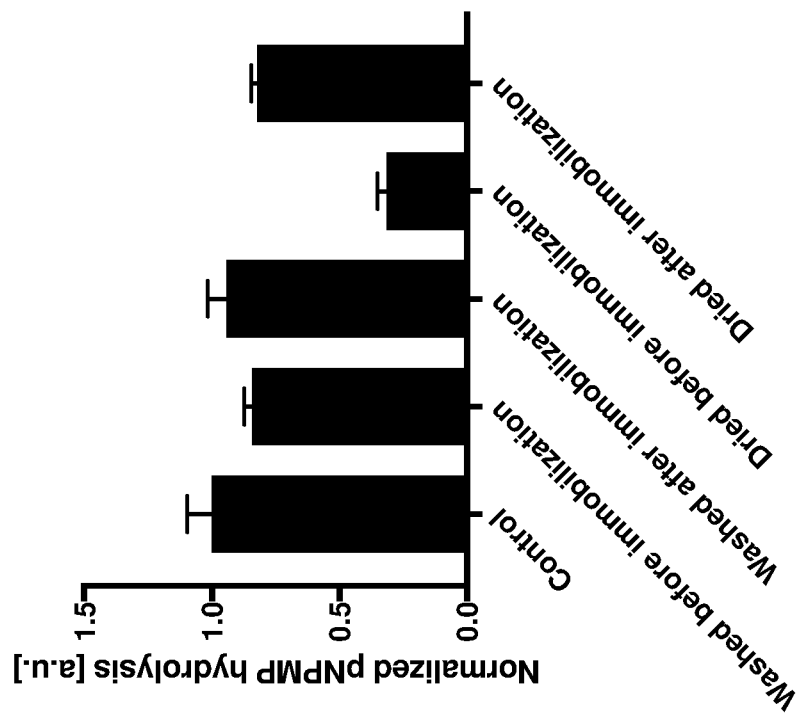
FIG. 18B is a bar graph showing amylase activity observed on a thin cotton cloth to which curli fibers comprising ST-CsgA were deposited, and amylase-SpyCatcher was immobilized, following the indicated washing and drying treatments.
Figure 18A:
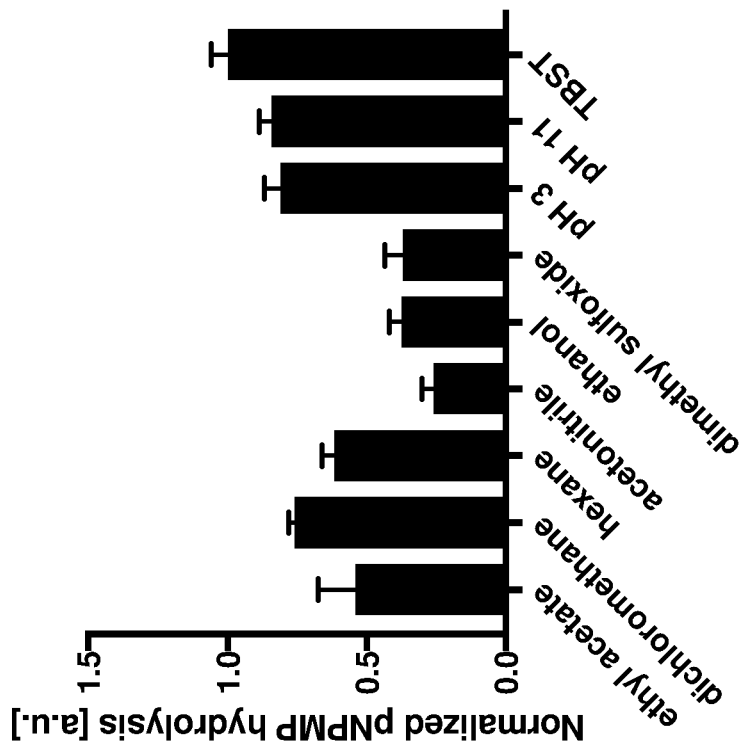
FIG. 18A is a bar graph showing amylase enzyme activity observed on a thin cotton cloth to which curli fibers comprising ST-CsgA were deposited, and amylase-SpyCatcher was immobilized, after treatment with different organic solvents, acidic conditions, or basic conditions.
Figure 18C:
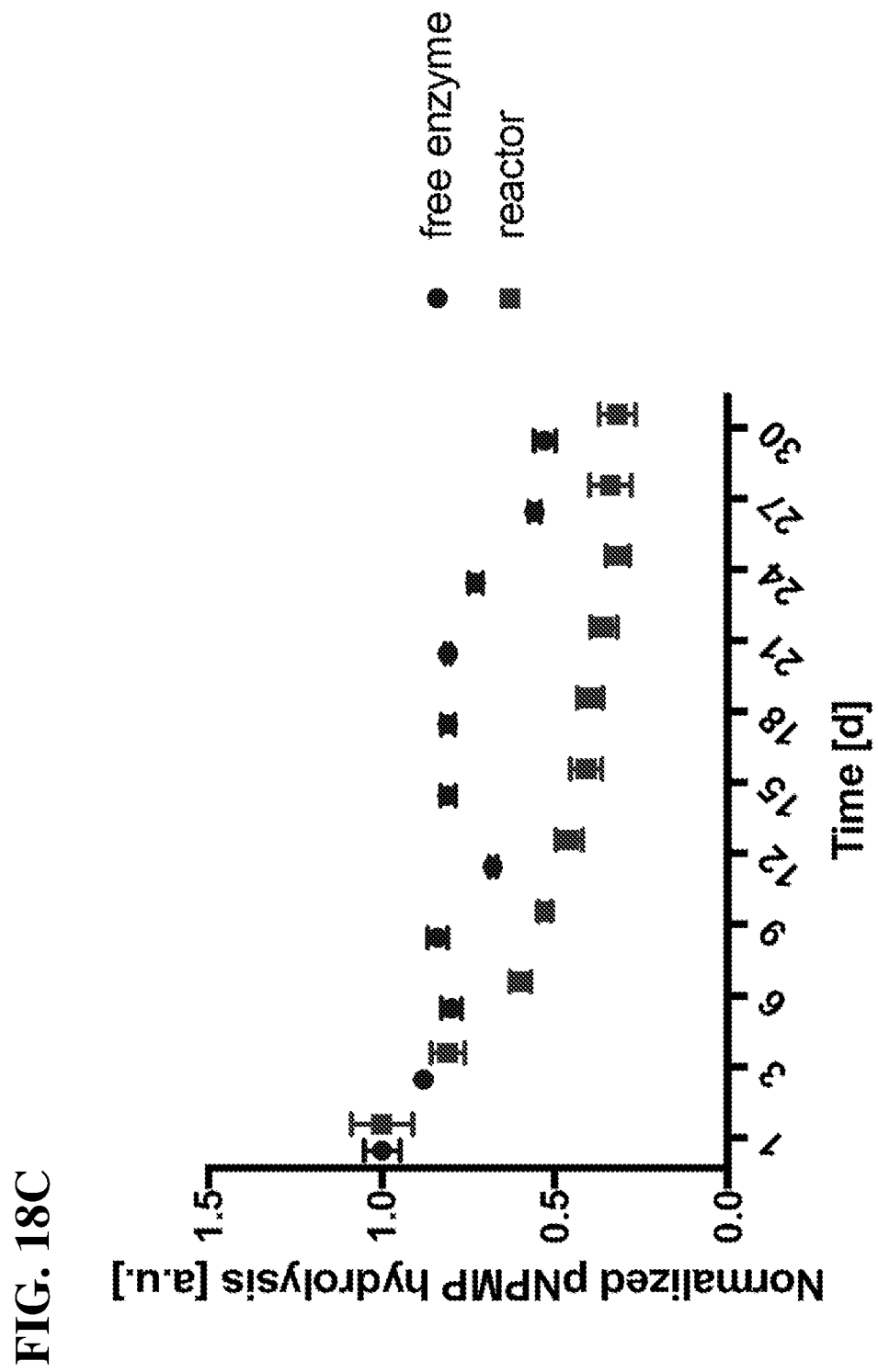
FIG. 18C is a graph showing the amylase enzyme activity observed in a reactor comprising a thin cotton cloth to which curli fibers comprising ST-CsgA were deposited, and amylase-SpyCatcher was immobilized, over a period of 30 days.

The stability of the ST-CsgA deposited onto thin cotton cloth was tested using multiple methods, as shown in FIGS. 18A-18C. First, the cloth was incubated for 30 minutes in different organic solvents, acidic and basic conditions. Subsequently, enzyme (e.g., amylase-SpyCatcher) was immobilized and the activity was measured. As shown in FIG. 18A, while the acidic and basic conditions impaired the deposited curli only negligibly, exposure to either acetonitrile, ethanol, or DMSO resulted in the activity being decreased by more than half. Dichloromethane had the weakest effect of the organic solvents tested. Second, the impact of washing and drying on the curli fibers and enzymes was tested. To test the stability of the curli fibers on cellulose, the enzymes were immobilized after washing and drying. For the testing of the impact on enzyme activity, the enzyme was immobilized before washing and drying. As shown in FIG. 18B, a decrease in enzymatic activity was only observed when the cloth with curli fibers was dried prior to immobilizing the enzyme onto the deposited curli fibers. Finally, the stability of amylase-SpyCatcher immobilized on curli fibers comprising St-CsgA present in a reactor was compared to free enzyme over a 30 day period. As shown, in FIG. 18C, amylase activity was observed throughout the experiment.

The system described herein has several benefits over other systems. The system is able to present a variety of peptides with different functions on a thin and flexible surface. Focusing on enzyme immobilization, this system is a very fast and economic method to specifically immobilize enzyme onto a surface. Long surface treatment or enzyme purification steps are necessary. Further, because the interactions between the enzymes and the curli fiber polypeptides and based on protein-protein interactions, conjugation chemistry is not needed, which contributes to the environmental compatibility of this system. By immobilizing curli on cotton cloth, a thin and flexible surface to present a variety of functional peptides is created. These peptides functionalize the cloth with their inherent properties, and enable to immobilize enzymes on the cotton.

Conclusion to Examples

Figure 8:
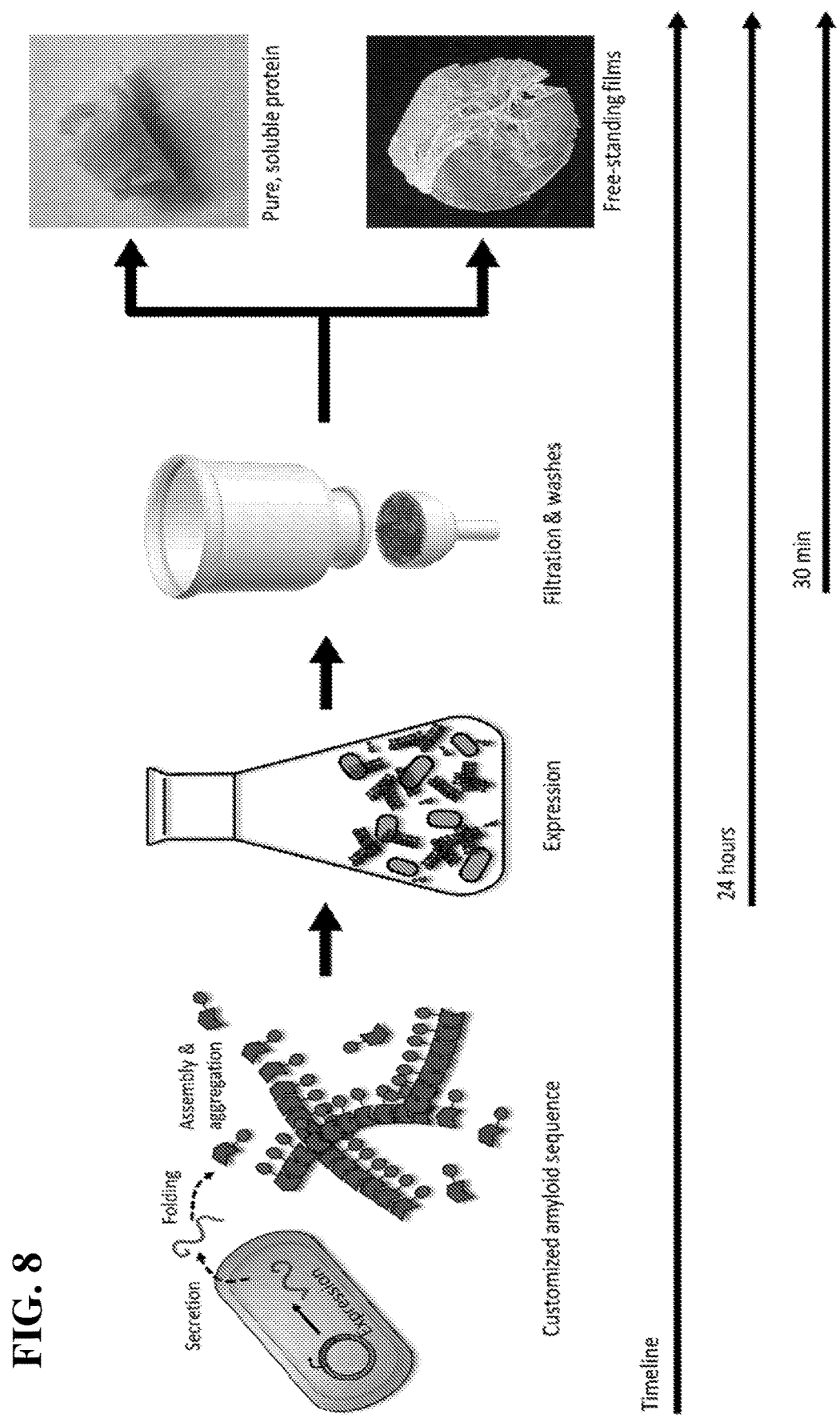
FIG. 8 depicts the workflow for fabricating genetically engineered curli-based macroscopic materials based on fast and simple processing steps. Cloning steps and transformation of engineered bacteria with a customized CsgA variant requires two to three days. Growth and expression of assembled curli fibers can be accomplished in 24 hours, after which filtration and washes are carried out in 30 minutes, producing enough pure protein to assemble various materials like free-standing thin films.

The methods described herein, schematically depicted in FIG. 8, demonstrate a novel, streamlined and scalable purification procedure for recombinantly produced amyloid proteins. The procedure, which relies on filtration, followed by washes in chaotropic solutions, is particularly suited to the purification of the fibrous curli proteins of the E. coli biofilm matrix, due to their propensity to self-assemble into extracellular micro-scale aggregates in the absence of CsgB, and their remarkable resistance to denaturing agents. However, other fibrous proteins that exhibit similar properties may be compatible with this general scheme, depending on their resistance to denaturants in the assembled state. The diameter of the filter membrane pores could be adjusted as a function of the size of the aggregates and the concentration and nature of the denaturing agents could also be modified to suit a broad range of protein-based materials. Overall, the methods enable the isolation of pure, assembled curli fibers, and can be easily scaled to isolate quantities of protein in the hundreds of milligrams, or more, with easily accessible equipment.

The methods described herein constitute an easier and cheaper way to obtain sufficient quantities of protein to fabricate macroscopic materials, without sacrificing molecular-level control over structure, when compared to other purification techniques, which usually require several time consuming and low-yielding steps. The methods do not require any purification tag, and are compatible with curli variants with widely varying structures. The purification protocol can be coupled with several techniques to create integrated materials fabrication protocols with these easily engineered proteins. These materials will compare favorably to those created by more specialized fabrication techniques, but with a much simpler workflow. The resulting materials, which can be macroscopic, but retain their nanoscale structure, will be of interest for a wide range of applications for which sequence customizability is critical.

The invention claimed is:

1. A method of producing an amyloid fiber thin film comprising:
   contacting a composition comprising amyloid fibers with a filter membrane;
   washing the filter membrane;
   crosslinking the amyloid fibers on the filter membrane using a crosslinking agent, thereby producing crosslinked amyloid fibers;
   placing a second membrane on top of the crosslinked amyloid fibers, such that the crosslinked amyloid fibers are positioned between the filter membrane and the second membrane, wherein the second membrane is of a different material than the filter membrane;
   dissolving the filter membrane with a solvent;
   drying the crosslinked amyloid fibers on the second membrane; and
   removing the crosslinked amyloid fibers from the second membrane;
   thereby producing a amyloid fiber thin film.

2. The method of claim 1, wherein the amyloid fiber is selected from the group consisting of a curli fiber, a fiber comprising CsgA, a fiber comprising β-lactoglobulin, a fiber comprising sup-35, a fiber comprising Ure2p, a fiber comprising α-synuclein, a fiber comprising amyloid β-protein (A β), a fiber comprising medin, a fiber comprising prolactin, a fiber comprising gelsolin, a fiber comprising calcitonin, a fiber comprising cystatin, a fiber comprising transthyretin, a fiber comprising Pmell 7, and a fiber comprising β2-microglobulin.

3. The method of claim 1, wherein the amyloid fiber thin film comprises a CsgA polypeptide.

4. The method of claim 3, wherein the CsgA polypeptide further comprises a linker and an activity polypeptide, wherein the activity polypeptide is a polypeptide selected from the group consisting of: a conjugation domain, a functionalizing polypeptide, a Histidine tag, a silk protein, a nanobody, a metal binding domain (MBD), a graphene binding (GBP) domain, a carbon nanotube binding (CBP) domain, a gold binding (A3) domain, CT43, FLAG, Z8, E14, QBP1, CLP12, and AFP8; and wherein the linker is attached at one end to the CsgA polypeptide and at the other end to the activity polypeptide.

5. The method of claim 4, wherein the linker is attached to the C-terminus of the CsgA polypeptide or the N-terminus of the CsgA polypeptide.

6. The method of claim 4, wherein the conjugation domain is selected from the group consisting of: SpyTag, EFCA, WRESAI, ARVCF, CaM, SZ21, VMAN11, and DnaE ΔC35.

7. The method of claim 4, wherein the conjugation domain is selected from the group consisting of: SpyCatcher, a PDZ domain, Tip1, InaD, M13, SZ16, VMAΔN11, and DnaEC35.

8. The method of claim 6, wherein the CsgA polypeptide is contacted with a partner conjugation domain attached to a functionalizing polypeptide, wherein the partner conjugation domain is selected from the group consisting of SpyCatcher, a PDZ domain, Tip1, InaD, M13, SZ16, VMAΔN11, and DnaEΔC35.

9. The method of claim 7, wherein the CsgA polypeptide is contacted with a partner conjugation domain attached to a functionalizing polypeptide, wherein the partner conjugation domain is selected from the group consisting of SpyTag, EFCA, WRESAI, ARVCF, CaM, SZ21, VMAN11, and DnaEΔC35.

10. The method of claim 4, wherein the functionalizing polypeptide is an enzyme.

11. The method of claim 10, wherein the activity of the enzyme is maintained after the dissolving step.

* * * * *